(12) United States Patent
Au et al.

(10) Patent No.: US 7,625,860 B2
(45) Date of Patent: Dec. 1, 2009

(54) METHODS AND COMPOSITIONS FOR MODULATING CELL PROLIFERATION AND CELL DEATH

(76) Inventors: Jessie L.-S. Au, 2287 Palmleaf Ct., Columbus, OH (US) 43210; M. Guillaume Wientjes, 2287 Palmleaf Ct., Columbus, OH (US) 43210

( * ) Notice: Subject to any disclaimer, the term of this patent is extended or adjusted under 35 U.S.C. 154(b) by 373 days.

(21) Appl. No.: 10/464,018

(22) Filed: Jun. 18, 2003

(65) Prior Publication Data

US 2004/0010001 A1 Jan. 15, 2004

Related U.S. Application Data

(62) Division of application No. 09/587,559, filed on Jun. 5, 2000, now Pat. No. 6,599,912.

(51) Int. Cl.
*A61K 38/00* (2006.01)
(52) U.S. Cl. ............................................. 514/2
(58) Field of Classification Search ................. None
See application file for complete search history.

(56) References Cited

OTHER PUBLICATIONS

Barry, W, Nature Biotechnology 22, 165-167 (2004).*
Miller, S 2002, J Invest Dermatol, vol. 118, pp. 216-225.*
Iliakis et al., May 1989;16(5):1261-5, abstract only.*
Katsuoka et al., Arch Dermatol Res. 1987;279(4):247-50.*
Ozeki et al., (Tissue Engineering, vol. 8, 2002, pp. 359-366).*
Jimenez, J., et al.,"Protection From 1-β-D-Arabinoturanosyleytosine-Induced Alopecia by Epidermal Growth Factor and Fibroblast Growth Factor in the Rat Model", Cancer Research, 52, 413-415(1992).
Gao, Xiang, et al., "Use of Drug Kinetics in Dermis to Predict in Vivo Blood Concentration After Topical Application", Phar. Research, vol. 12, No. 1 (1995).
Gupta, Elora, et al., "Penetration Kinetics of 2', 3'-Dideoxyinosine in Dermis is described by the Distributed Model", Phar. Research, vol. 12, No. 1 (1995).
Mukherji, E., et al., "Percutaneous Absorption of 2', 3'-Dideoxyinosine in Rats", Phar. Research, vol. 11, No. 6 (1994).
Wang, J., et al., "Protection Against Chemotherapy-Induced Alopecia", Phar. Research, vol. 23, No. 11, (2006).
Bertolotto, C, Maulon, L, Filippa, N. et al., Protein kinase C theta and epsilon promote T-cell survival by a rsk-dependent phosphorylation and inactivation of BAD. J. Biol. Chem., yr 2000, pp. 37246-37250, vol. 275.
Bonni, A, Brunet, A, Eest, AE et al., Cell survival promoted by the Ras-MAPK signaling pathway by transcription-dependent and -independent mechanisms. Science, yr 1999, pp. 1358-1362, vol. 286.
Burgess, WH, and Maciag, T, The heparin-binding (flibroblast) growth factor family of proteins. Ann. Rev. Biochem., yr 1989, pp. 575-606, vol. 58.
Cardone, MH, Roy, N, Stennicke, HR et al., Regulation of cell death protease caspase-9 by phosphorylation. Science, yr 1998, pp. 1318-1321, vol. 282.

Carmean, N, Kosman, JW, Leaf, EM et al., Immortalization of human urothelial cells by human papillomavirus type 16 E6 and E7 genes in a defined serum-free system. Cell Prolif., yr 2007, pp. 166-184, vol. 40.
Chen, C, Edelstein, LC, and Gelinas, C, The Rel/NF-kB Family Directly Activates Expression of the Apoptosis Inhibitor Bcl-xL. Molec. Cell. Biol., yr 2000, pp. 2687-2695, vol. 20.
Delehedde, M, Seve, M, Sergeant, N, et al., Fibroblast growth factor-2 stimulation of p42/44MAPK phosphorylation and IkappaB degradation is regulated by heparan sulfate/heparin in rat mammary fibroblasts. j.Biol. Chem., yr 2000 pp. 33905-33910, vol. 275.
Dell'Era, P. Mohammadi, M, and Presta, M, Different tyrosine autophosphorylation requirements in fibroblast growth factor receptor-1 mediated ukokinase-type plasminogen activator induction and mitogenesis, Molec. Biol. Cell., yr 1999, pp. 23-33, vol. 10.
Devita, VT, Jr., Principles of cancer management: chemotherapy. In: DeVita, V,T,, Hellman,S., Rosengerg,S.A. (eds.) Cancer, principles and practice of oncology, pp. 333-347. Philidelphia: Lippincott-Raven, 1997.
Du, K, and Montiminy, M, Creb is a regulatory target for the protein kinase Akt/PKB. j. Biol Chem., yr 1998, pp. 32337-32379, vol. 273.
Friesel, RE, and Maciag, T, Molecular mechanisms of angiogenesis: fibroblast growth factor signal transduction, FASEB J., yr 1995, pp. 919-925, vol. 9.
Ghoda, L, Lin, X and Greene, WC, The 90-kDa ribosomal S6 kinase (pp90rsk) phosphorylates the N-terminal regulatory domain of IkappaBalpha and stimulates its degradation in vitro. J. Biol. Chem., yr 1997, pp. 21281-21288, vol. 272.

(Continued)

*Primary Examiner*—Misook Yu
(74) *Attorney, Agent, or Firm*—Mueller Smith & Okuley, LLC

(57) ABSTRACT

Methods and compositions for modulating the FGF effect on the sensitivity of malignant and normal cells to anticancer agents are provided. In particular, methods and compositions for inhibiting FGF-induced resistance to a broad spectrum of anticancer agents in solid and soft-tissue tumors, metastatic lesions, leukemia and lymphoma are provided. Preferably, the compositions include at least one FGF inhibitor in combination with a cytotoxic agents, e.g., antimicrotubule agents, topoisomerase I inhibitors, topoisomerase II inhibitors, antimetabolites, mitotic inhibitors, alkylating agents, intercalating agents, agents capable of interfering with a signal transduction pathway (e.g., g., a protein kinase C inhibitor, e.g., an anti-hormone, e.g., an antibody against growth factor receptors), an agent that promotes apoptosis and/or necrosis, an interferon, an interleukin, a tumor necrosis factor, and radiation.

In other embodiments, methods and composition for protecting a cell in a subject, from one or more of killing, inhibition of growth or division or other damage caused, e.g., by a cytotoxic agent, are provided. Preferably, the method includes: administering, to the subject, an effective amount of at least one FGF agonist, thereby treating the cell, e.g., protecting or reducing the damage to the dividing cell from said cytotoxic agent.

21 Claims, 7 Drawing Sheets

OTHER PUBLICATIONS

Gospodarowicz, D, Cheng, J, Lui, GM, et al., Isolation of brain fibroblast growth factor by heparin-Sepharose affinity chromatography: identity with pituitary fibroblast growth factor. Proc. Natl. Acad. Sci. U.S.A. yr 1984, pp. 6963-6967, vol. 81.

Hayashi, I, Nixon, T, Morikawa, M, et al., Adipogenic and anti-adipogenic factors in the pituitary and other organs. Proc. Natl. Acad. Sci. U.S.A., yr 1981, pp. 3969-3972, vol. 78.

Hellman, S. Principles of cancer management: raiation therapy. In: DeVita, V.T., Hellman, S., Rosengery, S.A. (eds), Cancer, principles and practice of oncology, pp. 307-332. Philiedelphia: Lippincott-Raven, 1997.

Kent, KD, and Bomser, JA, Bovine pituitary extract provides remarkable protection against oxidative stress in human prostate epithelial cells. In Vitro Cell Dev. Biol. Anim, yr 2003, pp. 388-394, vol. 39.

Miho, Y, Kouroku, Y, Fujita, E, et al., bFGF inhibits the activation of caspase-3 and apoptosis of P19 embryonal carcinoma cells during neuronal differentiation. Cell Death Differ., yr 1999, pp. 463-470, vol. 6.

Ornitz, DM, Xu, J, Colvin. JS, et al., Receptor specificity of the fibroblast growth factor family, J. Biol. Chem., yr 1996, pp. 15292-15297, vol. 271.

Ozeki, M, and Tabata, Y, Promoted growth of murine hair follicles through controlled release of basic fibroblast growth factor. Tissue Eng, yr 2002, pp. 359-366, vol. 8.

Pollock, GS, Franceschini, IA, Graham, G et al., Neuregulin is a mitogen and survival factor for olfactory bulb ensheathing cells and an isoform is produced by astrocytes, Eur. J. Neurosci., yr 1999, pp. 769-780, vol. 11.

Powers, CJ, Mcleskey, SW, and Wellstein, A, Fibroblast growth factors, their receptors and signaling, Endocrine-Related Cancer, ry 2000, pp. 165-167, vol. 7.

Shimamura, A, Ballif, BA, Richards, SA, et al., Rsk1 mediates a MEK-MAP kinase cell survival signal. Curr. Biol., yr 2000, pp. 127-135, vol. 10.

Spivak-Kroizman, T, Lemmon, MA, Dikic I, et al., Heparin-induced oligomerization of FGF modules is responsible for FGF receptor dimerization, activation and cell proliferation. Cell, yr 1994, pp. 1015-1-24, vol. 79.

Tan. Y, Ruan, H, Demeter, MR, et al., p90(RSK) blocks bad-mediated cell death via a protein kinase C-dependent pathway. J. Biol. Chem., yr 1999, pp. 34867, vol. 274.

Wang, J, Lu, Z and Au, JL, Protection Against Chemotheray-Induced Alopecia, Pharm. Res, yr 2006, pp. 2505-2514, vol. 23.

Wert, MM, and Palfrey, HC, Divergence in the anti-apoptotic signalling pathways used by nerve growth factor and basic fibroblast growth factor (bFGF) in PC12 cells: rescue by bFGF involved protein kinase C delta. Biochem. J., yr 2000, pp. 175-182. vol. 352.

Xing, J, Ginty, DD and Greenberg, ME, Coupling of the RAS-MAPK pathway to gene activation by RSK2, a growth factor-regulated CREB kinase, Science, yr 1996, pp. 9595-9563, vol. 73.

Zong, WX, Edelstein, LC, Chen, C, et al., The prosurvival Bcl-2 homolog Bfl-1/A1 is a direct transcriptional target of NF-kB that blocks TNFa-induced apoptosis. Genes & Development, yr 1999, pp. 382-387, vol. 13.

* cited by examiner

METHODS AND COMPOSITIONS FOR MODULATING CELL PROLIFERATION AND CELL DEATH

CROSS-REFERENCE TO RELATED APPLICATIONS

This application is a divisional application of U.S. Ser. No. 09/587,559, filed Jun. 5, 2000, the disclosure of which is expressly incorporated herein by reference.

RELATED APPLICATIONS

This application claims priority to U.S. Provisional Application No. 60/172,031, entitled "Modulation of Cell Proliferation" filed on Dec. 23, 1999; U.S. Provisional Application No. 60/137,345, entitled "Methods to Diagnose, Prevent, and Overcome FGF-Dependent or FGF-Induced Chemoresistance in Metastatic Sites" filed on Jun. 3, 1999; U.S. Provisional Application No. 60/165,983, entitled "Genes and Gene Products Conferring Reversible Broad Spectrum Anticancer Drug Resistance and Methods of Inhibiting the Same" filed on Nov. 17, 1999; and U.S. Provisional Application No. 60/187,445, entitled "Methods and Compositions for Modulating Cell Proliferation and Cell Death" filed on Mar. 7, 2000, the contents of all of which are hereby incorporated by reference.

BACKGROUND OF THE INVENTION

Resistance of tumor cells to cancer therapy, limited efficacy of cancer therapy in metastatic disease, and undesired host toxicity of cancer therapy are three significant challenges in patient management.

A common resistance mechanism to chemotherapy observed in preclinical studies is the overexpression of drug efflux proteins (Lum, B. L. et al. (1993) *Cancer* 72, 3502-3514; Barrand, M. A. et al. (1997) *Gen. Pharmacol.* 28, 639-645; Fidler, I. J. (1999) *Cancer Chemother. Pharmacol.* 43:S3-S10.). However, at least some clinical studies show that inhibition of the drug efflux proteins does not significantly improve the effectiveness of chemotherapy in patients (Ferry, D. R., et al. (1996) *Eur. J. Cancer* 32:1070-1081; Broxterman, H. J., et al. (1996) *Eur. J. Cancer.* 32:1024-1033), suggesting the existence of other resistance mechanisms.

Cancer therapy, such as chemotherapy and radiation, targets proliferating cells and thereby causes undesired toxicity to normal host tissues that undergo continuous renewal, including the hematopoietic cells, cells in the lining of the gastrointestinal tract, and hair follicles. Bone marrow suppression induced by cancer therapy is, at least in part, overcome by the use of hematopoietic growth factors, including erythropoietin, granulocytes colony-stimulating factor, and granulocyte-macrophage colony-stimulating factor (Gabrilove, J. L. and Goldie, D. W. (1993) In: *Cancer, Principles & Practice of Oncology* (eds. DeVita, V. T. et al., J. B. Lippincott Co., Philadelphia). On the other hand, no treatment is available to overcome the gastrointestinal toxicity and alopecia induced by anticancer agents.

Therefore, there exists a need to identify new mechanisms by which tumor and normal cells elude cytotoxicity of anticancer agents, to identify methods and agents to overcome such resistance in tumor cells, and to utilize these resistance mechanisms to protect normal host tissues from the undesired toxicity of cancer therapy.

SUMMARY OF THE INVENTION

The invention is based, at least in part, on the elucidation of the role played by basic Fibroblast Growth Factor (bFGF) in the induction of broad spectrum resistance to anticancer agents in a number of tumors and metastatic lesions, and the role played by acidic FGF (aFGF) in amplifying the bFGF-induced resistance. Inhibitors of aFGF/bFGF enhance the in vitro and in vivo activity of anticancer agents, and result in shrinkage and eradication of human xenograft tumors including lung metastasis and subcutaneous tumors in mice. Methods of the invention use FGF antagonists to potentiate the antitumor effect of anticancer agents. FGF agonists (e.g., aFGF, e.g., bFGF) reduce the cytotoxicity of anticancer agents to normal noncancerous intestinal epithelial cells. Methods of the invention use FGF agonists to protect normal cells from the cytotoxic effects of anticancer agents.

Accordingly, in general, the invention features, a method of inhibiting unwanted cell growth or division, e.g., reducing or inhibiting the proliferation of, or enhancing the killing of, a cell, e.g., a hyperproliferative cell, e.g., a malignant cell or a benign hyperproliferative cell. The method includes: contacting the cell with at least one cytotoxic agent, (e.g., a cytostatic agent, e.g., an agent that causes cell death) and at least one FGF antagonist, in an amount, which together, is effective to reduce or inhibit the proliferation of the cell, or induce cell killing. Preferably, the unwanted cell is the cell of an established tumor.

In another aspect, the invention features a method of improving the efficacy of an agent, e.g., a cytotoxic agent, in a subject. The method includes:

administering to the subject at least one agent, e.g., a cytotoxic agent;

administering to the subject at least one FGF antagonist.

The FGF antagonist enhances the efficacy of the agent, e.g., a cytotoxic agent, relative to the effect of the cytotoxic agent in the absence of the FGF antagonist.

In a preferred embodiment, the FGF antagonist improves the efficacy of the cytotoxic agent against a cancer, e.g., an established tumor.

In another aspect, the invention features, a method of inhibiting unwanted cell growth or division, or inducing the killing of an unwanted cell (e.g., a hyperproliferative cell), e.g., a cell of an established tumor or a benign hyperproliferative cell, in a subject. The method can be used to treat or prevent, in a subject, a disorder characterized by unwanted cell growth or division. The method includes: administering to the subject at least one cytotoxic agent, (e.g., a cytostatic agent, an agent that causes cell death), and at least one FGF antagonist, in an amount, which together, is effective (e.g., therapeutically or prophylactically) to reduce or inhibit the growth or division of, or induce the killing of, the unwanted cell. Preferably, the unwanted cell is the cell of an established tumor.

In a preferred embodiment, the FGF antagonist inhibits or reduces the FGF-induced resistance to a broad spectrum of cytotoxic agents, i.e., agents with diverse structures and mechanisms of action, including but not limited to, antimicrotubule agents, topoisomerase I inhibitors, topoisomerase II inhibitors, antimetabolites, mitotic inhibitors, alkylating agents, intercalating agents, agents capable of interfering with a signal transduction pathway (e.g., protein kinase C inhibitors, e.g., anti-hormones, e.g., antibodies against growth factor receptors), agents that promote apoptosis and/or necrosis, interferons, interleukins, tumor necrosis factors, and radiation.

In a preferred embodiment, the FGF antagonist comprises an inhibitor of bFGF.

In a preferred embodiment, the FGF antagonist comprises an inhibitor of aFGF.

In a preferred embodiment, the FGF antagonist includes at least one bFGF inhibitor and at least one aFGF inhibitor.

In a preferred embodiment, the aFGF inhibitor potentiates the action of the bFGF inhibitor.

In a preferred embodiment, the FGF antagonist acts extracellularly, e.g., inhibits the binding of an FGF molecule to its receptor.

In a preferred embodiment, the FGF antagonist acts intracellularly, e.g., interacts with the intracellular domain of the FGF receptor, inhibits the intracellular effects of FGF.

In a preferred embodiment, the FGF antagonist: is capable of binding to an FGF molecule or an FGF receptor; blocks the binding of FGF to a receptor; blocks the interaction of FGF with molecules that facilitate the binding of FGF to a receptor; and/or down regulates FGF receptor action. Preferably, the FGF molecule is bFGF and/or aFGF.

In a preferred embodiment, the FGF antagonist is other than suramin.

In a preferred embodiment, the FGF antagonist is other than an antibody, e.g., an antibody against FGF or an FGF receptor.

In a preferred embodiment, the FGF antagonist inhibits or reverses the resistance to anticancer drugs induced by FGF (e.g. aFGF and/or bFGF) in cultured tumor cells under in vitro conditions. The determination of effect on cultured cells can be determined using the system described in Example XV.

In a preferred embodiment, the FGF antagonist improves the efficacy of an agent, e.g., a cytotoxic agent, in the subject, relative to the effect of the cytotoxic agent in the absence of the FGF antagonist. Preferably, the FGF antagonist improves the efficacy of the cytotoxic agent against an established tumor.

In a preferred embodiment, the FGF antagonist is present in an amount sufficient to block FGF (e.g., bFGF and/or aFGF) action, but is not sufficient to cause one or more of: (i) significant inhibition of cell proliferation; (ii) significant cell death in human and/or animal tumor cells, (iii) a measurable antitumor effect in a subject, e.g., a human subject; and/or (iv) significant cell cycle arrest. The determination of effect on cultured cells can be determined with the system described in Example XV.

In a preferred embodiment, the FGF antagonist is administered at levels such that the plasma concentration of the FGF antagonist that is present when the cytotoxic agent is present in plasma at pharmacologically active concentration does not result in one or more of: (i) significant cell cycle arrest, (ii) significant cell death, or (iii) significant inhibition of cell growth, e.g., the concentration in plasma is of a level that if the same concentration of FGF antagonist is provided in cultured cells at least 10, more preferably at least 25, more preferably at least 50, more preferably at least 70, more preferably at least 80, more preferably at least 90, and most preferably at least 99% of the treated cultured cells continue to be involved in one or more of: (i) cycling cells continue to progress through the cell cycle, (ii) cells remain viable, or (iii) cells remain capable of proliferating, following treatment with the FGF antagonist. The determination of effect on cultured cells should be determined with the system described in Example XV.

In a preferred embodiment, the FGF antagonist is administered at levels that, although not resulting in significant cell cycle arrest, significant cell death, or significant inhibition of cell growth as described above, sensitizes the tumor cells to treatment with cytotoxic agents. Preferably the levels of FGF antagonist result in a significant inhibition of FGF-mediated chemoresistance, e.g., the resistance of tumor cells to cytotoxic agents that is mediated by FGF. Preferably the FGF antagonist inhibits at least 10, more preferably, at least 25, more preferably at least, 50, more preferably at least 70, more preferably at least 80, more preferably at least 90, and most preferably at least 99% of the FGF-mediated chemoresistance. The determination of effect on cultured cells can be determined with the system described in Example XV.

In a preferred embodiment, the time period over which the FGF antagonist is administered or over which the FGF antagonist is maintained at a therapeutic level, e.g., at a plasma concentration that is sufficient to enhance the cytotoxic effect of the cytotoxic agent, is less than 180, more preferably less than 90, more preferably less than 60, and most preferably less than 30 days.

In a preferred embodiment, the time period over which the FGF antagonist is administered or over which the FGF antagonist is maintained at a therapeutic level, e.g., at a plasma concentration that is sufficient to enhance the cytotoxic effect of the cytotoxic agent does not begin substantially earlier or end substantial later than the period over which the cytotoxic agent is administered or over which the cytotoxic agent is maintained at a therapeutic level.

In a preferred embodiment, the time period over which the FGF antagonist is administered or over which the FGF antagonist is maintained at a therapeutic level, e.g., at a plasma concentration that is sufficient to enhance the cytotoxic effect of the cytotoxic agent ends less than 180, more preferably less than 90, more preferably less than 60, and most preferably less than 30 days after the last day on which the cytotoxic agent is administered or the last day on which the cytotoxic agent is present at therapeutic levels.

In a preferred embodiment, the time period over which the FGF antagonist is administered or over which the FGF antagonist is maintained at a therapeutic level, e.g., at a plasma concentration that is sufficient to enhance the cytotoxic effect of the cytotoxic agent begins less than 180, more preferably less than 90, more preferably less than 60, and most preferably less than 30 days before the first day on which the cytotoxic agent is administered or the first day on which the cytotoxic agent is present at therapeutic levels.

In a preferred embodiment, the FGF antagonist: is a protein or a peptide; is an antibody, e.g., a monoclonal, a murine antibody or a human antibody, or an antigen-binding fragment thereof. Preferably, the monoclonal antibody is a human antibody. The antibodies can be of the various isotypes, including: IgG (e.g., IgG1, IgG2, IgG3, IgG4), IgM, IgA1, IgA2, IgD, of IgE. Preferably, the antibody is an IgG isotype. The antibodies can be full-length (e.g., an IgG1 or IgG4 antibody) or can include only an antigen-binding fragment (e.g., a Fab, F(ab')$_2$, Fv or a single chain Fv fragment).

In a preferred embodiment, the FGF antagonist: is a recombinant antibody, e.g., a chimeric or a humanized antibody, or an antigen binding fragment thereof, e.g., has a variable region, or at least a complementarity determining region (CDR), derived from a non-human antibody (e.g., murine), while the remaining portion(s) are human in origin.

In a preferred embodiment, the FGF antagonist is a fragment of the FGF molecule. Preferably, the FGF fragment competes with an FGF molecule for binding to the receptor.

In a preferred embodiment, the FGF antagonist is a small molecule, (e.g., is selected from a combinatorial library).

In a preferred embodiment, the FGF antagonist is chosen from those disclosed herein, e.g., suramin, structural analogs of suramin, anti-FGF antibodies, anti-FGF receptor antibodies, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), low molecular weight heparin, heparan sulfate, protamine sulfate, transforming growth factor beta, cyclosporin A, or RNA ligands for bFGF.

In a preferred embodiment, the FGF antagonist is heparin.

In a preferred embodiment, the FGF antagonist is low molecular weight heparin.

In a preferred embodiment, the FGF antagonist is heparan sulfate.

In a preferred embodiment, the FGF antagonist is an anti-FGF antibody.

In a preferred embodiment, the FGF antagonist is suramin.

In a preferred embodiment, the FGF antagonist is suramin and the suramin is present in a concentration that is sufficient to block the resistance to anticancer agents induced by FGF (e.g., bFGF and/or aFGF), but is not sufficient to produce one or more of: (i) significant inhibition of cell proliferation; (ii) significant cell death in human and/or animal tumor cells, (iii) a measurable antitumor effect in a subject, e.g., a human subject, and/or (iv) cell cycle arrest. The determination of effect on cultured cells can be determined with the system described in Example XV.

In a preferred embodiment, the FGF antagonist is suramin and it is administered at levels such that the plasma concentration of suramin that is present when the cytotoxic agent is present in plasma at pharmacologically active concentration does not result in one or more of: (i) significant cell cycle arrest, (ii) significant cell death, or (iii) significant inhibition of cell growth, e.g., the concentration in plasma is of a level that, if the same concentration of suramin is provided in cultured cells, at least 10, more preferably at least 25, more preferably at least 50, more preferably at least 70, more preferably at least 80, more preferably at least 90, more preferably at least 99, and most preferably at least 99% of the treated cultured cells continue to be involved in one or more of: (i) cycling cells continue to progress through the cell cycle, (ii) cells remain viable, or (iii) cells remain capable of proliferating, following treatment with suramin. The determination of effect on cultured cells can be determined with the system described in Example XV.

Preferably, suramin is administered in an amount that results in a concentration ranging from about 0.1 to 100 µg/ml, preferably about 1 to 85 µg/ml, more preferably, about 5 to 60 µg/ml, even more preferably, about 10 to 50 µg/ml, and most preferably, 15 to 45 µg/ml. The pharmacokinetics of suramin is characterized by a triphasic concentration decline, with half-lives of 5.5 hours, 4.1 days and 78 days. The total body clearance is 0.0095 liter/hour/m$^2$ (Jodrell et al (1994) *J Clin Oncol* 12:166-175). Based on pharmacokinetic principles, a person skilled in the art can calculate that an initial dose of approximately 240 mg/m$^2$ should be administered to the average patient to achieve plasma concentrations declining from about 90 µg/ml (63 µM) to about 18 µg/ml (13 µM) over 96 hours. The 96 hour duration is chosen as an example, as the plasma concentrations of many commonly used cytotoxic agents to be administered with suramin will have declined below their therapeutic levels at 96 hours. Similar calculations can be performed to identify the initial suramin dose to deliver the preferred suramin plasma concentrations over other desired treatment durations. Maintenance doses to adjust the plasma concentrations for later treatment cycles can be similarly calculated.

In a preferred embodiment, the total suramin exposure is preferably less than 800 µM-day over 96 hours, preferably less than 600 µM-day over 96 hours, preferably less than 500 µM-day over 96 hours, preferably less than 400 µM-day over 96 hours, preferably less than 300 µM-day over 96 hours, preferably less than 252 µM-day over 96 hours, preferably less than 200 µM-day over 96 hours, preferably less than 150 µM-day over 96 hours, preferably less than 100 µM-day over 96 hours, and most preferably less than 52 µM-day over 96 hours. The total suramin exposure, as expressed in µM-day, is a product of the drug plasma concentration in µM-day (e.g., the average micromolarity over 24 hours) and the treatment duration in days. For example, treatment of a subject with 13 µM of suramin for four days would result in a total drug exposure of 52 µM-day over 96 hours.

Preferably, suramin is administered in an amount that results in a plasma concentration of less than 100, preferably less than 80, preferably less than 50, preferably less than 25, more preferably less than 15, and most preferably less than 10 µM. Preferably, this plasma concentration is maintained for less than 20 days, preferably less than 15 days, preferably less than 12 days, preferably less than 10 days, more preferably less than 8 days, and most preferably less than 5 days beyond the time duration where therapeutic concentrations of a cytotoxic agent are maintained.

In a preferred embodiment the FGF antagonist is suramin and the time period over which the suramin is administered or over which the suramin is maintained at the plasma concentration sufficient to inhibit or reverse the FGF-mediated resistance or to enhance the efficacy of the cytotoxic agent is less than 180, more preferably less than 90, more preferably less than 60, and most preferably less than 30 days.

In a preferred embodiment, suramin is given immediately or within 3, 2, or 1 day before the administration of the cytotoxic agent, ending immediately after plasma concentrations of the cytotoxic agent are below the therapeutic level.

In a preferred embodiment, the FGF antagonist is suramin and the time period over which the suramin is administered or over which the suramin is maintained at the plasma concentration sufficient to inhibit or reverse the FGF-mediated resistance or to enhance the efficacy of the cytotoxic agent does not begin substantially earlier or end substantial later than the period over which the cytotoxic agent is administered or over which the cytotoxic agent is maintained at a therapeutic level.

In a preferred embodiment, the FGF antagonist is suramin and the time period over which the suramin is administered or over which the suramin is maintained at the plasma concentration sufficient to inhibit or reverse the FGF-mediated resistance or to enhance the efficacy of the cytotoxic agent ends less than 180, more preferably less than 90, more preferably less than 60, and most preferably less than 30 days after the last day on which the cytotoxic agent is administered or the last day on which the cytotoxic agent is present at therapeutic levels.

In a preferred embodiment, the FGF antagonist is suramin and the time period over which the suramin is administered or over which the suramin is maintained at the plasma concentration sufficient to inhibit or reverse the FGF-mediated resistance or to enhance the efficacy of the cytotoxic agent begins less than 180, more preferably less than 90, more preferably less than 60, and most preferably less than 30 days before the first day on which the cytotoxic agent is administered or the first day on which the cytotoxic agent is present at therapeutic levels.

Methods described herein use suramin to enhance the antitumor effect of a cytotoxic agent (e.g., agents described in Table 2), where the suramin dose is selected to deliver a plasma concentration of below 100 µg/ml, preferably below 75 µg/ml, most preferably below 50 µg/ml, in a mammal while the cytotoxic agent is present in plasma at a pharmacologically active concentration. The suramin dose is administered before, simultaneously with, or after the administration of the at least one anticancer agent. Animal trials presented herein show that treatment of mice with two weekly intravenous bolus suramin doses of 10 mg/kg for 3 weeks enhances the antitumor effect of anticancer drugs (e.g., paclitaxel, doxorubicin) but does not result in additional body weight loss. This dose is calculated to result in a plasma suramin concentration of about 10 μM (~14 μg/ml) at 72 hours after dose administration (see Example IX, Tables 4 and 5, FIG. 7). The methods of the art use high dose suramin, either alone or in combination with a cytotoxic agent, where for a human subject, maintenance of plasma suramin concentrations of between 150 to 300 μg/ml is needed to produce a measurable antitumor effect (Eisenberger et al (1995) *J Clin Oncol* 13:2174-2186). A typical suramin dosing schedule aimed at maintaining suramin plasma concentrations between 150 and 300 μg/ml consists of an initial administration of 2100 mg/m² over the first week with the subsequent doses repeated every 28 days for 6 months or longer; the subsequent doses are adjusted using the Bayesian pharmacokinetic method (Dawson et al (1998) *Clin Cancer Res* 4:37-44, Falcone et al (1999) *Cancer* 86:470-476). Moreover, the methods of the art for using suramin in combination with other cytotoxic agents often administer suramin at a more frequent schedule or a longer duration than the frequency and the treatment duration for the other cytotoxic agents. For example, in the combination of suramin and doxorubicin for the treatment of androgen-independent prostate cancer, the duration of doxorubicin treatment was up to 20 weeks whereas the duration of the suramin treatment was up to 45 weeks (Tu et al (1998) *Clin Cancer Res* 4:1193-1201). For example, in the combination of suramin and mitomycin C for the treatment of hormone-resistant prostate cancer, suramin was given weekly whereas mitomycin C was given only every 5 weeks (Rapoport et al (1993) *Ann Oncol* 4:567-573). At these doses and chronic treatments, suramin causes the following toxicity in a human patient: adrenal insufficiency, coagulopathy, peripheral neuropathy, and proximal muscle weakness (Dorr and Von Hoff, Cancer Chemotherapy Handbook, 1994, pp 859-866). The incidence and severity of these toxicities are positively related to cumulated dose and are minimized in the methods described herein.

In a preferred embodiment, the FGF antagonist is an anti-FGF antibody. Preferably, the anti-FGF antibody is present in a concentration that is sufficient to block the resistance to anticancer agents induced by FGF (e.g., bFGF and/or aFGF), but is not sufficient to produce one or more of: (i) significant inhibition of cell proliferation; (ii) significant cell death in human and/or animal tumor cells, (iii) a measurable antitumor effect in a subject, e.g., a human subject, and/or (iv) cell cycle arrest.

In a preferred embodiment, the FGF antagonist is an anti-FGF antibody and it is administered at levels such that the plasma concentration of the anti-FGF antibody that is present when the cytotoxic agent is present in plasma at pharmacologically active concentration does not result in one or more of: (i) significant cell cycle arrest, (ii) significant cell death, or (iii) significant inhibition of cell growth, e.g., the concentration in plasma is of a level that if the same concentration of the anti-FGF antibody is provided in cultured cells at least 10, more preferably at least 25, more preferably at least 50, more preferably at least 70, more preferably at least 80, more preferably at least 90, more preferably at least 99, and most preferably at least 99% of the treated cultured cells, continue to be involved in one or more of: (i) cycling cells continue to progress through the cell cycle, (ii) cells remain viable, or (iii) cells remain capable of proliferating, following treatment with the FGF antibody. The determination of effect on cultured cells can be determined with the system described in Example XV.

In a preferred embodiment, the FGF antagonist is an anti-FGF antibody and the time period over which the anti-FGF antibody is administered or over which the anti-FGF antibody is maintained at the plasma concentration sufficient to inhibit or reverse the FGF-mediated resistance or to enhance the efficacy of the cytotoxic agent is less than 180, more preferably less than 90, more preferably less than 60, and most preferably less than 30 days.

In a preferred embodiment, the FGF antagonist is an anti-FGF antibody and the time period over which the anti-FGF antibody is administered or over which the anti-FGF antibody is maintained at the plasma concentration sufficient to inhibit or reverse the FGF-mediated resistance or to enhance the efficacy of the cytotoxic agent does not begin substantially earlier or end substantial later than the period over which the cytotoxic agent is administered or over which the cytotoxic agent is maintained at a therapeutic level.

In a preferred embodiment, the FGF antagonist is an anti-FGF antibody and the time period over which the anti-FGF antibody is administered or over which the anti-FGF antibody is maintained at the plasma concentration sufficient to inhibit or reverse the FGF-mediated resistance or to enhance the efficacy of the cytotoxic agent ends less than 180, more preferably less than 90, more preferably less than 60, and most preferably less than 30 days after the last day on which the cytotoxic agent is administered or the last day on which the cytotoxic agent is present at therapeutic levels.

In a preferred embodiment, the FGF antagonist is an anti-FGF antibody and the time period over which the anti-FGF antibody is administered or over which the anti-FGF antibody is maintained at the plasma concentration sufficient to inhibit or reverse the FGF-mediated resistance or to enhance the efficacy of the cytotoxic agent begins less than 180, more preferably less than 90, more preferably less than 60, and most preferably less than 30 days before the first day on which the cytotoxic agent is administered or the first day on which the cytotoxic agent is present at therapeutic levels.

In a preferred embodiment, the method inhibits the proliferation of, or enhances the killing of, a hyperproliferative cell selected from the group consisting of a solid tumor cell, a soft-tissue tumor cell, a metastatic tumor cell, a leukemic tumor cell, and a lymphoid tumor cell.

In a preferred embodiment, the method inhibits the proliferation of, or enhances the killing of, a hyperproliferative cell in a fibrotic tumor.

In a preferred embodiment, the disorder is a cancer, e.g., a sarcoma, a carcinoma, an adenocarcinoma, a lymphoma, or a leukemia.

In a preferred embodiment, the disorder is a cancer which includes an established tumor.

In a preferred embodiment, the disorder is a cancer which includes a solid tumor.

In a preferred embodiment, the disorder is a cancer which includes a metastatic lesion.

In a preferred embodiment, the disorder is a cancer which includes a leukemia.

In a preferred embodiment, the disorder is a cancer which includes a lymphoma.

In a preferred embodiment, the disorder is a cancer, e.g., a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

In a preferred embodiment, the disorder includes a cancer which includes cells, e.g., tumor or metastatic cells, which form from a tissue where an FGF molecule is expressed, preferably at high levels, or cells that are in contact or exposed to aFGF, bFGF and/or FGF-producing cells or tissues.

In a preferred embodiment, the disorder includes a cancer which includes cells, e.g., metastatic cells, which form from a tissue of the breast, prostate, kidney, bladder, liver, lungs, lymph nodes, colon, rectum, skin, brain, pancreas, cervix, ovary, larynx, pharynx, oral mucosa, cancers of the head and neck, cancers of hematopoietic origin, or cancers of the lymphoid system.

In a preferred embodiment, the disorder is a cancer which includes an established tumor, e.g., a tumor that has been growing in a subject for at least one week, preferably two weeks, preferably one month, preferably two months, more preferably three months, more preferably six months, and most preferably longer than six months.

Preferably, an established tumor can be diagnosed clinically.

Preferably, an established tumor can be visualized on diagnostic media, e.g., an X-ray, a CAT scan, or MRI.

Preferably, an established tumor can be diagnosed by the detection of tumor markers, e.g., prostate specific antigen for prostate cancer, Her2/neu for certain breast cancers, CA 125 for ovarian cancer, or genetic alterations.

Preferably, an established tumor can be diagnosed by the detection of pathological changes, e.g., blood in sputum for lung cancer, blood in feces in colon cancer, blood in urine for bladder cancer, a lump in breasts for breast cancer, pain, or headache.

Preferably, an established tumor can be diagnosed by biochemical analysis of a patient sample, e.g., a patient's sputum, feces, urine, etc.

Preferably, an established tumor can be diagnosed by morphological analysis of cells derived from a subject, e.g., morphological abnormalities, abnormal nucleus-to-cytoplasmic ratios, abnormal tissue architecture, abnormal tissue organization, or abnormal tissue composition.

Preferably, an established tumor is one that is visible, palpable, or found during necropsy or autopsy.

In a preferred embodiment, the disorder includes a cancer, e.g., lung cancer, renal cancer, glioma, melanoma, or chemotherapy-refractory cancer, a metastatic cancer, which is chemoresistant, e.g., shows little or no significant response to chemotherapy.

In a preferred embodiment, the hyperproliferative cell is found in a benign lesion.

In a preferred embodiment, the disorder is selected from the group consisting of psoriasis, cysts, benign prostatic hyperplasia, and endometriosis.

In a preferred embodiment, the disorder is selected from the group consisting of benign hyperplastic diseases, e.g., oral papillomas, central giant cell granulomas of the mouth or pharynx, benign cementoblastomas of the oral cavity, oral plakia, gastric polyps, gastric adenomas, small intestinal adenomas, small intestinal granulomas, small intestinal papillomas, small intestinal oncocytomas, small intestinal Schwannomas, colonic polyps, colonic adenomas, Crohn's disease, hepatic adenoma, hepatic cirrhosis, biliary papillomatosis, pancreatic adenomas, pancreatic ductal hyperplasia, renal oncocytomas, renal papillomas, adenomas of the bladder, malakoplakia of the bladder, pseudosarcomas of the bladder, endometriosis, benign prostatic hyperplasia, erythroplasia of the penis, polyps and papillomas of the vulva, vagina, or cervix, endometrial polyps, adenomas, papillomas, or leimyomas, ovarian cysts, fibrocystic disease of the breast, lipoma of the breast, sclerosing adenosis, hemangioma, ductal hyperplasia of the breast, fibroadenomas, adenomyoepitheliomas, hamartoma, nevus of the skin, genodermatoses, fibrosis of the bone, fibrous dysplasia, chondrodysplasisa, sclerosing bone dysplasia, axial osteomalacia, fibrogenesis imperfecta, osteomas, osteoid osteomas, osteoblastomas, osteochondomas, enchondromas, chondromyxoid fibromas, chondroblastomas, synovial lipomas, adenomas of endocrine organs, goiter, Graves' disease, adrenal hyperplasia, adrenal adenomas, adrenal MEN I syndrome, adrenal myelolipomas.

In a preferred embodiment, the subject is a mammal, e.g., a human. E.g., the subject is a patient, e.g., a cancer patient. The subject can be a patient with non-small cell lung cancer, is treated with a combination of paclitaxel, carboplatin and an FGF antagonist, e.g., suramin, or with a combination of gemcitabine, cisplatin, and an FGF antagonist, e.g., suramin. The subject can be a patient with hormone refractory prostate cancer, who is treated with a combination of estramustine phosphate, taxotere and an FGF antagonist, e.g., suramin, or with a combination of doxorubicin, ketoconazole and an FGF antagonist, e.g., suramin. The subject can be a patient with metastatic breast cancer, who is treated with a combination of cyclophosphamide, doxorubicin, 5-fluorouracil and an FGF antagonist, e.g., suramin, or a combination of doxorubicin, taxotere and an FGF antagonist, e.g., suramin. The subject can be a patient with advanced breast cancer that overexpresses the HER2/neu oncogene, who is treated with a HER2/neu inhibitor (e.g., a HER2/neu antibody) and an FGF antagonist, e.g., suramin, with or without paclitaxel or cisplatin. The subject can be a patient with advanced or metastatic colorectal cancer, who is treated with a combination of irinotecan and an FGF antagonist, e.g., suramin. The subject can be a patient with advanced colon cancer, who is treated with a combination of 5-fluorouracil, leucovorin and an FGF antagonist, e.g., suramin.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and radiation.

In a preferred embodiment, the cytotoxic agent is selected from the group consisting of an antimicrotubule agent, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interleukin, a tumor necrosis factor, and radiation.

In a preferred embodiment, the cytotoxic agent is selected from the group consisting of an antimicrotubule agent, a mitotic inhibitor, an agent capable of interfering with a signal transduction pathway (e.g., a protein kinase C inhibitor, e.g., an anti-hormone, e.g., an antibody against growth factor receptors), an interleukin, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate=PALA,N-Phosphoracetyl-L-Asparate (PALA), pentostatin, N-Phosphoracetyl-L-Asparate=PALA, pentostatin, 5-azacitidine, 5-Aza-C, BCNU=Carmustine, 5-azacitidine, 5-Aza-5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU=Carmustine, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, Lupron, leuprolide (e.g., Lupron), ketoconazole, tamoxifen, goserelin (Zoledax), flutamide, 4'-cyano-3-(4-(e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (Docetaxel), topotecan, irinotecan hydrochloride=Camptosar, etoposide, mitoxantrone, daunorubicin, idarubicin, teniposide, amsacrine, (e.g., Docetaxel), topotecan, irinotecan hydrochloride (e.g., Camptosar), doxorubicin, etoposide, mitoxantrone, daunorubicin, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate=PALA, pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, carboplatin, oxaliplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluoromethyl) propionanilide, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere amsacrine, (e.g., Docetaxel), camptothecin, topotecan, irinotecan hydrochloride (e.g., Camptosar), etoposide, mitoxantrone, daunorubicin, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate=PALA, pentostatin, 5-azacitidine, 5-Aza-2'-deoxycytidine, adenosine arabinoside (Ara-A), idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), topotecan, irinotecan hydrochloride (e.g., Camptosar), etoposide, mitoxantrone, daunorubicin, idarubicin, teniposide, amsacrine, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon beta, interferon gamma, interleukin 2, interleukin 4, interleukin 12, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin-12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin-12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin-12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interleukin 2, interleukin 4, interleukin 12, and radiation.

In a preferred embodiment, the cytotoxic agent is: paclitaxel, interferon alpha, gemcitabine, fludarabine, irinotecan, carboplatin, cisplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, gemcitabine, fludarabine, irinotecan, carboplatin, cisplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, doxorubicin, epirubicin, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, doxorubicin, epirubicin, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, gemcitabine, fludarabine, irinotecan, taxotere, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is present in an amount equal to or lower than the one used in conventional chemotherapy. For example, for the combination of paclitaxel and carboplatin with an FGF antagonist, the dose of paclitaxel is equal to or below 225 mg/m$^2$, and the dose of carboplatin is chosen to achieve a total concentration-time product of equal to or below 6-7 mg/ml.min in previously untreated patients, or equal to or below 4-5 mg/ml.min in patients that have received chemotherapy previously; the treatment is repeated every 3 weeks. For example, for the combination of estramustine phosphate and taxotere with an FGF antagonist, the daily oral dose of estramustine is equal to or below 1400 mg, and the dose of taxotere is equal to or below 70 mg/M$^2$ over 1 hour; the treatment is repeated every 3 weeks. For example, for the combination of doxorubicin and ketoconazole with an FGF antagonist, the weekly dose of doxorubicin is equal to or below 20 mg/m$^2$ by 24 hr infusion, and the total daily oral dose of ketoconazole is equal to or below 1200 mg. For example, for the combination of cyclophosphamide, doxorubicin and 5-fluorouracil with an FGF antagonist, the dose of intravenous cyclophosphamide is equal to or below 500 mg/M$^2$, the dose of doxorubicin is equal to or below 50 mg/m$^2$, and the dose of 5-fluorouracil is equal to or below 500 mg/m$^2$; the treatment is repeated every 4 weeks (the 5-fluorouracil dose is given once per week for two weeks whereas the doses of doxorubicin and cyclophosphamide are given once every 4 weeks). For example, for the combination of Herceptin and cisplatin with an FGF antagonist, the Herceptin dose is equal to or below 250 mg on day 0, followed by 9 weekly doses of equal to or below 100 mg, and the cisplatin dose is equal to or below 75 mg/m$^2$ on days 1, 29, and 57. For example, for the combination of irinotecan with an FGF antagonist, the four weekly doses of irinotecan are equal to or below 125 mg/m$^2$; the treatment cycle is 4 weeks on and 2 weeks off. For example, for the combination of irinotecan with an FGF antagonist, the dose of irinotecan is 350 mg/m$^2$ every 3 weeks. For example, for the combination of 5-fluorouracil and leucovorin with an FGF antagonist, the five daily intravenous bolus doses of 5-fluorouracil are equal to or below 425 mg/m$^2$, and the five daily intravenous bolus doses of leucovorin are equal to or below 20 mg/m$^2$; the treatment cycle is 1 week on and 4 weeks off. For example, for the combination of gemcitabine and cisplatin with an FGF antagonist, the three weekly doses of gemcitabine are equal to or below 1000 mg/m$^2$, and the single cisplatin dose given on day 2 is equal to or below 100 mg/m$^2$; the treatment is repeated every 4 weeks.

In a preferred embodiment, the method further includes repeated dosages of the same, or a different cytotoxic agent.

In a preferred embodiment, the method further includes repeated dosages of the same, or a different FGF antagonist.

In a preferred embodiment, the cytotoxic agent and the FGF antagonist are administered at the same time or in overlapping time periods; the agent and the FGF antagonist are administered at different times; the agent is administered first and the FGF antagonist is administered subsequently; the FGF antagonist is administered first and the agent is administered subsequently.

In a preferred embodiment, the cytotoxic agent is administered systemically or locally. For example, the agent can be administered parenterally (e.g., subcutaneously, intravenously, intramuscularly, intraperitoneally, intradermally, intrathecally, etc.), intravesically (i.e., urinary bladder), intraprostatically, orally, nasally, rectally, topically, and/or transdermally.

In a preferred embodiment, the FGF antagonist is administered systemically or locally. For example, the FGF antagonist can be administered parenterally (e.g., subcutaneously, intravenously, intramuscularly, intraperitoneally, intradermally, intrathecally, etc.), intravesically (i.e., urinary bladder), intraprostatically, orally, nasally, rectally, topically, and/or transdermally.

In a preferred embodiment, the methods described herein further comprise monitoring the FGF levels (e.g., a-FGF and/or b-FGF) of a subject prior to or during treatment. Preferably, the amount of an FGF antagonist administered to the subject is determined based upon the levels of FGF present in the subject, e.g., low concentrations of FGF in the subject require decreased doses of the FGF antagonist to overcome the chemoresistance mediated by FGF.

In another aspect, the invention features, a method of treating a cell, e.g., inhibiting cell killing, or protecting the ability of a cell (e.g., a dividing cells, preferably, a rapidly dividing cell) to proliferate, e.g., a method of protecting a rapidly dividing cell, in a subject, from one or more of killing, inhibition of growth or division or other damage caused, e.g., by a cytotoxic agent (e.g., a cytostatic agent, e.g., an agent that causes cell death). The method includes: administering, to the subject, an effective amount of at least one FGF agonist, thereby treating the cell, e.g., protecting or reducing the damage to the dividing cell from said cytotoxic agent.

In a preferred embodiment, the cell is: a cell from a body surface or cavity, e.g., a cell of the gastrointestinal or esophageal tract; a hair follicle cell; a hematopoietic cell, e.g., a hematopoietic stem cell.

In a preferred embodiment, the cell is part of the lining of the gastrointestinal tract or the esophageal tract.

In a preferred embodiment, the method inhibits hair loss; inhibits weight loss; inhibits the loss of gastrointestinal function; inhibits the loss of hematopoiesis.

In a preferred embodiment, the method further includes administering at least one cytotoxic agent (e.g., a cytostatic agent, e.g., an agent that causes cell death), e.g., an antiproliferative agent, e.g., an anticancer drug, e.g. radiation, e.g., an interferon, e.g., an interleukin, e.g., a tumor necrosis factor, to said subject.

In a preferred embodiment the cytotoxic agent is other than radiation, e.g., is an administered compound.

In a preferred embodiment, the cytotoxic agent is a compound other than an antimetabolite.

In a preferred embodiment, the FGF agonist is administered orally, locally, e.g., topically, or ex vivo. For example, the FGF agonist can be applied topically to treat hair follicles. In other embodiments, the cell, e.g., a bone marrow cell, can be treated ex vivo.

In a preferred embodiment, the FGF agonist is administered locally to a site, e.g., gastrointestinal tract, bone marrow, or the skin.

In a preferred embodiment, the FGF agonist is directly injected into the bone marrow.

In a preferred embodiment, the FGF agonist is applied topically, e.g. externally to the scalp.

In a preferred embodiment, the application of the FGF agonist does not significantly result in absorption into systemic circulation, and/or does not significantly result in a blood or plasma concentration that is sufficient to increase the proliferation of a tumor cell in the subject.

In a preferred embodiment, the FGF agonist is administered to a subject by a method that does not result in significant systemic administration or significant systemic levels of the FGF agonist, e.g. does not result in an increase in FGF agonist blood levels that promotes the chemoresistance of the tumor. Systemic administration or levels of the FGF agonist can be evaluated by determining the level of the FGF agonist in the blood before and after its administration to a subject. These two levels can then be tested in vitro and compared for their effect on the antitumor effect mediated by a cytotoxic agent against tumor cells. Preferably the FGF agonist blood level after administration should increase the $IC_{50}$ of the cytotoxic agent by less than 30, preferably less than 20, preferably less than 10, preferably less than 5, and most preferably less than 1%, as compared to the $IC_{50}$ of the cytotoxic agent in the presence of the blood levels of the FGF agonist prior to administration of the FGF agonist to the subject. The determination of effect on cultured cells can be determined with the system described in Example XV.

In a preferred embodiment, the subject is a mammal, e.g., a human. E.g., the subject is a patient, e.g., a cancer patient. For example, the subject is a patient with non-small cell lung cancer, who is treated with a combination of two or more of: paclitaxel, carboplatin, or an FGF antagonist, e.g., suramin, or with a combination of two or more of: gemcitabine, cisplatin, or an FGF antagonist, e.g., suramin. For example, the patient is a patient with hormone refractory prostate cancer, who is treated with a combination of two or more of: estramustine phosphate, taxotere, or an FGF antagonist, e.g., suramin, or with a combination of two or more of: doxorubicin, ketoconazole, an FGF antagonist, e.g., suramin. For example, the patient is a patient with metastatic breast cancer, who is treated with a combination of two or more of: cyclophosphamide, doxorubicin, 5-fluorouracil, or an FGF antagonist, e.g., suramin. For example, the patient is a patient with advanced breast cancer that overexpresses the HER2/neu oncogene, who is treated with Herceptin and suramin, with or without paclitaxel or cisplatin. For example, the patient is a patient with advanced or metastatic colorectal cancer, who is treated with one or more of: irinotecan or an FGF antagonist, e.g., suramin. For example, the patient is a patient with advanced colon cancer, who is treated with a combination of two or more of: 5-fluorouracil, leucovorin, or an FGF antagonist, e.g., suramin.

In a preferred embodiment, the treatment protects said cell from an effect, e.g., a cytotoxic effect (e.g., cytostasis, e.g., cell kill, e.g., hair loss), of said cytotoxic treatment.

In a preferred embodiment, the FGF agonist comprises bFGF, aFGF, or bFGF and aFGF, or a fragment or an analog thereof. When bFGF and aFGF are given in combination, they may have an additive effect, preferably, a synergistic effect. The FGF agonist is administered in an amount that results in concentrations sufficient to protect said cell from an effect, e.g., a cytotoxic effect (e.g., cytostasis, e.g., cell kill, e.g., hair loss), of said cytotoxic treatment. Administration of the FGF agonist may be repeated to provide protection throughout the duration of said cytotoxic treatment and/or throughout the duration when the plasma concentrations of the cytotoxic agent remain sufficient to produce a cytotoxic effect.

In a preferred embodiment, the time period over which the FGF agonist is administered or over which the FGF agonist is maintained at a therapeutic level, e.g., a plasma concentration that is sufficient to protect cells from the cytotoxic effects of the cytotoxic agent, is less than 180, more preferably less than 90, more preferably less than 60, and most preferably less than 30 days.

In a preferred embodiment, the time period over which the FGF agonist is administered or over which the FGF agonist is maintained at a therapeutic level, e.g., a plasma concentration that is sufficient to protect cells from the cytotoxic effects of the cytotoxic agent, does not begin substantially earlier or end substantial later than the period over which the cytotoxic agent is administered or over which the cytotoxic agent is maintained at a therapeutic level.

In a preferred embodiment, the time period over which the FGF agonist is administered or over which the FGF agonist is maintained at a therapeutic level, e.g., plasma concentration that is sufficient to protect cells from the cytotoxic effects of the cytotoxic agent, ends less than 180, more preferably less than 90, more preferably less than 60, and most preferably less than 30 days after the last day on which the cytotoxic agent is administered or the last day on which the cytotoxic agent is present at therapeutic levels.

In a preferred embodiment, the time period over which the FGF agonist is administered or over which the FGF agonist is maintained at a therapeutic level, e.g., a plasma concentration that is sufficient to protect cells from the cytotoxic effects of the cytotoxic agent, begins less than 180, more preferably less than 90, more preferably less than 60, and most preferably less than 30 days before the first day on which the cytotoxic agent is administered or the first day on which the cytotoxic agent is present at therapeutic levels.

In a preferred embodiment, the FGF agonist: is a peptide, or a small molecule.

In a preferred embodiment, the FGF agonist is nonproteinaceous.

In a preferred embodiment, the cytotoxic agent used in the methods described herein is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and radiation.

In a preferred embodiment, the cytotoxic agent used in the methods described herein is selected from the group consisting of an antimicrotubule agent, a topoisomerase I inhibitor, a topoisomerase II inhibitor, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent used in the methods described herein is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors, an interferon, an interleukin, and a tumor necrosis factor.

In a preferred embodiment, the cytotoxic agent used in the methods described herein is selected from the group consisting of an antimicrotubule agent, a topoisomerase I inhibitor, a topoisomerase II inhibitor, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor.

In a preferred embodiment, the cytotoxic agent used in the methods described herein, is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (Zoladex), flutamide, 4'-cyano-3-(4-fluorophenylsulphonyl)-2-hydroxy-2-methyl-3'-(trifluoromethyl) propionanilide, anti-Her 2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent used in the methods described herein, is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), pyrazofurin, doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate=PALA, Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (Zoladex), flutamide, 4'-cyano-3-(4-fluorophenylsulphonyl)-2-hydroxy-2-methyl-3'-(trifluoromethyl) propionanilide, anti-Her 2/neu antibody (e.g., Herceptin), anti-CD20 (e.g., Rituxan), interferon alpha, interferon beta, interferon gamma, interleukin 2, interleukin 4, interleukin 12, and tumor necrosis factors.

In a preferred embodiment, the cytotoxic agent used in the methods described herein, is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (Zoladex), flutamide, 4'-cyano-3-(4-fluorophenylsulphonyl)-2-hydroxy-2-methyl-3'-(trifluoromethyl) propionanilide, anti-Her 2/neu antibody (e.g., Herceptin), anti-CD20 (e.g., Rituxan), interferon alpha, interferon beta, interferon gamma, interleukin 2, interleukin 4, interleukin 12, and tumor necrosis factors, and radiation.

In a preferred embodiment, the cytotoxic agent used in the methods described herein, is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, cisplatin, carboplatin, oxaliplatin, mitomycin C, BCNU (e.g., carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her 2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent used in the methods described herein, is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, cisplatin, carboplatin, oxaliplatin, mitomycin C, BCNU (e.g., carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (Zoladex), flutamide, 4'-cyano-3-(4-fluorophenylsulphonyl)-2-hydroxy-2-methyl-3'-(trifluoromethyl) propionanilide, anti-Her 2/neu antibody (e.g., Herceptin), anti-CD20 (e.g., Rituxan), interferon alpha, interferon beta, interferon gamma, interleukin 2, interleukin 4, interleukin 12, and tumor necrosis factors.

In a preferred embodiment, the cytotoxic agent is: paclitaxel, interferon alpha, gemcitabine, fludarabine, irinotecan, carboplatin, cisplatin, taxotere, doxorubicin, epirubicin, 5-fluororuacil, UFT, tamoxifen, goserelin, ketoconazole, anti-Her2/neu antibody (e.g., Herceptin), anti-CD20, leuprolide (Lupron) and flutamide.

In another aspect, the invention features, a pharmaceutical composition which includes at least one FGF antagonist, at least one cytotoxic agent (e.g., a cytostatic agent, e.g., an agent that causes cell death), and a pharmaceutically acceptable carrier, wherein said FGF antagonist is present in an amount effective to enhance the efficacy of the cytotoxic agent, in reducing or inhibiting the proliferation, or in enhancing the killing, of a hyperproliferative cell.

In a preferred embodiment, the pharmaceutical composition is packaged with directions to practice the methods described herein.

In a preferred embodiment, the pharmaceutical composition includes: an inhibitor of bFGF; an inhibitor of aFGF; or a bFGF inhibitor and an aFGF inhibitor.

In a preferred embodiment, the FGF antagonist inhibits or reverses the resistance to anticancer drugs induced by FGF (e.g. aFGF and/or bFGF) in cultured tumor cells under in vitro conditions. The determination of effect on cultured cells can be determined with the system described in Example XV.

In a preferred embodiment, the FGF antagonist inhibits or reduces the resistance of tumor cells to a broad spectrum of cytotoxic agents.

In a preferred embodiment, the FGF antagonist: is capable of binding to an FGF molecule or an FGF receptor; blocks the binding of FGF to a receptor; blocks the interaction of FGF to molecules that facilitate the binding of FGF to a receptor; down regulates FGF receptor action; is a protein or a peptide; is an antibody, e.g., a monoclonal, diabody, a murine antibody, a human antibody, a humanized or a chimeric antibody, or an antigen-binding fragment thereof, e.g., an Fab, $F(ab')_2$, Fv or a single chain Fv fragment; is a truncated FGF molecule, or a fragment thereof.

In a preferred embodiment, the FGF antagonist acts extracellularly, e.g., inhibits the binding of an FGF molecule to the extracellular domain of the FGF receptors.

In a preferred embodiment, the FGF antagonist acts intracellularly, e.g., inhibits the binding of an FGF molecule to the intracellular domain of the FGF receptors.

In a preferred embodiment, the FGF antagonist acts intracellularly, e.g., inhibits the intracellular effects of FGF.

In a preferred embodiment, the FGF antagonist acts extracellularly, e.g., inhibits the binding of an FGF molecule to its receptor.

In a preferred embodiment, the FGF antagonist is chosen from those disclosed herein, e.g., suramin, structural analogs of suramin, anti-FGF antibodies, anti-FGF receptor antibodies, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), low molecular weight heparin, heparan sulfate, protamine sulfate, transforming growth factor beta, cyclosporin A, or RNA ligands for bFGF.

In a preferred embodiment, the FGF antagonist is suramin.

In a preferred embodiment, the FGF antagonist is a fragment of the FGF molecule which competes with an FGF molecule for binding to the receptor; the FGF antagonist is a small molecule.

In a preferred embodiment, the FGF antagonist is a small molecule, is chosen from a combinatorial library.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and radiation.

In a preferred embodiment, the cytotoxic agent is selected from the group consisting of an antimicrotubule agent, a topoisomerase I inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an agent capable of interfering with a signal transduction pathway (e.g., a protein kinase C inhibitor, e.g., an anti-hormone, e.g., an antibody against growth factor receptors), an interferon, an interleukin, a tumor necrosis factor, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interferon, an interleukin, and radiation.

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an interleukin, a tumor necrosis factor, and radiation.

In a preferred embodiment, the cytotoxic agent is selected from the group consisting of an antimicrotubule agent, a mitotic inhibitor, an agent capable of interfering with a signal transduction pathway (e.g., a protein kinase C inhibitor, e.g., an anti-hormone, e.g., an antibody against growth factor receptors), an interleukin, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below.

Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), topotecan, irinotecan hydrochloride (e.g., Camptosar), etoposide, mitoxantrone, daunorubicin, idarubicin, teniposide, amsacrine, epirubicin, merbarone, piroxantrone hydrochloride, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon beta, interferon gamma, interleukin 2, interleukin 4, interleukin 12, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), camptothecin, topotecan, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interleukin 2, interleukin 4, interleukin 12, tumor necrosis factors, and radiation.

In a preferred embodiment, the cytotoxic agent is selected from those disclosed below. Exemplary cytotoxic agents include: paclitaxel, vincristine, vinblastine, vindesine, vinorelbin, taxotere (e.g., Docetaxel), spiromustine, geldenamycin, cytochalasins, depsipeptide, leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide, anti-Her2/neu antibody (e.g., Herceptin), anti-CD20 (e.g., Rituxan), interferon alpha, interferon beta, interferon gamma, interleukin 2, interleukin 4, interleukin 12, and radiation.

In a preferred embodiment, the cytotoxic agent is: paclitaxel, interferon alpha, gemcitabine, fludarabine, irinotecan, carboplatin, cisplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, gemcitabine, fludarabine, irinotecan, carboplatin, cisplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, doxorubicin, epirubicin, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, carboplatin, cisplatin, taxotere, 5-fluorouracil, UFT, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, interferon alpha, gemcitabine, fludarabine, irinotecan, taxotere, doxorubicin, epirubicin, 5-fluorouracil, UFT, tamoxifen, goserelin, ketoconazole, anti-Her2/neu antibody (e.g., Herceptin), anti-CD20, leuprolide (e.g., Lupron) and flutamide. In a preferred embodiment, the cytotoxic agent is: paclitaxel, interferon alpha, gemcitabine, fludarabine, irinotecan, carboplatin, cisplatin, taxotere, doxorubicin, epirubicin, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is: paclitaxel, gemcitabine, fludarabine, irinotecan, taxotere, tamoxifen, goserelin, ketoconazole, anti-Her2/neu antibody (e.g., Herceptin), anti-CD20, leuprolide (e.g., Lupron) and flutamide.

In a preferred embodiment, the cytotoxic agent is present at an amount equal to or lower than the one used in conventional chemotherapy.

In a preferred embodiment, the hyperproliferative cell is a cancer cell.

In a preferred embodiment, the hyperproliferative cell is found in a benign lesion.

In a preferred embodiment, the disorder is selected from the group consisting of psoriasis, cysts, benign prostatic hyperplasia, and endometriosis.

In a preferred embodiment, the disorder is selected from the group consisting of benign hyperplastic diseases, e.g., oral papillomas, central giant cell granulomas of the mouth or pharynx, benign cementoblastomas of the oral cavity, oral plakia, gastric polyps, gastric adenomas, small intestinal adenomas, small intestinal granulomas, small intestinal papillomas, small intestinal oncocytomas, small intestinal Schwannomas, colonic polyps, colonic adenomas, Crohn's disease, hepatic adenoma, hepatic cirrhosis, biliary papillomatosis, pancreatic adenomas, pancreatic ductal hyperplasia, renal oncocytomas, renal papillomas, adenomas of the bladder, malakoplakia of the bladder, pseudosarcomas of the bladder, endometriosis, benign prostatic hyperplasia, erythroplasia of the penis, polyps and papillomas of the vulva, vagina, or cervix, endometrial polyps, adenomas, papillomas, or leimyomas, ovarian cysts, fibrocystic disease of the breast, lipoma of the breast, sclerosing adenosis, hemangioma, ductal hyperplasia of the breast, fibroadenomas, adenomyoepitheliomas, hamartoma, nevus of the skin, genodermatoses, fibrosis of the bone, fibrous dysplasia, chondrodysplasisa, sclerosing bone dysplasia, axial osteomalacia, fibrogenesis imperfecta, osteomas, osteoid osteomas, osteoblastomas, osteochondomas, enchondromas, chondromyxoid fibromas, chondroblastomas, synovial lipomas, adenomas of endocrine organs, goiter, Graves' disease, adrenal hyperplasia, adrenal adenomas, adrenal MEN I syndrome, adrenal myelolipomas.

In another aspect, the invention features, a pharmaceutical composition which includes at least one FGF agonist, and a pharmaceutically acceptable carrier, wherein said FGF agonist is present in an amount effective to protect, or reduce the damage, a cell, e.g., a rapidly dividing cell, from said cytotoxic agent.

In a preferred embodiment, the pharmaceutical composition is packaged with directions to practice the methods described herein.

In a preferred embodiment, the FGF agonist comprises bFGF; aFGF; or bFGF and aFGF, or a fragment or an analog thereof.

In a preferred embodiment, the FGF agonist comprises bFGF, or a fragment or an analog thereof.

In a preferred embodiment, the FGF agonist: is a peptide, or a small molecule.

In a preferred embodiment the FGF agonist is nonproteinaceous.

In a preferred embodiment, the cell is: a cell from a body surface or cavity, e.g., a cell of the gastrointestinal or esophageal tract; a hair follicle cell; a hematopoietic cell, e.g., a hematopoietic stem cell.

In a preferred embodiment, the cell is a part of the lining of the gastrointestinal tract or the esophageal tract.

In another aspect, the invention relates to kits for carrying out the combined administration of the FGF antagonist/agonist with other cytotoxic agents. In one embodiment, the kit comprises an FGF antagonist/agonist formulated in a pharmaceutical carrier, and at least one cytotoxic agent, formulated, as appropriate, in one or more separate pharmaceutical preparations.

In a preferred embodiment, the kit includes directions to practice the methods described herein.

In another aspect, the invention features a vaccine comprising an FGF polypeptide, or a FGF receptor-derived polypeptide, or a fragment of a proteoglycan that facilitates the binding of FGF to its receptors, and a pharmaceutically acceptable carrier, in an amount effective to immunize a subject against a neoplastic disease. The immunization against the neoplastic disease can be partial or complete. Said vaccine can be used to treat a cancer patient, or to prevent one or more of: the occurrence of, recidivism of, and/or metastasis of, the neoplastic disease. For example, it could be administered to a patient who has had a tumor surgically removed, to prevent recurrence of the tumor.

In a preferred embodiment, the subject is a mammal, e.g., a human.

In a preferred embodiment, the subject is not a cancer patient.

In a preferred embodiment, the subject is a patient that is afflicted with an ailment caused by a benign hyperplasia of a normal tissue.

In a preferred embodiment, the subject is a patient, e.g., a cancer patient. For example, the subject can be a patient in remission, or a cancer patient undergoing treatment (e.g., conventional chemotherapy, alone or in combination, with the methods described herein). For example, the subject can be a patient with non-small cell lung cancer, treated with a combination of two or more of: paclitaxel, carboplatin or an FGF antagonist, e.g., suramin, or with a combination of two or more of: gemcitabine, cisplatin, or an FGF antagonist, e.g., suramin. The subject can be a patient with hormone refractory prostate cancer, who is treated with a combination of two or more of: estramustine phosphate, taxotere, or an FGF antagonist, e.g., suramin, or with a combination of two or more of: doxorubicin, ketoconazole, or an FGF antagonist, e.g., suramin. The subject can be a patient with metastatic breast cancer, who is treated with a combination of two or more of: cyclophosphamide, doxorubicin, 5-fluorouracil, or an FGF antagonist, e.g., suramin, or a combination of two or more of: doxorubicin, taxotere, or an FGF antagonist, e.g., suramin. The subject can be a patient with advanced breast cancer that overexpresses the HER2/neu oncogene, who is treated with a HER2/neu inhibitor (e.g., a HER2/neu antibody) and/or an FGF antagonist, e.g., suramin, with or without paclitaxel or cisplatin. The subject can be a patient with advanced or metastatic colorectal cancer, who is treated with one or more of: irinotecan or an FGF antagonist, e.g., suramin. The subject can be a patient with advanced colon cancer, who is treated with a combination of two or more of: 5-fluorouracil, leucovorin, or an FGF antagonist, e.g., suramin. The subject can be a patient that is in remission but is with a cancer that has a good likelihood to recur, e.g., adult leukemia, e.g., early disseminated prostate cancer.

In another aspect, the invention features, a method for evaluating the effectiveness of a compound, e.g., for treating a disorder, e.g., a proliferative disorder, e.g., a malignant disorder, or for protecting cells, e.g., from a cytotoxic agent. The method includes:

contacting the compound with an FGF, e.g., aFGF or bFGF; and evaluating the ability of the compound to inhibit or promote FGF activity, inhibition being correlated with effectiveness of treating a disorder, and promotion being correlated with cell protection.

In a preferred embodiment, the method further comprises testing the compound to determine if it can modulate, e.g., increase, the efficacy of an agent which kills cells or inhibits cell growth, e.g., an anticancer agent. This can be done by administering the compound and the agent, together or separately, to a test cell or organism.

In a preferred embodiment, the method further comprises testing the compound to determine if it can modulate, e.g., increase, the efficacy of an agent which kills cells or inhibits cell growth, e.g., an anticancer agent, in the presence of FGF (e.g., bFGF, and/or aFGF). This can be done by administering the compound, the agent and the FGF, together or separately, to a test cell or organism.

In a preferred embodiment, the method further comprises testing the compound to determine if it can protect cells from an agent that kills cells or inhibits cell growth, e.g., a cytotoxic or an anticancer agent. This can be done by administering both the compound and the agent, together or separately, to a test cell or organism.

In a preferred embodiment the method includes:

providing a cell, e.g., a cultured cell, a transformed cell, a cell from a cancer, or a test organism;

administering said compound to said cell (or test organism) and evaluating FGF activity, cell proliferation, cell death, or tumor growth, e.g., metastatic tumor growth.

In a preferred embodiment, the disorder is a cancer which includes a sarcoma, a carcinoma, an adenocarcinoma, a lymphoma, or a leukemia.

In a preferred embodiment, the disorder is a cancer which includes a solid tumor.

In a preferred embodiment, the disorder is a cancer which includes a leukemia.

In a preferred embodiment, the disorder is a cancer which includes a lymphoma.

In a preferred embodiment, the disorder is a cancer which includes a metastatic lesion.

In a preferred embodiment, the disorder includes a cancer which includes cells, e.g., metastatic cells, which form from a tissue where an FGF molecule is expressed, or cells that are in contact or exposed to aFGF, bFGF and/or FGF-producing cells or tissues.

In a preferred embodiment, the disorder includes a cancer which includes cells, e.g., metastatic cells, which form from a tissue of the breast, prostate, kidney, bladder, liver, lungs, lymph nodes, colon, rectum, skin, brain, pancreas, cervix, ovary, larynx, pharynx, oral mucosa, cancers of the head and neck, cancers of hematopoietic origin, or cancers of the lymphoid system.

In a preferred embodiment, the disorder is a cancer, e.g., a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

In a preferred embodiment, the disorder is selected from the group consisting of benign hyperplastic diseases, e.g., oral papillomas, central giant cell granulomas of the mouth or pharynx, benign cementoblastomas of the oral cavity, oral plakia, gastric polyps, gastric adenomas, small intestinal adenomas, small intestinal granulomas, small intestinal papillomas, small intestinal oncocytomas, small intestinal Schwannomas, colonic polyps, colonic adenomas, Crohn's disease, hepatic adenoma, hepatic cirrhosis, biliary papillomatosis, pancreatic adenomas, pancreatic ductal hyperplasia, renal oncocytomas, renal papillomas, adenomas of the bladder, malakoplakia of the bladder, pseudosarcomas of the bladder, endometriosis, benign prostatic hyperplasia, erythroplasia of the penis, polyps and papillomas of the vulva, vagina, or cervix, endometrial polyps, adenomas, papillomas, or leimyomas, ovarian cysts, fibrocystic disease of the breast, lipoma of the breast, sclerosing adenosis, hemangioma, ductal hyperplasia of the breast, fibroadenomas, adenomyoepitheliomas, hamartoma, nevus of the skin, genodermatoses, fibrosis of the bone, fibrous dysplasia, chondrodysplasisa, sclerosing bone dysplasia, axial osteomalacia, fibrogenesis imperfecta, osteomas, osteoid osteomas, osteoblastomas, osteochondomas, enchondromas, chondromyxoid fibromas, chondroblastomas, synovial lipomas, adenomas of endocrine organs, goiter, Graves=disease, adrenal hyperplasia, adrenal adenomas, adrenal MEN I syndrome, adrenal myelolipomas.

In a preferred embodiment, the compound is a protein or a peptide.

In a preferred embodiment, the compound is a chemical, e.g., a small molecule (e.g., a member of a combinatorial library).

In a preferred embodiment, the cytotoxic agent is selected from the group consisting of an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, or radiation.

In a preferred embodiment, the cytotoxic agent is chosen from those disclosed below. Exemplary cytotoxic agents include: paclitaxel, vincristine, vinblastine, vindesine, vinorelbin, taxotere (e.g., Docetaxel), topotecan, camptothecin, irinotecan hydrochloride (e.g., Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Asparate=PALA, N-Phosphoracetyl-L-Asparate (PALA), pentostatin, 5-azacitidine, 5-Aza-5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, leuprolide (e.g., Lupron), ketoconazole, tamoxifen, goserelin (Zoladex), flutamide, 4'-cyano-3-(4-fluorophenylsulphonyl)-2-hydroxy-2-methyl-3'-(trifluoromethyl) propionanilide, Herceptin, anti-CD20 (e.g., Rituxan), interferon alpha, interferon beta, interferon gamma, interleukin 2, interleukin 4, interleukin 12, tumor necrosis factors, and radiation.

In a preferred embodiment, the cytotoxic agent is: paclitaxel, interferon alpha, gemcitabine, fludarabine, irinotecan, carboplatin, cisplatin, taxotere, doxorubicin, epirubicin, 5-fluorouracil, UFT, tamoxifen, goserelin, a HER2/neu antibody (e.g., Herceptin), anti-CD20, leuprolide (Lupron) and flutamide.

In a preferred embodiment the cell is a rapidly dividing cell, a gastrointestinal cell, or a hair follicle cell, or a hematopoietic cell, e.g., a hematopoietic stem cell.

In another aspect, the invention features, a method of analyzing a sample, e.g., for the level of tumor resistance to anticancer agents. The method includes:

evaluating the level of one or more FGF genes or gene products, wherein an increase or decrease in the level of one or more FGF genes or gene products, relative to a control, indicates the presence of tumor resistance to anticancer agents.

In a preferred embodiment, the sample, e.g. a sample form a subject, is a sample of tissue having unwanted proliferation, e.g., a sample of a benign hyperplasic tissue, a sample from a primary tumor, a metastatic tumor, or a leukemia.

In a preferred embodiment, the expression of FGF genes or gene products is selected from the group consisting of bFGF, aFGF, TSC22, VEGF, GAFA1, GAFA2, GAFA3 (originally designated as FSC1, FSC2, FSC3 in the U.S. Provisional Application No. 60/137,345), and TFII-I.

In a preferred embodiment, the method is performed: on a sample from a mammal, a sample from a human subject; and a sample from a cancer patient; as part of therapeutic decision making; to determine if the individual from which the target FGF is taken should receive a drug or other treatment; to diagnose an individual for a disorder or for predisposition to resistance to treatment, to stage a disease or disorder.

In a preferred embodiment, the method further includes choosing a therapeutic modality, e.g., a particular anticancer treatment, e.g. a particular FGF antagonist, or a dosage thereof, based on the level of FGF expression.

In some embodiments, nucleic acid (or protein) from the cell or sample is analyzed on positional arrays, e.g., DNA-chip arrays. Accordingly, in preferred embodiments, the method further includes:

analyzing the sample by providing an array of a plurality of capture probes, wherein each of the capture probes is positionally distinguishable from other capture probes of the plurality on the array, and wherein each positional distinguishable capture probe includes a unique reagent e.g., an antibody or a nucleic acid probe which can identify an FGF gene or gene product;

hybridizing the sample with the array of capture probes, thereby analyzing the sample sequence.

In another aspect, the method includes a method of staging a disorder, e.g., a proliferative disorder, e.g., a benign hyperplastic disorder, e.g., a malignant disorder, in a subject. The method includes:

providing a sample, e.g., cancerous sample, e.g. a tissue, a bodily fluid, e.g., urine, blood, or CSF, a biopsy, from said subject;

evaluating the expression of one or more FGF genes, e.g., by contacting said cancerous sample with, a nucleic acid probe that selectively hybridizes to one or more FGF gene products;

wherein an increase in the level of said one or more FGF genes or gene products, relative to a control, indicates a stage in the disorder, e.g., the malignant disorder.

In a preferred embodiment the FGF genes or gene products are selected from the group consisting of bFGF, aFGF, TSC22, VEGF, GAFA1, GAFA2, GAFA3 (originally designated as FSC1, FSC2, FSC3 in the U.S. Provisional Application No. 60/137,345), and TFII-I.

In preferred embodiments the method is performed: on a sample from a mammal, a sample from a human subject; e.g., a sample of a patient suffering from a benign hyperplastic disorder, e.g., a sample from a cancer patient; to determine if the individual from which the target nucleic acid or protein is taken should receive a drug or other treatment; to diagnose an individual for a disorder or for predisposition to resistance to treatment, to stage a disease or disorder.

In a preferred embodiment, the method further includes choosing a therapeutic modality, e.g., a particular anticancer treatment, or a dosage thereof, based on the level of FGF expression.

In a preferred embodiment, the expression of an FGF gene is evaluated by evaluating the expression of a signal entity, e.g., a green fluorescent protein or other marker protein, which is under the control or an FGF gene control element e.g., promoter.

In some embodiments, nucleic acid (or protein) from the cell or sample is analyzed on positional arrays, e.g., DNA-chip arrays. Accordingly, in preferred embodiments the method further includes:

analyzing the sample by providing an array of a plurality of capture probes, wherein each of the capture probes is positionally distinguishable from other capture probes of the plurality on the array, and wherein each positional distinguishable capture probe includes a unique reagent, e.g., an antibody or a nucleic acid probe which can identify an FGF gene or gene product;

hybridizing the sample with the array of capture probes, thereby analyzing the sample sequence.

In another aspect, the invention features, a method of diagnosing a disorder, e.g., a proliferative disorder, e.g., a malignant disorder, e.g., a benign hyperproliferative disorder, in a subject. The method includes:

providing a sample e.g., a cancerous sample, e.g., a tissue, a bodily fluid (e.g., blood, urine, sputum, CSF), a biopsy, from said patient;

evaluating the expression of one or more FGF genes, e.g., by contacting said sample with, a nucleic acid probe that selectively hybridizes to one or more FGF genes, or an antibody that specifically binds to one or more FGF gene products; wherein an increase or decrease in the level of said one or more FGF genes or gene products, relative to a control, indicates the presence or absence of the disorder, e.g., the malignant disorder.

In a preferred embodiment, the FGF related genes or gene product is selected from the group consisting of bFGF, aFGF, TSC22, VEGF, GAFA1, GAFA2, GAFA3 (originally designated as FSC1, FSC2, FSC3 in the U.S. Provisional Application No. 60/137,345), and TFII-I.

In a preferred embodiment, the expression of an FGF gene is evaluated by evaluating the expression of a signal entity, e.g., a green fluorescent protein or other marker protein, which is under the control of or an FGF gene control element, e.g., promoter.

In some embodiments, nucleic acid (or protein) from the cell or sample is analyzed on positional arrays, e.g., DNA-chip arrays. Accordingly, in preferred embodiments the method further includes:

analyzing the sample by providing an array of a plurality of capture probes, wherein each of the capture probes is positionally distinguishable from other capture probes of the plurality on the array, and wherein each positional distinguishable capture probe includes a unique reagent, e.g., an antibody or a nucleic acid probe which can identify an FGF gene or gene product;

hybridizing the sample with the array of capture probes, thereby analyzing the sample sequence.

In another aspect, the invention features, a method for evaluating the efficacy of a treatment of a disorder, e.g., a proliferative disorder, e.g., a malignant disorder, in a patient, comprising:

providing a sample, e.g., a cancerous sample, e.g., a tissue, a bodily fluid (e.g., blood, urine, sputum, CSF), a biopsy, from said patient;

evaluating the expression of one or more FGF genes, e.g., by contacting said cancerous sample with, a nucleic acid probe that selectively hybridizes to one or more FGF genes, or an antibody that specifically binds to one or more FGF gene products;

wherein a change, e.g., decrease, e.g., increase, in the level of said one or more FGF genes or gene products in a sample obtained after treatment, relative to the level of expression before treatment, is indicative of the efficacy of the treatment of said disorder.

In a preferred embodiment, the method further includes choosing a therapeutic modality, e.g., a particular anticancer treatment, or a dosage thereof, based on the level of FGF expression.

In a preferred embodiment the FGF genes or gene product is selected from the group consisting of bFGF, aFGF, TSC22, VEGF, GAFA1, GAFA2, GAFA3 (originally designated as FSC1, FSC2, FSC3 in the U.S. Provisional Application No. 60/137,345), and TFII-I.

In a preferred embodiment, the expression of an FGF gene is evaluated by evaluating the expression of a signal entity, e.g., a green fluorescent protein or other marker protein, which is under the control or an FGF gene control element, e.g., promoter.

In some embodiments, the nucleic acid (or protein) from the cell or sample is analyzed on positional arrays, e.g., DNA-chip arrays. Accordingly, in preferred embodiments the method further includes:

analyzing the sample by providing an array of a plurality of capture probes, wherein each of the capture probes is positionally distinguishable from other capture probes of the plurality on the array, and wherein each positional distinguishable capture probe includes a unique reagent, e.g., an antibody or a nucleic acid probe which can identify an FGF gene or gene product;

hybridizing the sample with the array of capture probes, thereby analyzing the sample sequence.

In another aspect, the invention features, a method for evaluating the effectiveness of a treatment, e.g., the administration of a compound, for treating a disorder, e.g., a proliferative disorder, e.g., a malignant disorder. The method includes:

providing a cell, e.g., a cultured cell, a transformed cell, a cell from a cancer, or a test organism;

administering said treatment to said cell (or test organism) and evaluating the expression of one or more FGF genes, e.g., by contacting a sample from said cell (or test organism) with, a nucleic acid probe that selectively hybridizes to one or more FGF genes, or an antibody that specifically binds to one or more FGF gene products;

wherein a change, e.g., decrease, in the level of said one or more FGF genes or gene products in a sample given said treatment, e.g., relative to the level of expression without the treatment, indicative of the effectiveness of the compound for treating said disorder.

In a preferred embodiment the FGF genes or gene product is selected from the group consisting of bFGF, aFGF, TSC22, VEGF, GAFA1, GAFA2, GAFA3 (originally designated as FSC1, FSC2, FSC3 in the U.S. Provisional Application No. 60/137,345), and TFII-I.

In a preferred embodiment the expression of an FGF gene is evaluated by evaluating the expression of a signal entity, e.g., a green fluorescent protein or other marker protein, which is under the control or an FGF gene control element, e.g., promoter.

In some embodiments, nucleic acid (or protein) from the cell or sample is analyzed on positional arrays, e.g., DNA-chip arrays. Accordingly, in preferred embodiments the method further includes:

analyzing the sample by providing an array of a plurality of capture probes, wherein each of the capture probes is positionally distinguishable from other capture probes of the plurality on the array, and wherein each positional distinguishable capture probe includes a unique reagent, e.g., an antibody or a nucleic acid probe which can identify an FGF gene or gene product;

hybridizing the sample with the array of capture probes, thereby analyzing the sample sequence.

Other features and advantages of the invention will be apparent from the following detailed description, and from the claims.

BRIEF DESCRIPTION OF THE DRAWINGS

FIG. 2A shows the reversal of CM-induced resistance (detected as changes in proliferative activity of rat MAT-LyLu cells by measuring the changes in BrdU incorporation in treated samples relative to control samples) using a monoclonal antibody against aFGF or bFGF as indicated. The source of CM was lung histocultures for the aFGF experiment, and early monolayer lung cultures for the bFGF experiment. The study used four controls: no CM (left solid curves, open circles); addition of 5 μg/ml aFGF or bFGF antibody but no CM (inverted filled triangle, overlaps with the left control curve); addition of CM but no antibody (right solid curves, open square); addition of CM plus a nonspecific antibody, IgG (5 μg/ml, filled diamond, overlaps with the right CM-control curve). Dotted curves, from right to left, addition of aFGF or bFGF antibody concentrations of 0.05 μg/ml (filled circle); 0.1 μg/ml (filled square); 1 or 0.5 μg/ml (filled triangle); and 5 μg/ml (open inverted triangle). Similar results were found for doxorubicin (shown here), paclitaxel and 5-fluorouracil. Similar results were also found for human PC3 prostate tumor cells.

FIG. 2B shows (a) the reversal of the CM-induced resistance to doxorubicin by removing aFGF and/or bFGF via immunoprecipitation, and (b) the restoration of the resistance by reconstituting the FGF-immunoprecipitated CM using human recombinant proteins (0.16 ng/ml r-aFGF and/or 0.9 ng/ml r-bFGF). The study was performed using rat MAT-LyLu cells. The reversal in CM-induced resistance was detected by measuring the changes in BrdU incorporation in treated samples relative to control samples. The source of CM was lung histocultures for both aFGF and bFGF experiments. The study used two controls: no CM (left solid curves, empty circles); with CM (right solid curves, empty squares). Upper left: CM minus bFGF (filled square); CM minus aFGF plus r-aFGF (filled circles, overlaps with the right CM-control curve). Upper right: CM minus bFGF (filled square, overlaps with the left control curve); CM minus bFGF plus r-bFGF (filled circle, overlaps with the right CM control curve). Lower left: Both the CM minus aFGF and bFGF (filled square) and the CM minus aFGF and bFGF plus aFGF (filled circle) curves overlap with the left control curve. Lower center: CM minus aFGF and bFGF (filled square, overlaps with left control curve); CM minus aFGF and bFGF plus r-bFGF (filled circle). Lower right: CM minus aFGF and bFGF (filled square, overlaps with left control curve); CM minus aFGF and bFGF plus r-aFGF and r-bFGF (filled circle, overlaps with the right CM-control curve).

FIG. 7A shows the changes in tumor weight (depicted as experimental weight relative to initial weight) with respect to duration of treatment.

FIG. 7B shows the changes in the animal body weight with respect to duration of treatment.

DETAILED DESCRIPTION OF THE INVENTION

Figure 1:
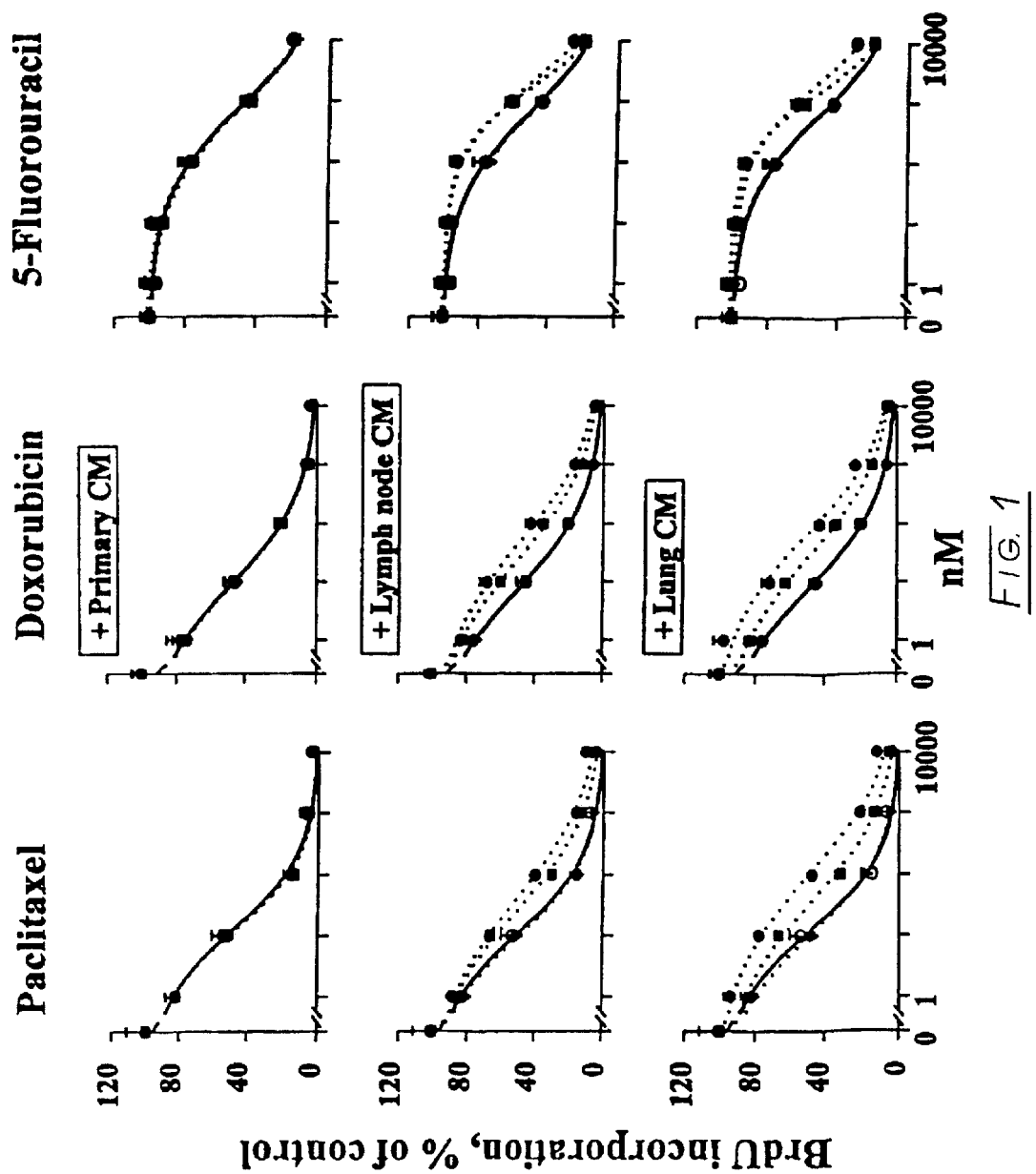
FIG. 1 depicts a panel of graphs showing the induction of resistance to paclitaxel, doxorubicin and 5-fluorouracil in monolayer cultures of rat MAT-LyLu tumor cells using conditioned medium (CM) collected from tumor cultures. The induction of drug resistance was detected as changes in proliferative activity by measuring the bromodeoxyuridine (BrdU) incorporation in treated samples relative to controls. Top panels: CM of primary tumors. Middle panels: CM of lymph node metastases. Bottom panels: CM of lung metastases. For each panel: control with no CM, (open circles); addition of histoculture CM (filled circle); addition of CM of early monolayer culture (passage 0, filled square); addition of CM of late monolayer culture (passage 3, filled inverted triangle). The curves for CM of primary tumor cultures and late monolayer metastatic tumor cultures overlap with the control curves. Similar results were obtained for human PC3 tumor cells.

The present invention is based, at least in part, on the discovery that bFGF induces broad spectrum resistance to anticancer agents, in a number of solid and soft-tissue tumors, metastatic lesions, as well as normal noncancerous intestinal epithelium. The bFGF-induced resistance was amplified by aFGF. In one embodiment, the invention shows that inhibitors of aFGF/bFGF enhanced the in vitro and in vivo activity of chemotherapy, resulting in shrinkage and eradication of well-established human lung metastasis and human subcutaneous xenograft tumors in mice. Accordingly, the present invention provides, in part, methods and compositions for inhibiting FGF-induced resistance to anticancer agents. In one embodiment, the FGF inhibitor is administered with other cytotoxic agents, e.g., an antimicrotubule agent, a topoisomerase I inhibitor, a topoisomerase II inhibitor, an antimetabolite, a mitotic inhibitor, an alkylating agent, an intercalating agent, an agent capable of interfering with a signal transduction pathway (e.g., a protein kinase C inhibitor, e.g., an anti-hormone, e.g., an antibody against growth factor receptors), an agent that promotes apoptosis and/or necrosis, an interferon, an interleukin, a tumor necrosis factor, and radiation. The enhanced, and sometimes synergistic, effect of the FGF inhibitor(s) (e.g., suramin, e.g., FGF antibody) with anticancer agents (e.g., paclitaxel, interferon alpha, gemcitabine, fludarabine, irinotecan, carboplatin, cisplatin, taxotere, doxorubicin, epirubicin, 5-fluorouracil, UFT, tamoxifen, goserelin, Herceptin, anti-CD20, leuprolide (Lupron) and flutamide), in addition to improving the efficacy of these anticancer agents, may allow for the administration of lower doses of these anticancer agents, thus reducing the induction of side effects in a subject, (e.g., a patient). For example, the subject is a patient with non-small cell lung cancer, who is treated with a combination of paclitaxel, carboplatin and suramin, or with a combination of gemcitabine, cisplatin, and suramin. For example, the patient is a patient with hormone refractory prostate cancer, who is treated with a combination of estramustine phosphate, taxotere and suramin, or with a combination of doxorubicin, ketoconazole and suramin. For example, the patient is a patient with metastatic breast cancer, who is treated with a combination of cyclophosphamide, doxorubicin, 5-fluorouracil and suramin. For example, the patient is a patient with advanced breast cancer that overexpresses the HER2/neu oncogene, who is treated with a Her2/neu antibody (e.g., Herceptin) and suramin, with or without paclitaxel or cisplatin. For example, the patient is a patient with advanced or metastatic colorectal cancer, who is treated with a combination of irinotecan and suramin. For example, the patient is a patient with advanced colon cancer, who is treated with a combination of 5-fluorouracil, leucovorin and suramin.

It is shown that the conditioned medium (CM) of solid, soft-tissue tumors, and metastatic tumors induced resistance to multiple anticancer agents, in human and rodent tumor cells. These CM contained elevated levels of aFGF and bFGF (see Examples II-III). Inhibition of bFGF using a bFGF-specific monoclonal antibody and removal of bFGF by immunoprecipitation resulted in complete reversal of the CM-induced resistance to anticancer agents, whereas inhibition/removal of aFGF resulted in partial reversal (see Example IV). Using CM that had been depleted of aFGF and/or bFGF and subsequently reconstituted with respective human recombinant proteins, bFGF but not aFGF was found to induce resistance aFGF was found to amplify the bFGF effect. aFGF and bFGF fully accounted for the CM effect, indicating these proteins are involved in the induction and maintenance of resistance to anticancer agents (see Example IV). The FGF-induced resistance was not due to reduced intracellular drug accumulation, nor altered cell proliferation (see Example XII), thus representing a novel epigenetic resistance mechanism.

It is shown that the elevated levels of aFGF and bFGF, as found in the active CM, induced broad spectrum resistance to at least 58 anticancer agents having different mechanisms of actions, including antitubulin/antimicrotubule agents, topoisomerase I inhibitors, topoisomerase II inhibitors, antimetabolites, alkylating agents, intercalating agents, agents that interfere with signal transduction pathways (e.g., protein kinase C inhibitors), and agents that promote apoptosis and/or necrosis (see Examples II and VII). aFGF/bFGF induction of resistance to paclitaxel (an antimicrotubule agent), doxorubicin (a topoisomerase I inhibitor) and 5-fluorouracil (an antimetabolite) was detected in multiple cancer cell lines derived from different human solid tumors, including prostate, lung, pharynx, colon and breast, as well as a human breast cancer cell line derived from stable transfection of the mdr1 gene encoding for the drug efflux protein, i.e., p-glycoprotein (see Example VIII). aFGF/bFGF also induced resistance of human leukemic cells to fludarabine (an antimetabolite) (see Example VIII).

It is further shown that inhibitors of FGF, including FGF antibodies and suramin, an inhibitor of multiple growth factors, including aFGF/bFGF, reverse the FGF-induced resistance and enhance the in vitro activity of anticancer agents, including at least 58 anticancer agents having different mechanisms of actions, including antitubulin/antimicrotubule agents, topoisomerase I inhibitors, topoisomerase II inhibitors, antimetabolites, alkylating agents, intercalating agents, agents that interfere with signal transduction pathways (e.g., protein kinase C inhibitors), and agents that promote apoptosis and/or necrosis (see Examples V and VII). The reversal of FGF-induced resistance was attained at suramin concentrations that do not produce measurable cytotoxicity under in vitro conditions (see Example VI). Under in vivo conditions, addition of suramin, at doses that do not produce measurable antitumor activity nor host toxicity, enhances the treatment efficacy of chemotherapy, resulting in shrinkage and eradication of well-established human lung metastases in mice and shrinkage of subcutaneous bulky human prostate xenograft in mice, without enhancing the host toxicity of chemotherapy (see Examples IX).

The appended examples further demonstrate that (a) presence of tumor cells enhanced the level of extracellular bFGF in host tissues, (b) bFGF level in tumors is determined by the location and the size of the tumor, and (c) bFGF level determines the sensitivity of human patient tumors to anticancer agents (see Example X). In addition, the appended examples show that treatment of human prostate cells with several anticancer agents with diverse structures and action mechanisms (e.g., antitubulin/antimicrotubule agents, topoisomerase I inhibitors, topoisomerase II inhibitors, alkylating agents, and antimetabolites) significantly enhanced the level of extracellular bFGF (see Example XI). Collectively, these examples indicate (a) the use of FGF gene expression and level to detect the presence of tumor cells, (b) the use of FGF expression and level in tumors to determine the extent of resistance, (c) the use of FGF gene expression and level in tumors to determine the dosage of the FGF inhibitors, and (d) that patients that are previously treated with chemotherapy are likely to exhibit chemoresistance. The latter indicates the need of using FGF inhibitors to treat patients who have failed cancer therapy and have recurrent tumors.

An appended example demonstrates that FGF antagonists, e.g., suramin, e.g., heparin, e.g., low molecular weight heparin, e.g., heparan sulfate, inhibit the binding of bFGF to its binding sites (Example XVI).

An additional appended example demonstrates that FGF agonists (e.g., aFGF, bFGF) reduced the toxicity of anticancer agents, e.g., paclitaxel and doxorubicin, to non-cancerous intestinal epithelium (Example XIV). Hence, the invention also provides methods and compositions for treating or preventing the undesired host toxicity of anticancer agents using aFGF and bFGF, alone or in combination.

In sum, the findings described herein demonstrate, inter alia, (a) a novel epigenetic mechanism by which cancer cells utilize the unique microenvironment of solid tumors and metastases to elude cytotoxic insult, (b) an important role of extracellular growth factors in tumor sensitivity to anticancer agents, (c) a new cancer treatment paradigm using combinations of anticancer agents with aFGF/bFGF inhibitors, (d) a novel mechanism and methods by which normal noncancerous host cells can be protected from the undesired toxicity of anticancer agents, and (e) methods to use the bFGF level for making therapeutic decision for individual patients.

Before further description of the invention, certain terms employed in the specification, examples and appended claims are, for convenience, collected here.

The terms peptides, proteins, and polypeptides are used interchangeably herein.

As used herein, the term "fibroblast growth factor" or "FGF" refers to a member of a family of polypeptides that are potent regulators of a variety of cellular processes including proliferation, differentiation, migration, morphogenesis, tissue maintenance and in wound healing and repair (Clarke et al. (1993) *J. Cell Sci.* 106: 121-133; Cuevas et al. (1988) *Biochem. Biophys. Res. Commun.* 156: 611-618; Burgess, W. H. and Maciag, T (1989) *Ann. Rev. Biochem.* 58: 575-606; Rifkin, D. B. and Moscatelli, D. (1989) *J. Cell Biol.* 109:1-6). The FGF family currently includes at least 19 structurally and functionally related proteins, including acidic and basic FGF, FGF-1 and FGF-2 respectively; int2 (FGF-3); hst (FGF-4); FGF-5; hst2 (FGF-6); keratinocyte growth factor (FGF-7); androgen-induced growth factor (FGF-8); glia-activating factor (FGF-9); FGF-10-19 (Galzie, Z. et al. (1997) *Biochem. Cell. Biol.*, 75:669-685; Yamasaki, M. et al. (1996) *J. Biol. Chem*, 271:15918-15921; Smallwood, P. M. et al. (1996) *Proc. Natl. Acad. Sci* USA, 93:9850-9857; McWhirter, J. R. et al. (1997) *Development,* 124:3221-3232; Hoshikawa, M. et al. (1998) *Biochem. Biophys. Res. Comm.,* 244:187-191; Hu, M. C. T. et al. (1998) *Mol. Cell. Biol.,* 18:6063-6074; and Nishimura, T. et al. (1999) *Biochim. Biophy. Acta,* 1444:148-151). Preferably, the term FGF refers to acidic and basic FGF, FGF-1 and FGF-2, respectively (reviewed in (Galzie, Z. et al. (1997) *Biochem. Cell. Biol.,* 75:669-685 and Burgess, W. H. and Maciag, T (1989) *Ann. Rev. Biochem.* 58: 575-606).

As used herein, the term "FGF receptor" or "FGFR" refers to FGF-binding polypeptides that possess intrinsic tyrosine kinase activity or heparan sulfate proteoglycans in the extracellular matrix. With respect to the tyrosine kinase receptors, there are currently four known genes encoding FGF receptors (FGFR-1, FGFR-2, FGFR-3, and FGFR-4), which can give rise to a variety of protein isoforms via alternative RNA splicing (Galzie, Z. et al. (1997) *Biochem. Cell. Biol.,* 75:669-685). The structure of the FGFR consists of an extracellular region with three immunoglobulin-like domains, a transmembrane region, and a cytosolic tyrosine kinase domain that is activated upon ligand binding. FGF binding causes dimerization of the receptors, resulting in receptor autophosphorylation on tyrosine residues and the activation of intracellular signal transduction cascades. The term "FGFR" also includes heparan sulfate proteoglycans in the extracellular matrix which mediate the actions of FGF, e.g., protection from proteolysis, localization, storage, and internalization of growth factors (Faham, S. et al. (1998) *Curr. Opin. Struct. Biol.,* 8:578-586). Heparan sulfate proteoglycans may serve as low affinity FGF receptors that act to present FGF to its cognate FGFR, and/or to facilitate receptor oligomerization (Galzie, Z. et al. (1997) *Biochem. Cell. Biol.,* 75:669-685).

As used herein, an "FGF antagonist" refers to an agent that inhibits (completely or partially) the activity, production, stability, of an FGF molecule. Preferably, the FGF antagonist acts extracellularly or intracellularly, e.g., inhibits the binding of an FGF molecule to an extracellular or intracellular domain of an FGF receptor, e.g., blocks the intracellular signaling initiated by activation of the FGF receptor. E.g., the inhibitor binds to the intracellular domain of the FGF receptor, or blocks a downstream action that is consequence of activation of the FGF receptor. In contrast, an "FGF agonist" refers to an agent that potentiates the activity, production, stability, of an FGF molecule, or activates FGF receptors.

As used herein, the term "specific inhibitor of FGF" refers to an FGF antagonist other than suramin.

As used herein, the terms "cytotoxic agent", "anticancer agent" and "antitumor agent" are used interchangeably herein and refer to agents that have the property of inhibiting the growth or proliferation (e.g., a cytostatic agent), or inducing the killing, of hyperproliferative cells. Preferably, the cytotoxic agent inhibits or reverses the development or progression of a neoplasm, such as a solid tumor, a soft tissue tumor, a metastatic lesion, a lymphoma, or a leukemia, or the cytotoxic agent inhibits or reverses the development or progression of a benign hyperplastic growth.

As used herein, a "therapeutically effective amount" of an FGF antagonist and a cytotoxic agent refers to an amount of such agents which in combination is effective, upon single- or multiple-dose administration to the subject, e.g., a patient, at inhibiting the growth or proliferation, or inducing the killing, of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment. As applied to FGF agonists, the phrase refers to an amount of such agent which is effective, upon single- or multiple-dose administration to protect a cell in a subject, e.g., a patient, from damage by an agent, e.g., a cytotoxic agent.

As used herein, "a prophylactically effective amount" of an FGF antagonist and a cytotoxic agent refers to an amount of such agents which in combination is effective, upon single or multiple dose administration to the subject, e.g., a patient, in preventing or delaying the occurrence of the onset or recurrence of a neoplastic disease state. As applied to FGF agonists, the phrase refers to an amount of such agent which is effective, upon single- or multiple-dose administration, in preventing or delaying damage to a cell in a subject, e.g., a patient, by an agent, e.g., a cytotoxic agent.

As used herein, the language "subject" is intended to include human and non-human animals. Preferred human animals include a human patient having a disorder characterized by the aberrant activity of a hyperproliferative cell. The term "non-human animals" of the invention includes all vertebrates, e.g., mammals and non-mammals, such as non-human primates, sheep, dog, cat, horse, cow, chickens, amphibians, reptiles, etc. Preferably, the subject is a human patient, e.g., a cancer patient, e.g., a patient with a benign hyperplastic disorder.

As used herein, "inhibiting the growth or proliferation" of the hyperproliferative cell, e.g., neoplastic cell, e.g., benign hyperplastic cell, refers to slowing, interrupting, arresting or stopping its growth and metastasis, and does not necessarily indicate a total elimination of the neoplastic growth.

As used herein, "inducing the killing" of the hyperproliferative cell, e.g., neoplastic cell, e.g., benign hyperplastic cell, refers to the partial or complete elimination of such cells, and does not necessarily indicate a total elimination of the neoplastic growth.

The terms "induce", "inhibit", "potentiate", "elevate", "increase", "decrease" or the like, denote quantitative differences between two states, refer to at least statistically significant differences between the two states. For example, "an amount effective to inhibit growth of hyperproliferative cells" means that the rate of growth of the cells will at least statistically significantly different from the untreated cells. Such terms are applied herein to, for example, rates of cell proliferation.

As used herein, the terms "hyperproliferative", "hyperplastic", "malignant", and "neoplastic" are used interchangeably, and refer to those cells in an abnormal state or condition characterized by rapid proliferation or neoplasm. The terms are meant to include all types of hyperproliferative growth, hyperplastic growth, cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth or in disease states characterized by benign hyperproliferative and hyperplastic cells.

The common medical meaning of the term "neoplasia" refers to "new cell growth" that results as a loss of responsiveness to normal growth controls, e.g., neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

As used herein, the terms "leukemia" or "leukemic cancer" refers to all cancers or neoplasias of the hemopoietic and immune systems (blood and lymphatic system). These terms refer to a progressive, malignant disease of the blood-forming organs, marked by distorted proliferation and development of leukocytes and their precursors in the blood and bone marrow. Myelolomas refer to other types of tumors of the blood, bone marrow cells. Lymphomas refer to tumors of the lymph tissue.

As used herein, the terms "immunoglobulin" and "antibody" refer to a glycoprotein comprising at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a target antigen). Examples of binding fragments encompassed within the term "antigen-binding portion" of an antibody include (a) a Fab fragment, a monovalent fragment consisting of the VL, VH, CL and CH1 domains; (b) a F(ab')$_2$ fragment, a bivalent fragment comprising two Fab fragments linked by a disulfide bridge at the hinge region; (c) a Fd fragment consisting of the VH and CH1 domains; (d) a Fv fragment consisting of the VL and VH domains of a single arm of an antibody, (e) a dAb fragment (Ward et al., (1989) *Nature* 341:544-546), which consists of a VH domain; and (f) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are encompassed within the term "antigen-binding portion" of an antibody. These antibody fragments are obtained using conventional techniques known to those with skill in the art, and the fragments are screened for utility in the same manner as are intact antibodies.

The term "monoclonal antibody" as used herein refers to an antibody molecule of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Methods for Inhibiting the Activity of Hyperproliferative Cells

In one aspect, this invention features methods for inhibiting the proliferation, and/or enhancing the killing of, hyperproliferative cells, by contacting the cells with at least one cytotoxic agent and at least one FGF antagonist. In general, the method includes a step of contacting pathological hyperproliferative cells with an amount of at least one cytotoxic agent and at least one FGF antagonist, which, in combination, is effective to reduce or inhibit the proliferation of the cell, or induce cell killing. The present method can be performed on cells in culture, e.g., in vitro or ex vivo, or can be performed on cells present in a subject, e.g., as part of an in vivo therapeutic protocol. The therapeutic regimen can be carried out on a human or on other animal subjects. The enhanced therapeutic effectiveness of the combination therapy of the present invention represents a promising alternative to conventional highly toxic regimens of anticancer agents.

While the FGF antagonists can be utilized alone, the subject methods are preferably combined with other anticancer agents, e.g., antimicrotubule agents, topoisomerase I inhibitors, topoisomerase II inhibitors, antimetabolites, mitotic inhibitors, alkylating agents, intercalating agents, agents capable of interfering with a signal transduction pathway (e.g., a protein kinase C inhibitor, e.g., an anti-hormone, e.g., an antibody against growth factor receptors), agents that promotes apoptosis and/or necrosis, an interferon, an interleukin, a tumor necrosis factor, and radiation. The enhanced, and sometimes synergistic, effect of the FGF inhibitor(s) (e.g., suramin, e.g., FGF antibody) with anticancer agents (e.g., paclitaxel, interferon alpha, gemcitabine, fludarabine, irinotecan, carboplatin, cisplatin, taxotere, doxorubicin, epirubicin, 5-fluorouracil, UFT, tamoxifen, goserelin, ketoconazole, Herceptin, anti-CD20, leuprolide (Lupron) and flutamide), in addition to improving the efficacy of these anticancer agents, may allow for the administration of lower doses of these anticancer agents, thus reducing the induction of side effects in a subject.

The subject method can be useful in treating malignancies of the various organ systems, such as those affecting lung, breast, lymphoid, gastrointestinal (e.g., colon), and genitourinary tract (e.g., prostate), pharynx, as well as adenocarcinomas which include malignancies such as most colon cancer, rectal cancer, renal cell carcinoma, prostate cancer and/or testicular tumors, non-small cell carcinoma of the lung, cancer of the small intestine and cancer of the esophagus. Exemplary solid tumors that can be treated include: fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The subject method may also be used to inhibit the proliferation or induce the killing of hyperplastic/neoplastic cells of hematopoietic origin, e.g., arising from myeloid, lymphoid or erythroid lineages, or precursor cells thereof. For instance, the present invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) Crit. Rev. Oncol./Hemotol. 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

The subject method may also be used to inhibit the proliferation or induce the killing of benign hyperplastic growth.

FGF Antagonists

The FGF antagonist used in the methods and compositions of the present invention can be a chemical, e.g., a protein or a peptide, or a small molecule. Preferably, the FGF antagonist is an inhibitor of bFGF, aFGF, or an inhibitor of both. For example, the FGF antagonist can be capable of binding to an FGF molecule, a molecule that facilitates the binding of FGF to a receptor, or an FGF receptor and, thereby, blocking the binding of an FGF molecule to a receptor (e.g., a tyrosine kinase receptor and/or a heparan sulfate proteoglycan). The FGF antagonist may also down regulate FGF receptor action, e.g., blocks the intracellular signalling initiated by activation of the FGF receptor. E.g., the inhibitor binds to the intracellular domain of the FGF receptor, or blocks a downstream action that is consequence of activation of the FGF receptor.

Examples of chemicals that may antagonize FGF action include suramin, structural analogs of suramin, pentosan polysulfate, scopolamine, angiostatin, sprouty, estradiol, carboxymethylbenzylamine dextran (CMDB7), suradista, insulin-like growth factor binding protein-3, ethanol, heparin (e.g., 6-O-desulfated heparin), low molecular weight heparin, protamine sulfate, cyclosporin A, or RNA ligands for bFGF. The FGF antagonist may also be a small molecule, e.g., a member of a combinatorial library.

A preferred FGF antagonist is suramin. Preferably, suramin is present in a concentration sufficient to block the resistance to anticancer agents induced by FGF (e.g., bFGF and/or aFGF), but is not sufficient to produce significant cytotoxicity (e.g., significant inhibition of cell proliferation, e.g., significant cell death) in human and/or animal tumor cells, not sufficient to cause significant cell cycle arrest, and/or not sufficient to produce measurable antitumor effect in a subject, e.g., a human subject. Preferably, suramin is administered in an amount that results in a plasma concentration ranging from about 0.1 to 100 microgram/ml, preferably about 1 to 85 microgram/ml, more preferably, about 5 to 60 microgram/ml, even more preferably, about 10 to 50 microgram/ml, and most preferably, 15 to 45 microgram/ml, of the plasma concentration.

Examples of proteins or peptide that may antagonize FGF activity include antibodies, e.g., a monoclonal antibody or an antigen fragment thereof, as described below. Alternatively, the FGF antagonist is a fragment of the FGF molecule. Preferably, the FGF fragment competes with an FGF molecule for binding to the receptor. The FGF antagonist may also be transforming growth factor beta or a fragment thereof.

Immunoglobulins

Examples of proteins or peptide that may antagonize FGF activity include antibodies, e.g., a monoclonal antibody, a murine antibody or a human antibody, or an antigen-binding fragment thereof. Preferably, the monoclonal antibody is a human antibody. For example, the human antibody can be produced by a hybridoma which includes a B cell obtained from a transgenic non-human animal, e.g., a transgenic mouse, having a genome comprising a human heavy chain transgene and a light chain transgene fused to an immortalized cell. The antibodies can be of the various isotypes, including: IgG (e.g., IgG1, IgG2, IgG3, IgG4), IgM, IgA1, IgA2, IgD, of IgE. Preferably, the antibody is an IgG isotype. The antibodies can be full-length (e.g., an IgG1 or IgG4 antibody) or can include only an antigen-binding fragment (e.g., a Fab, F(ab')$_2$, Fv or a single chain Fv fragment).

Several antibodies against bFGF and FGF are commercially available, and can be readily used in the methods and compositions of the invention. Examples of antibodies to bFGF that are commercially available include: (a) Sigma F 9666, anti-human, monoclonal, clone no. FA-88, host: mouse, type:IgG2a; (b) Sigma F 5521, polyclonal, host: rabbit; and (c) Oncogene PC316L, anti-bovine+anti-human, polyclonal, host: rabbit, type IgG.

Examples of antibodies to aFGF that are commercially available include: (a) Sigma F 6162, anti-human, monoclonal, clone no. FB-8, host: mouse, type: IgG1; (b) Sigma F 5537, anti-human, polyclonal, host: rabbit, type: IgG; (c) Sigma F 3393, anti-bovine, polyclonal, host: rabbit; (d) Oncogene PC15, anti-human, polyclonal, AB-1, host: rabbit, type: IgG; (e) Oncogene PC16, anti-human, polyclonal, AB-2, host: rabbit, type: IgG; (f) Oncogene GF22, anti-human, monoclonal, clone no. 3H3, AB-3, host: mouse, type: IgG1; (g) Oncogene GF23L, anti-human, monoclonal, clone no. 98, AB-4, host: mouse, type: IgG1; (h) Oncogene GF24, anti-human, monoclonal, clone no. 52, AB-5, host: mouse, type: IgG2b; and (i) Oncogene pC194L, anti-human, polyclonal, AB-6, host: goat, type: IgG.

Alternatively, the anti-FGF antibody can be made by methods known in the art. For example, an anti-FGF antibody can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed, e.g., viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. (1994) *Nature* 368:856-859; Green, L. L. et al. (1994) *Nature Genet.* 7:13-21; Morrison, S. L. et al. (1994) *Proc. Natl. Acad. Sci. USA* 91:6851-6855; Bruggeman et al. (1993) *Year Immunol* 7:33-40; Tuaillon et al. (1993) *Proc. Natl. Acad. Sci. USA* 90:3720-3724; Bruggeman et al. (1991) *Eur J Immunol* 21:1323-1326).

Monoclonal antibodies can also be generated by other methods known to those skilled in the art of recombinant-DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. (1989) *Proc. Natl. Acad. Sci. USA* 86:5728; Huse et al. (1989) *Science* 246: 1275; and Orlandi et al. (1989) *Proc. Natl. Acad. Sci. USA* 86:3833; Larrick et al. (1991), *Biotechniques* 11:152-156; Larrick et al. (1991), *Methods: Companion to Methods in Enzymology* 2:106-110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al.(1989) *Proc. Natl. Acad. Sci. USA* 86:3833-3837; Sastry et al. (1989) *Proc. Natl. Acad. Sci. USA* 86:5728-5732; and Huse et al. (1989) *Science* 246:1275-1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurjZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibody Hybridomas* 3:81-85; Huse et al. (1989) *Science* 246:1275-1281; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc Acid Res* 19:4133-4137; and Barbas et al. (1991) *Proc. Natl. Acad. Sci. USA* 88:7978-7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al. (1990) *Nature* 348:552-554, complete VH and VL domains of an antibody, joined by a flexible (Gly$_4$-Ser)$_3$ linker can be used to produce a single chain antibody which can render the display package separable based on antigen affinity. Isolated scFV antibodies immunoreactive with the antigen can subsequently be formulated into a pharmaceutical preparation for use in the subject method.

Once displayed on the surface of a display package (e.g., filamentous phage), the antibody library is screened with the target antigen, or peptide fragment thereof, to identify and isolate packages that express an antibody having specificity for the target antigen. Nucleic acid encoding the selected antibody can be recovered from the display package (e.g., from the phage genome) and subcloned into other expression vectors by standard recombinant DNA techniques.

Specific antibody molecules with high affinities for a surface protein can be made according to methods known to those in the art, e.g., methods involving screening of libraries (Ladner, R. C., et al., U.S. Pat. No. 5,233,409; Ladner, R. C., et al., U.S. Pat. No. 5,403,484). Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for VH and VL (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data. See for example Bajorath, J. and S. Sheriff, (1996) *Proteins: Struct., Funct., and Genet.* 24, 152-157; Webster, D. M. and A. R. Rees (1995) "Molecular modeling of antibody-combining sites" in S. Paul, Ed., Methods in *Molecular Biol.* 51, Antibody Engineering Protocols, Humana Press, Totowa, N.J., pp 17-49; and Johnson, G. et al. (1995) "Seqhunt: A program to screen aligned nucleotide and amino acid sequences," in *Methods in Molecular Biol* 51, op. cit., pp 1-15.

In one embodiment, a variegated peptide library is expressed by a population of display packages to form a peptide display library. Ideally, the display package comprises a system that allows the sampling of very large variegated peptide display libraries, rapid sorting after each affinity separation round, and easy isolation of the peptide-encoding gene from purified display packages. Peptide display libraries can be in, e.g., prokaryotic organisms and viruses, which can be amplified quickly, are relatively easy to manipulate, and which allows the creation of large number of clones. Preferred display packages include, for example, vegetative bacterial cells, bacterial spores, and most preferably, bacterial viruses (especially DNA viruses). However, the present invention also contemplates the use of eukaryotic cells, including yeast and their spores, as potential display packages. Phage display libraries are described above.

The term "modified" or "recombinant" antibody is also intended to include antibodies, such as monoclonal antibodies, chimeric antibodies, and humanized antibodies which have been modified by, e.g., deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies (i.e., chimeric antibodies) can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988) *Science* 240:1041-1043); Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L. (1985) *Science* 229:1202-1207 and by Oi et al. (1986) *BioTechniques* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A). The human CDRs may be replaced with non-human CDRs using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

Cytotoxic Agents

The FGF antagonist is preferably administered in combination with at least one cytotoxic agent. The term "in combination" in this context means that the agents are given substantially contemporaneously, either simultaneously or sequentially. If given sequentially, at the onset of administration of the second compound, the first of the two compounds is preferably still detectable at effective concentrations at the site where treatment effect is desired.

For example, the FGF antagonists can be used in combination therapy with conventional cancer chemotherapeutics. Conventional treatment regimens for leukemia and for other tumors include radiation, antitumor agents, interferons, interleukins, tumor necrosis factors, or a combination of two or more of these agents.

For example, the subject method may involve, in addition to the use of at least one FGF inhibitor, one or more other antitumor agents. Exemplary combination therapies include the use of such agents as, e.g., the ones described in Table 2 below, including but not limited to: antitubulin/antimicrotubule agents, e.g., paclitaxel, vincristine, vinblastine, vindesine, vinorelbin, taxotere (e.g., Docetaxel); topoisomerase I inhibitors, e.g., topotecan, camptothecin, irinotecan hydrochloride (e.g., Camptosar); topoisomerase II inhibitors, e.g., doxorubicin, etoposide, mitoxantrone, daunorubicin, idarubicin, teniposide, amsacrine, epirubicin, merbarone, piroxantrone hydrochloride; antimetabolites, e.g., 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-Phosphoracetyl-L-Aspartate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5'-deoxy-5-fluorouridine, tiazofurin; alkylating agents, e.g., cisplatin, carboplatin, oxaliplatin, mitomycin C, BCNU (e.g., Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via interfering with signal transduction pathway an/or yet-unknown action mechanisms, e.g., dihydrolenperone, spiromustine, geldanamycins, cytochalasins, depsipeptide; anti-hormones, e.g., leuprolide (e.g., Lupron), ketoconazole, tamoxifen, goserelin (e.g., Zoladex), flutamide, 4'-cyano-3-(4-fluorophenylsulphonyl)-2-hydroxy-2-methyl-3'-(trifluoromethyl) propionanilide; agents that inhibit the binding of a growth factor to a growth factor receptor, e.g., Herceptin, anti-CD20 (Rituxan); interferons, e.g., interferon alpha, interferon beta, interferon gamma; interleukins, e.g., interleukin 2, interleukin 4, interleukin 12; tumor necrosis factors; and radiation.

Examples of additional agents that can be used in combination with the FGF inhibitors include hydroxyurea, azathioprine, aminopterin, trimethoprin, pyrimethamine, pyritrexim, DDMP (2,4 diamino-5(3', dichlorophenyl)6 methylpyrimidine), 5,10-dideazatetrahydrofolate, 10-propargyl-5,8 dideazafolate (CB3717). 10-ethyl-10-deaza-aminopterin, deoxycytidine, 5-aza-cytosine arabinoside, N-4-palmitoyl-ara C, 2'-azido-2'-deoxy-ara C, N4-behenoyl-ara C, CCNU (lomustine), estramustine, MeCCNU, triethylene melamine, trenimon, dimethyl busulfan, streptozotocin, chlorozotocin, procarbazine, hexamethylmelamine (Altretamine pentamethylmelamine (PMM), tetraplatin, oxaliplatin, platinum-DACH, aziridinylbenzoquinone (AZQ), bleomycin, tallysomycin $S_{10}^b$, liblomycin, pepleomycin, asparaginase (Elspar), pegaspargase (Oncaspar), Cladrbine (leustatin), porfimer sodium (Photofrin), amonofide, deoxyspergualin, dihydrolenperone, flavone acetic acid, gallium nitrate, and hexamethylene bisacetamine (HMBA).

Particular combinations of cytotoxic agents can be used depending on the type of hyperproliferative disorder to be treated. For example, in addition to radiation, the following drugs, usually in combinations with each other, are often used to treat acute leukemias: vincristine, prednisone, methotrexate, mercaptopurine, cyclophosphamide, and cytarabine. In chronic leukemia, for example, fludarabine, busulfan, melphalan, and chlorambucil can be used in combination. In lung cancer, a combination of paclitaxel and carboplatin, or a combination of gemcitabine and cisplatin is used. In hormone refractory prostate cancer, a combination of estramustine phosphate and taxotere or a combination of doxorubicin and ketoconazole is used. For metastatic breast cancer, a combination of cyclophosphamide, doxorubicin and 5-fluorouracil is used. For advanced breast cancer that overexpresses the HER2/neu oncogene, a combination of an anti-Her2/neu antibody (e.g., Herceptin) and cisplatin is used. For advanced or metastatic colorectal cancer, a combination of 5-fluorouracil and leucovorin is used. All of the conventional anticancer drugs are highly toxic and tend to make patients quite ill while undergoing treatment; vigorous therapy is based on the premise that unless every cancer cell is destroyed, the residual cells will multiply and cause a relapse. Cytotoxic agents are also used to treat benign hyperplasia disorders. For example, psoriasis is treated with 5-fluorouracil.

Treatment can be initiated with smaller dosages that are less than the optimum dose of the agent. Thereafter, the dosage should be increased by small increments until the optimum effect under the circumstances is reached. For convenience, the total daily dosage may be divided and administered in portions during the day if desired. A therapeutically effective antitumor amount and a prophylactically effective antitumor amount of an FGF inhibitor or a cytotoxic agent is expected to vary from about 0.1 milligram per kilogram of body weight per day (mg/kg/day) to about 100 mg/kg/day.

Compounds which are determined to be effective for the prevention or treatment of tumors or for the prevention or treatment of benign hyperproliferative disorders in animals, e.g., dogs, rodents (e.g., see the Examples below), may also be useful in treatment of tumors in humans. Those skilled in the art of treating tumor in humans will know, based upon the data obtained in animal studies, the dosage and route of administration of the compound to humans. In general, the dosage and route of administration in humans is expected to be similar to that in animals, when adjusted for body surface area.

Determination of a therapeutically effective antitumor amount and a prophylactically effective antitumor amount of a FGF inhibitor and cytotoxic agent can be readily made by the physician or veterinarian (the "attending clinician"). The dosages may be varied depending upon the requirements of the patient, the severity of the condition being treated and the particular agent being employed. In determining the dose, a number of factors are considered by the attending clinician, including, but not limited to: the specific hyperplastic/neoplastic cell involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment; and other relevant circumstances. U.S. Pat. No. 5,427,916, for example, describes method for predicting the effectiveness of antineoplastic therapy in individual patients. In one embodiment, the present invention shows that the bFGF level determines the tumor sensitivity to anticancer agents, thus indicating the use of bFGF level in tumors for therapeutic decision making, including the selection of a therapeutic modality, e.g., a particular anticancer treatment, or a dosage thereof, based on the level of FGF expression.

Another aspect of the present invention accordingly relates to kits for carrying out the combined administration of the FGF antagonist/agonist with other therapeutic compounds. In one embodiment, the kit comprises an FGF antagonist/agonist formulated in a pharmaceutical carrier, and at least one cytotoxic agent, formulated as appropriate, in one or more separate pharmaceutical preparations.

Pharmaceutical Compositions

In another aspect, the present invention provides pharmaceutically acceptable compositions which comprise a therapeutically-effective amount of at least one FGF antagonist/agonist, formulated together with or without at least one cytotoxic agent, in a pharmaceutically acceptable carrier(s).

In a preferred embodiment, as described in detail below, the pharmaceutical compositions of the invention may be specially formulated for administration in solid or liquid form, including those adapted for the following: (a) oral administration, for example, drenches (aqueous or non-aqueous solutions or suspensions), tablets, boluses, powders, granules, pastes, mouthwash, hydrogels; (b) parenteral administration, for example, by subcutaneous, intramuscular or intravenous injection as, for example, a sterile solution or suspension; (c) intracavity administration, e.g., intraperitoneal instillation, intravesical (i.e., urinary bladder) instillation, intrathecal administration, (d) intraorgan administration, e.g., intraprostatical administration, (e) topical application, for example, as a cream, ointment or spray applied to the skin; (f) intravaginal or intrarectal administration, for example, as a pessary, cream, foam, enema, suppository; or (g) aerosol, for example, as an aqueous aerosol, liposomal preparation or solid particles containing the agent(s).

In vitro assays and animal studies as described in the Examples below, or an assay similar thereto (e.g., differing in choice of cells or animal used) can be used to determine an "effective amount" of the FGF antagonist/agonist and/or cytotoxic agent, or combinations thereof. The ordinarily skilled artisan would select an appropriate amount of each individual compound in the combination for use in the aforementioned assays or similar assays. Changes in cell activity or cell proliferation can be used to determine whether the selected amounts are "effective amount" for the particular combination of compounds. The regimen of administration also can affect what constitutes an effective amount. As described, FGF antagonist/agonist can be administered to the subject prior to, simultaneously with, or after the administration of the other cytotoxic agent(s). Further, several divided dosages, as well as staggered dosages, can be administered daily or sequentially, or the dose can be proportionally increased or decreased as indicated by the exigencies of the therapeutic situation.

The phrase "pharmaceutically acceptable" is employed herein to refer to those FGF antagonist/agonist and/or cytotoxic agent, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (a) sugars, such as lactose, glucose and sucrose; (b) starches, such as corn starch and potato starch; (c) cellulose, and its derivatives, such as sodium carboxymethyl cellulose, ethyl cellulose and cellulose acetate; (d) powdered tragacanth; (e) malt; (f) gelatin; (g) talc; (h) excipients, such as cocoa butter and suppository waxes; (i) oils, such as peanut oil, cottonseed oil, safflower oil, sesame oil, olive oil, corn oil and soybean oil; (j) glycols, such as propylene glycol; (k) polyols, such as glycerin, sorbitol, mannitol and polyethylene glycol; (l) esters, such as ethyl oleate and ethyl laurate; (m) agar; (n) buffering agents, such as magnesium hydroxide and aluminum hydroxide; (O) alginic acid; (p) pyrogen-free water; (q) isotonic saline; (r) Ringer's solution; (s) ethyl alcohol; (t) phosphate buffer solutions; and (u) other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (a) water soluble antioxidants, such as ascorbic acid, cysteine hydrochloride, sodium bisulfate, sodium metabisulfite, sodium sulfite and the like; (b) oil-soluble antioxidants, such as ascorbyl palmitate, butylated hydroxyanisole (BHA), butylated hydroxytoluene (BHT), lecithin, propyl gallate, alpha-tocopherol, and the like; and (c) metal chelating agents, such as citric acid, ethylenediamine tetraacetic acid (EDTA), sorbitol, tartaric acid, phosphoric acid, and the like.

Compositions containing the FGF antagonist/agonist and/or cytotoxic agent of the present invention may conveniently be presented in unit dosage form. The/amount of active ingredient which can be combined with a carrier material to produce a single dosage form will vary depending upon the host being treated, the particular mode of administration. Generally, out of one hundred percent, this dosage will range from about 1 percent to about ninety-nine percent of active ingredient, preferably from about 5 percent to about 70 percent, most preferably from about 10 percent to about 30 percent.

Compositions of the invention suitable for oral administration may be in the form of capsules, cachets, pills, tablets, lozenges (using a flavored basis, usually sucrose and acacia or tragacanth), powders, granules, hydrogels, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and/or as mouthwashes and the like, each containing a predetermined amount of a FGF antagonist/agonist and/or cytotoxic agent as an active ingredient. A compound may also be administered as a bolus, electuary or paste.

In solid dosage forms of the invention for oral administration (capsules, tablets, pills, dragees, powders, granules, hydrogels and the like), the active ingredient is mixed with one or more pharmaceutically-acceptable carriers, such as sodium citrate or dicalcium phosphate. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills, granules and hydrogels, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, nanoparticles, hydrogels, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the FGF antagonist/agonist and/or cytotoxic agent of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active FGF antagonist/agonist and/or cytotoxic agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more FGF antagonist/agonist and/or cytotoxic agent with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a FGF antagonist/agonist and/or cytotoxic agent include powders, sprays, ointments, pastes, creams, lotions, gels, solutions, patches and inhalants. The active FGF antagonist/agonist and/or cytotoxic agent may be mixed under sterile conditions with a pharmaceutically-acceptable carrier, and with any preservatives, buffers, or propellants which may be required.

The ointments, pastes, creams and gels may contain, in addition to FGF antagonist/agonist and/or cytotoxic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

The FGF antagonist/agonist and/or cytotoxic agent can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Transdermal patches have the added advantage of providing controlled delivery of a FGF antagonist/agonist and/or cytotoxic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral and/or intracavity administration comprise one or more FGF antagonist/agonist and/or cytotoxic agent in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable or implantable depot forms are made by forming matrices (e.g., microcapsules, e.g., cylinders, e.g., discs) of FGF antagonist/agonist and/or cytotoxic agent in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. Depot formulations can also be administered directly to tumor-bearing organs and/or cavity, e.g., urinary bladder, e.g., intraperitoneal cavity, e.g., intrathecally to brain tissue, to achieve localized delivery of FGF antagonist/agonist and/or cytotoxic agent.

The term "administration," is intended to include routes of introducing to a subject of the FGF antagonist/agonist and/or cytotoxic agent to perform their intended function. Examples of routes of administration which can be used include injection (subcutaneous, intravenous, parenterally, intraperitoneally, intrathecally, etc.), intravesically (i.e., urinary bladder), intraprostatically, oral, inhalation, rectal and transdermal. The pharmaceutical preparations are of course given by forms suitable for each administration route. For example, these preparations are administered in tablets or capsule form, by injection, inhalation, eye lotion, ointment, suppository, etc. The injection can be bolus or can be by continuous infusion. The FGF antagonist/agonist and/or cytotoxic agent can be administered alone, or in conjunction with either another agent as described above or with a pharmaceutically acceptable carrier, or both. The FGF antagonist/agonist and/or cytotoxic agent can be administered prior to the administration of the other agent, simultaneously with the agent, or after the administration of the agent. Furthermore, the FGF antagonist/agonist and/or cytotoxic agent can also be administered in a proform which is converted into its active metabolite, or more active metabolite in vivo.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a FGF antagonist/agonist and/or cytotoxic agent, such that it enters the patient's system and, thus, is subject to metabolism and other like processes.

Regardless of the route of administration selected, the FGF antagonist/agonist and/or cytotoxic agent, which may be used in a suitable hydrated form, and/or the pharmaceutical compositions of the present invention, are formulated into pharmaceutically-acceptable dosage forms by conventional methods known to those of skill in the art.

Vaccines

The present invention also concerns vaccines comprising an immunogenic amount of an FGF polypeptide, or a fragment thereof; an FGF receptor-derived polypeptide (FGFR polypeptide), or a fragment thereof, or a fragment of a proteoglycan (PG) that facilitates the binding of FGF to its receptors, dispersed in a physiologically acceptable, nontoxic vehicle, which amount is effective to immunize a subject, preferably a mammal, more preferably a human, against a neoplastic disease. The FGF or FGFR polypeptides, or the PG may be synthesized or prepared recombinantly or otherwise biologically, to comprise one or more amino acid sequences corresponding to one or more epitopes of the FGF or FGFR polypeptides, or the PG either in monomeric or multimeric form. Those polypeptides may then be incorporated into vaccines capable of inducing protective immunity. Techniques for enhancing the antigenicity of such polypeptides include incorporation into a multimeric structure, binding to a highly immunogenic protein carrier, for example, keyhole limpet hemocyanin (KLH), or diphtheria toxoid, and administration in combination with adjuvants or any other enhancers of immune response.

An amino acid sequence corresponding to an epitope of an FGF polypeptide either in monomeric or multimeric form may also be obtained by chemical synthetic means or by purification from biological sources including genetically modified microorganisms or their culture media. See Lerner, "Synthetic Vaccines", Sci. Am. 248(2): 66-74 (1983). The polypeptide may be combined in an amino acid sequence with other proteins/polypeptides including fragments of other proteins, as for example, when synthesized as a fusion protein, or linked to other antigenic or non-antigenic polypeptides of synthetic or biological origin. In some instances, it may be desirable to fuse an FGF or FGFR polypeptides, or the PG to an immunogenic and/or antigenic protein or polypeptide, for example, to stimulate efficacy of the vaccine.

The term "an epitope of an FGF or FGFR polypeptides, or the PG" will be understood to include the practical possibility that, in some instances, amino acid sequence variations of a naturally occurring protein or polypeptide may be antigenic and confer protective immunity against neoplastic disease and/or anti-tumorigenic effects. Possible sequence variations include, without limitation, amino acid substitutions, extensions, deletions, truncations, interpolations and combinations thereof. Such variations fall within the contemplated scope of the invention provided the polypeptide containing these variations is immunogenic and antibodies elicited by such a polypeptide cross-react with naturally occurring FGF polypeptides to a sufficient extent to provide protective immunity and/or anti-tumorigenic activity when administered as a vaccine. Such vaccine compositions can be combined with a physiologically acceptable medium, including immunologically acceptable diluents and carriers as well as commonly employed adjuvants such as Freund's Complete Adjuvant, saponin, alum, and the like. Administration would be in immunologically effective amounts of the FGF or FGFR polypeptides, or the PG, preferably in quantities providing unit doses of from 0.01 to 10.0 micrograms of immunologically active FGF or FGFR polypeptide, or the PG per kilogram of the recipient's body weight. Total protective doses may range from 0.1 to about 100 micrograms of antigen.

Routes of administration, antigen dose, number and frequency of injections are all matters of optimization within the scope of the ordinary skill in the art.

It will further be appreciated that anti-idiotype antibodies to FGF or FGFR polypeptide, or the PG are also useful as vaccines and can be similarly formulated.

EXAMPLES

The invention now being generally described, it will be more readily understood by reference to the following examples which are included merely for purposes of illustration of certain aspects and embodiments of the present invention, and are not intended to limit the invention.

The reagents and experimental protocols used in the appended examples are briefly described below.

Chemicals and Reagents

Mouse anti-human aFGF and bFGF monoclonal antibodies were obtained from Sigma; lactate dehydrogenase (LDH) assay, bromodeoxyuridine (BrdU) ELISA and human recombinant r-aFGF and r-bFGF from Boehringer Mannheim. The anti-aFGF antibody reacts with naturally occurring aFGF and human recombinant aFGF and does not cross-react with bFGF (Ichimori, Y. et al. (1991) *Biochem. Biophys. Res. Commun.* 175:291-297). The anti-bFGF antibody was generated using the 18 kDa human r-bFGF, is specific for bFGF and does not cross-react with aFGF (Watanabe, H. et al. (1991) *Biochem. Biophys. Res. Commun.* 175:229-235). r-aFGF and r-bFGF are monomeric peptides and are identical to the 14 kDa human aFGF or the 18 kDa human bFGF, except for the extra methionine at the amino terminus (Jaye, M. et al. (1986) *Science,* 233:541-545; Bohlen, P. et al. (1985) *FEBS Letters* 18:177-181).

Tumors and Cultures

Human prostate PC3 tumor cells and rat normal intestinal epithelial IEC6 cells were obtained from the American Type Culture Collection. The rat MAT-LyLu tumor cells and PC3-LN cells were obtained from Dr. John Isaacs and Dr. Joy Ware, respectively.

The original clone of the rat MAT-LyLu tumor cells, upon implantation in the hind limbs of male Copenhagen rats, yielded primary tumors at the implantation site and, as the primary tumor reaches a size equal to, or greater than, 0.5 g, metastasized initially in inguinal lymph nodes and subsequently in the lungs in 50% of animals (Isaacs, J. T. et al. (1981) *Invest. Urol.* 19:20-23). Using serial reimplantation of the lymph node and lung metastases, we obtained subclones that yielded more rapidly growing metastases in 100% of animals were obtained (n=24 for lymph node metastases and n=12 for lung metastases).

Paired primary and metastatic tumors were surgically removed from the same host. Fragments of the non-necrotic portions were cultured as histocultures. Single cell suspensions (>95% viability) were obtained by incubating tumor fragments (~1 g) with collagenase, EDTA, and trypsin. Histocultures (tumor fragments of ~1 mm$^3$) and monolayers were cultured in medium supplemented with 9% heat-inactivated fetal bovine serum (FBS) (Yen, W. C. et al. (1996) *Pharm. Res.* 13:1305-1312).

Collection and Analysis of Proteins in Conditioned Medium

Conditioned medium (CM) was collected from tumor histocultures (50 ml per 50 to 100 mg tumor fragments) and monolayer cultures (40 ml per 8×10$^7$ cells), after incubation in serum-free medium for 24 hours (Cavanaugh, P. G. & Nicolson, G. L. (1989) *Cancer Res.* 49:3928-3933). An aliquot of CM was concentrated 10,000-fold using lyophilization followed by reconstitution in 0.1 mM phenylmethylsulfonyl fluoride in water, and then analyzed on 15% SDS-PAGE (85 V for 2.5 hr). Protein bands were visualized with silver stain reagents. For Western blotting, proteins were transferred from polyacrylamide gel to a nitrocellulose filter by electrophoresis, followed by sequential incubation with 5% nonfat dry milk in 100 mM Tris/150 mM NaCl/0.1% Tween 20 (pH 7.6), and 5 microgram/ml aFGF or bFGF monoclonal antibody. The antibody-immunoreactive band was visualized using chemiluminescence blotting.

The levels of aFGF and bFGF in the concentrated CM were quantified by comparing the intensity of their bands on Western blots to the intensity of the bands derived from standard curve samples of r-aFGF and r-bFGF. The standard curves were linear between 3 and 100 ng r-aFGF and between 1 and 160 ng r-bFGF.

Pretreatment with CM and Recombinant r-bFGF/r-aFGF

Prior to drug treatment, cells were incubated for 4 days with tumor CM or with r-aFGF ad/or r-bFGF-containing medium, supplemented with 1% FBS (final protein concentration adjusted to 2 mg/ml). The medium was renewed every other day.

In vitro Antitumor Activity Evaluation

The antiproliferative drug effect in histocultures was measured as inhibition of $^3$H-thymidine incorporation quantified by autoradiography (Yen, W. C. et al. (1996) *Pharm. Res.* 13:1305-1312) and, for monolayers, as inhibition of BrdU incorporation or as reduction of total proteins by the sulforhodamine B assay (Au, J. L.-S. et al. (1998) *Cancer Res.* 58:2141-2148). For the latter, the two assays yielded qualitatively similar results. Cell kill induced by 96-hour drug treatment was monitored by the release of LDH into the culture medium. LDH activity was monitored by the conversion of tetrazolium to formazan (detected at 490 nm).

Removal of aFGF and bFGF from CM by Immunoprecipitation aFGF or bFGF was immunoprecipitated with their respective monoclonal antibody (1 microgram/ml), in the presence of Protein G PLUS/protein A agarose (Oncogene). This procedure reduced the bFGF level in the original CM to below the detection limit of 5 pg/ml by the ELISA (Oncogene), and the aFGF level in the concentrated CM to below the detection limit by Western blotting.

Example I

Contribution of Tumor Environment and Tumor Location to Resistance to Anticancer Agents This example describes three studies showing (a) a novel epigenetic mechanism of broad spectrum chemoresistance that is mediated by extracellular factors present in solid and metastatic tumors, and (b) loss of these factors upon removing tumors from metastatic sites and/or disrupting the tumor microenvironment. The results supporting these conclusions are provided in Table 1 below. The studies were performed using anticancer agents that have diverse structures and action mechanism, including paclitaxel (an antimicrotubule agent), doxorubicin (a topoisomerase II inhibitor) and 5-fluorouracil (an antimetabolite). Similar results were found for all three drugs.

The first study compared the chemosensitivity in histocultures of rat primary and metastatic tumors, where the heterogeneous cell types and the 3-dimensional structure of solid tumors are maintained, to the chemosensitivity in the corresponding monolayer cultures of cells obtained by trypsin-disaggregation of the same tumors. The 2- to 40-fold lower chemosensitivity in histocultures indicates that the unique environment in solid tumors played a role in chemoresistance. The second study shows that histocultures and early monolayer cultures of lung metastases were more resistant than lymph node metastases which in turn were more resistant than subcutaneous primary tumors, indicating that tumor location determined the extent of chemoresistance. The third study shows that monolayers derived from lung and lymph node metastases lost their chemoresistance after three passages and became equally sensitive to drugs as monolayers of primary tumor cells where chemosensitivity remained constant for all passages. This indicates a reversal of chemoresistance in metastatic tumors when cells were removed from the metastatic milieu.

TABLE 1

Loss of drug resistance, aFGF and bFGF upon disaggregation of metastatic tumors and upon passaging in monolayer cultures. Paired rat primary and metastatic tumors were cultured as histocultures or monolayers. For histocultures, tumors werre treated with paclitaxel for 24 hours (12 pairs of primary and lymph node tumors and 2 pairs of primary and lung tumors), and with doxorubicin (3 pairs of primary and lymph node tumors) and 5-fluorouracil (2 pairs of primary and lung tumors) for 96 hours. For monolayers, cells were treated with drugs for 96 hours, and drug effect was measured as inhibition of bromodeoxyuridine incorporation.

| | Concentration producing 50% inhibition | | | pg/ml in CM | |
|---|---|---|---|---|---|
| Culture conditions | Paclitaxel, nM | Doxorubicin, nM | 5-Fluorouracil, μM | aFGF | bFGF |
| Histocultures* | | | | | |
| Primary | >14 ± 5 | 18 ± 11 | 33 ± 12 | 62 ± 4 | 130 ± 13 |
| Lymph node | >227 ± 94† | 165 ± 66† | NM | 195 ± 23† | 660 ± 26† |
| Lung | >1804 ± 487† | NM | 122 ± 25† | 269 ± 12† | 845 ± 147† |
| Monolayers (passage 0) | | | | | |
| Primary | 10.7 ± 0.5 | 8.0 ± 0.5 | 0.79 ± 0.04 | 62 ± 7 | 93 ± 23 |
| Lymph node | 32.9 ± 3.6† | 31.0 ± 2.3† | 1.90 ± 0.06† | 100 ± 8† | 243 ± 39† |
| Lung | 92.4 ± 6.9† | 77.0 ± 2.9† | 2.84 ± 0.24† | 118 ± 13† | 302 ± 41† |
| Monolayers (passage 1) | | | | | |
| Primary | 10.5 ± 0.5 | 8.6 ± 0.5 | 0.85 ± 0.03 | NM | NM |
| Lymph node | 21.8 ± 0.9† | 17.9 ± 1.2† | 1.29 ± 0.06† | NM | NM |
| Lung | 28.1 ± 0.7† | 31.7 ± 8.9† | 1.52 ± 0.08† | NM | NM |

TABLE 1-continued

Loss of drug resistance, aFGF and bFGF upon disaggregation of metastatic tumors and upon passaging in monolayer cultures. Paired rat primary and metastatic tumors were cultured as histocultures or monolayers. For histocultures, tumors werre treated with paclitaxel for 24 hours (12 pairs of primary and lymph node tumors and 2 pairs of primary and lung tumors), and with doxorubicin (3 pairs of primary and lymph node tumors) and 5-fluorouracil (2 pairs of primary and lung tumors) for 96 hours. For monolayers, cells were treated with drugs for 96 hours, and drug effect was measured as inhibition of bromodeoxyuridine incorporation.

|  | Concentration producing 50% inhibition | | | pg/ml in CM | |
| --- | --- | --- | --- | --- | --- |
| Culture conditions | Paclitaxel, nM | Doxorubicin, nM | 5-Fluorouracil, μM | aFGF | bFGF |
| Monolayers (passage 2) | | | | | |
| Primary | 10.3 ± 0.8 | 8.0 ± 0.4 | 0.79 ± 0.06 | NM | NM |
| Lymph node | 15.0 ± 0.9† | 11.0 ± 0.4† | 1.09 ± 0.04† | NM | NM |
| Lung | 21.5 ± 3.7† | 16.6 ± 1.0† | 1.20 ± 0.04† | NM | NM |
| Monolayers (passage 3) | | | | | |
| Primary | 10.0 ± 0.2 | 8.0 ± 0.2 | 0.78 ± 0.04 | 54 ± 4 | 95 ± 9 |
| Lymph node | 11.7 ± 0.3 | 7.8 ± 0.5 | 0.83 ± 0.10 | 51 ± 3 | 89 ± 10 |
| Lung | 11.4 ± 0.7 | 8.0 ± 0.5 | 0.81 ± 0.04 | 58 ± 2 | 103 ± 12 |

NM, not measured.
*Inhistocultures, paclitaxel at 10,000 nM produced <50% inhibition, data shown are the concentrations that produced 30% inhibition.
†p < 0.05 for differences between primary and metastatic tumors, two-tailed Student's t-test.

Example II

Induction of Resistance to Anticancer Agents Due to Extracellular Factors in Solid and Metastatic Tumors This example describes the experiments confirming the induction of chemoresistance by extracellular factors in metastatic tumors, and indicating a progressive loss of these factors upon passaging metastatic tumor cells in monolayers.

CM from rat tumor cultures was collected and evaluated for its effect on chemosensitivity. This and subsequent experiments were performed using rat primary tumor cells and human prostate tumor cells. Qualitatively similar results were obtained for both cell types, indicating the general nature of the observations (FIG. 1). CM derived from histocultures and early monolayer cultures of metastases (referred to as active metastatic tumor CM) induced a 3- to 10-fold resistance to drugs (p<0.05), whereas CM from late monolayer cultures of metastatic tumors and CM from primary tumors (referred to as inactive CM) had no effect.

Example III

Identification of bFGF and aFGF as some of the Extracellular Factors that Induce Resistance to Anticancer Agents This example describes the experiments that show the presence of elevated concentrations of aFGF and bFGF in conditioned media (CM) from tumor cells.

The identity of the extracellular factors that cause tumor cells to become resistant to anticancer agents was established by comparing the proteins in the active and inactive CM (Table 1). Briefly, the active CM collected from histocultures of primary, lymph node and lung tumors and from early monolayer cultures (passage 0) of same tumors, were compared to the inactive CM collected from late monolayer cultures (passage 3) of same tumors. Immunoblotting was performed with mouse anti-human aFGF and bFGF antibodies. Control lanes with r-aFGF (20 ng) or r-bFGF (5 ng) were processed as a comparison.

The active CM showed 2- to 7-fold higher concentrations of two proteins, which were identified by immunoblotting as aFGF (approximately 14 kDa) and bFGF (approximately 18 kDa). Several observations suggest a cause-and-effect relationship between these proteins and resistance. First, the rank order of aFGF/bFGF concentrations in CM of different tumor culture systems was identical to the rank order of the chemoresistance in these cultures. Second, the progressive loss of these proteins upon passaging the metastatic tumors in monolayers coincided with the diminishing ability of these monolayer CM to induce chemoresistance. Third, as the protein levels in monolayers of metastatic tumors (passage 3) were reduced to the same levels as in monolayers of primary tumors, equal drug sensitivity was attained in both cultures. Fourth, in monolayer cultures, the aFGF/bFGF concentrations in CM significantly correlated with the relative chemoresistance (p<0.00011, Pearson test).

Example IV

Role of Extracellular aFGF and bFGF in Resistance to Anticancer Agents

This example describes six studies which collectively show that (a) extracellular aFGF and bFGF are involved in the induction and maintenance of broad spectrum resistance to anticancer agents; and (b) bFGF but not aFGF was required to induce resistance whereas aFGF amplified the bFGF effect.

Figure 2:
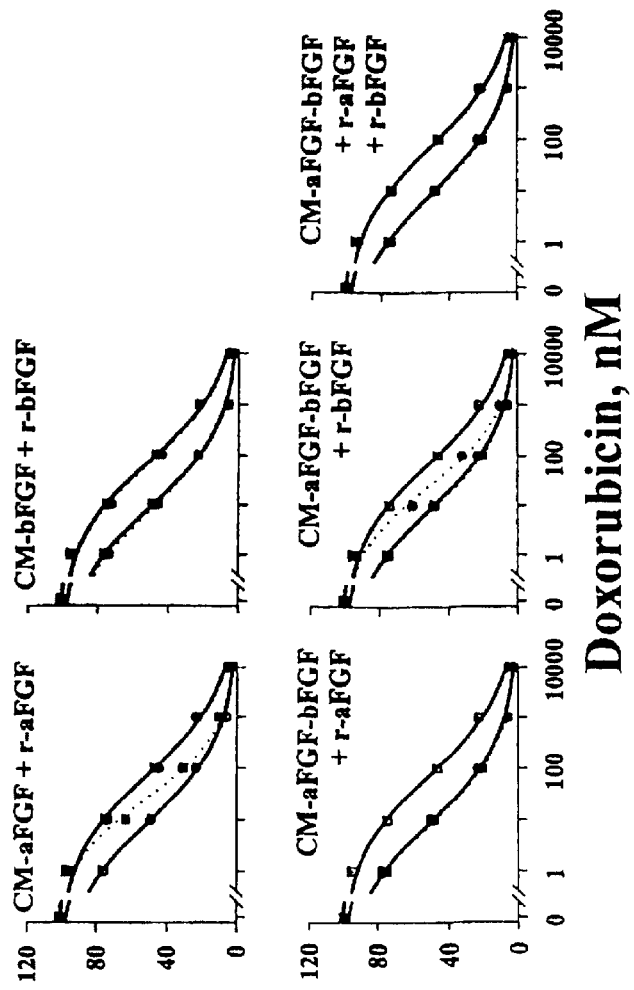
FIGS. 2A-2B depict a panel of graphs showing the reversal of CM-induced resistance by inhibiting or removing aFGF/bFGF.

The first study used specific inhibitors of extracellular aFGF and bFGF, i.e., monoclonal antibodies (FIG. 2A). In the absence of the active CM, treatment with antibodies to aFGF or bFGF did not alter drug activity, indicating no effect of the antibodies on the baseline chemosensitivity. In the presence of the active CM, the bFGF antibody produced a concentration-dependent reversal of the CM-induced chemoresistance, with complete reversal by 5 microgram/ml antibody, whereas a nonspecific antibody (i.e., non-immune rabbit IgG) had no effect. For aFGF, the antibody treatment partially reversed the CM-induced resistance; the maximum reversal was about 60% that was obtained with 1 microgram/ml antibody with no significant additional reversal at a 5-fold higher concentration. The second study evaluated the effect of removing aFGF and/or bFGF from the active CM by immunoprecipitation. Removal of bFGF abolished the resistance, whereas removal of aFGF only partially reversed the CM effect. These two studies indicate that both aFGF and bFGF were involved in the resistance, but had different roles.

Figure 3:
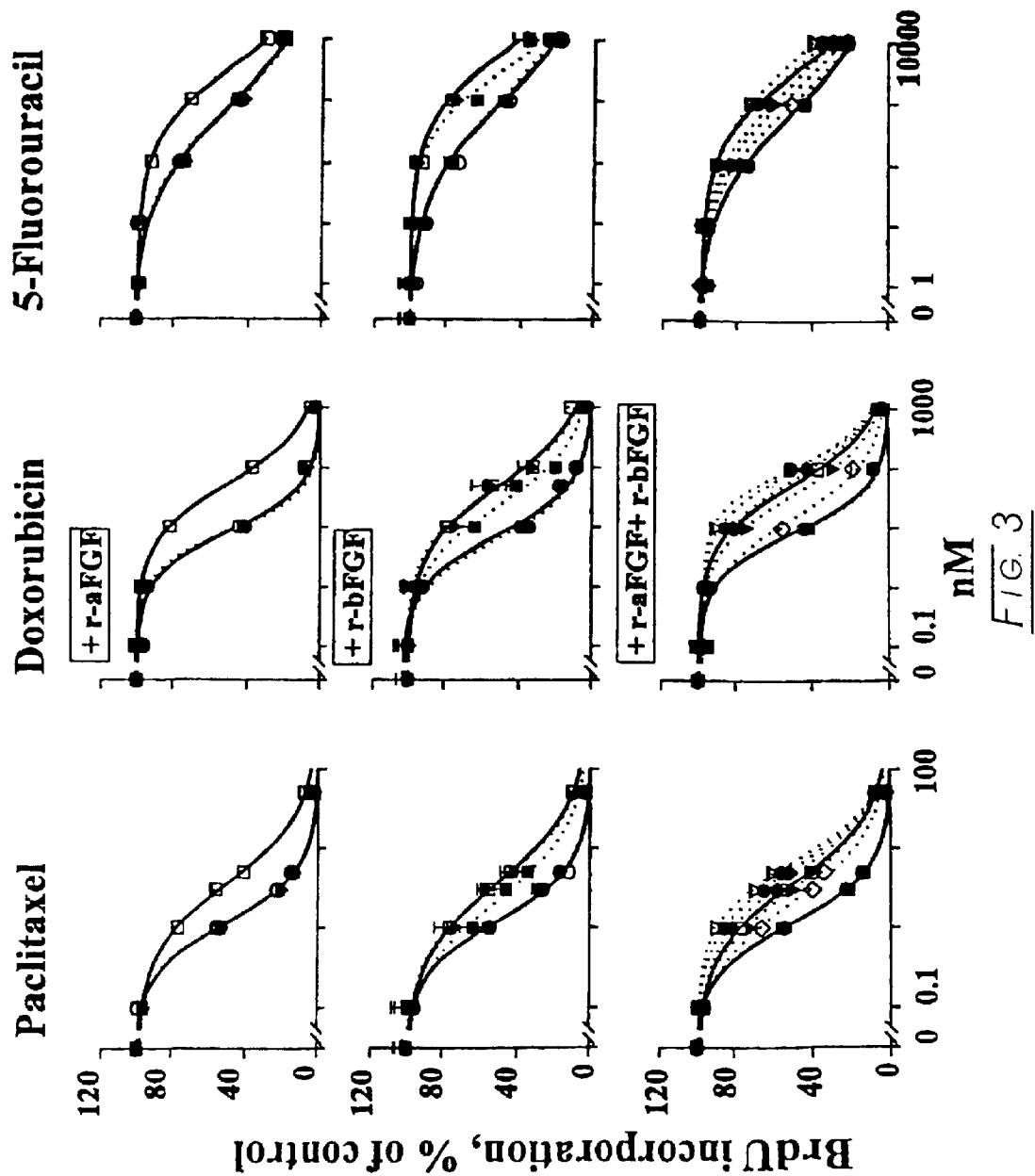
FIG. 3 is a panel of graphs showing induction of resistance to paclitaxel, doxorubicin and 5-fluorouracil in human prostate PC3 tumor cells using r-aFGF alone, r-bFGF alone or a combination of r-aFGF and r-bFGF, in the absence of CM. The study was performed using human prostate PC3 tumor cells (shown here) and rat MAT-LyLu tumor cells. The induction of resistance by FGF was detected by measuring the changes in BrdU incorporation in treated samples relative to control samples. The study used two controls: no CM (left solid curves, empty circles); with CM of lung histocultures (right solid curves, open squares). Top panels: addition of r-aFGF: 1 (filled circle), 10 (filled square) and 50 (filled inverted triangle) ng/ml. All three dotted curves overlap with the left control curve. Middle panels: addition of r-bFGF. Dotted curves from left to right: 1' (filled circle, overlaps with the left control curve), 10 (filled square) and 50 (filled inverted triangle, overlaps with the right CM-control curve) ng/ml. Bottom panels: addition of r-aFGF/r-bFGF combinations. Dotted curves from left to right: 0.04 and 1 ng/ml (filled square, overlaps with the left control curve); 0.08 and 1 ng/ml (open diamond); 0.16 and 1 ng/ml (filled inverted triangle); 0.32 and 1 ng/ml (filled diamond); 0.64 and 1 ng/ml (filled circle); and 1 ng/ml each (open inverted triangle). Similar results were obtained for rat MAT-LyLu tumor cells.

The third study determined whether aFGF and/or bFGF are required for the resistance. Endogenous aFGF and/or bFGF were removed from the active CM by immunoprecipitation, and then reconstituted the CM using recombinant proteins. When either the endogenous aFGF or bFGF were removed from the CM, addition of their respective recombinant counterparts, at concentrations comparable to the endogenous levels, fully restored the resistance (FIG. 2B). When both proteins were removed from the CM, (a) addition of r-aFGF did not induce resistance, whereas addition of r-bFGF produced a concentration-dependent resistance, indicating that bFGF but not aFGF was required for the resistance, and (b) the concentration of exogenous r-bFGF needed to restore the resistance was 55-fold higher than the endogenous bFGF concentration in the native CM or when endogenous aFGF was present (i.e., 50 ng/ml versus about 0.9 ng/ml). The latter finding suggests an amplification of bFGF effect by aFGF. This was confirmed in the fourth study, which shows a complete restoration of chemoresistance when the aFGF/bFGF-depleted CM was reconstituted with both r-aFGF and r-bFGF at physiological concentrations of the endogenous proteins. The fifth study confirmed that aFGF and bFGF were the main cause of chemoresistance, by using only r-aFGF and r-bFGF (i.e., without the immunoprecipitated CM) to induce resistance (FIG. 3). When given alone, r-aFGF had no effect whereas r-bFGF induced a concentration-dependent resistance. Combinations of r-aFGF/r-bFGF at concentrations as the endogenous proteins in the CM (i.e., between 0.16 and 0.32 ng/ml r-aFGF plus 1 ng/ml r-bFGF) produced the same extent of resistance as the CM, with an even greater resistance at higher protein concentrations.

Figure 4:
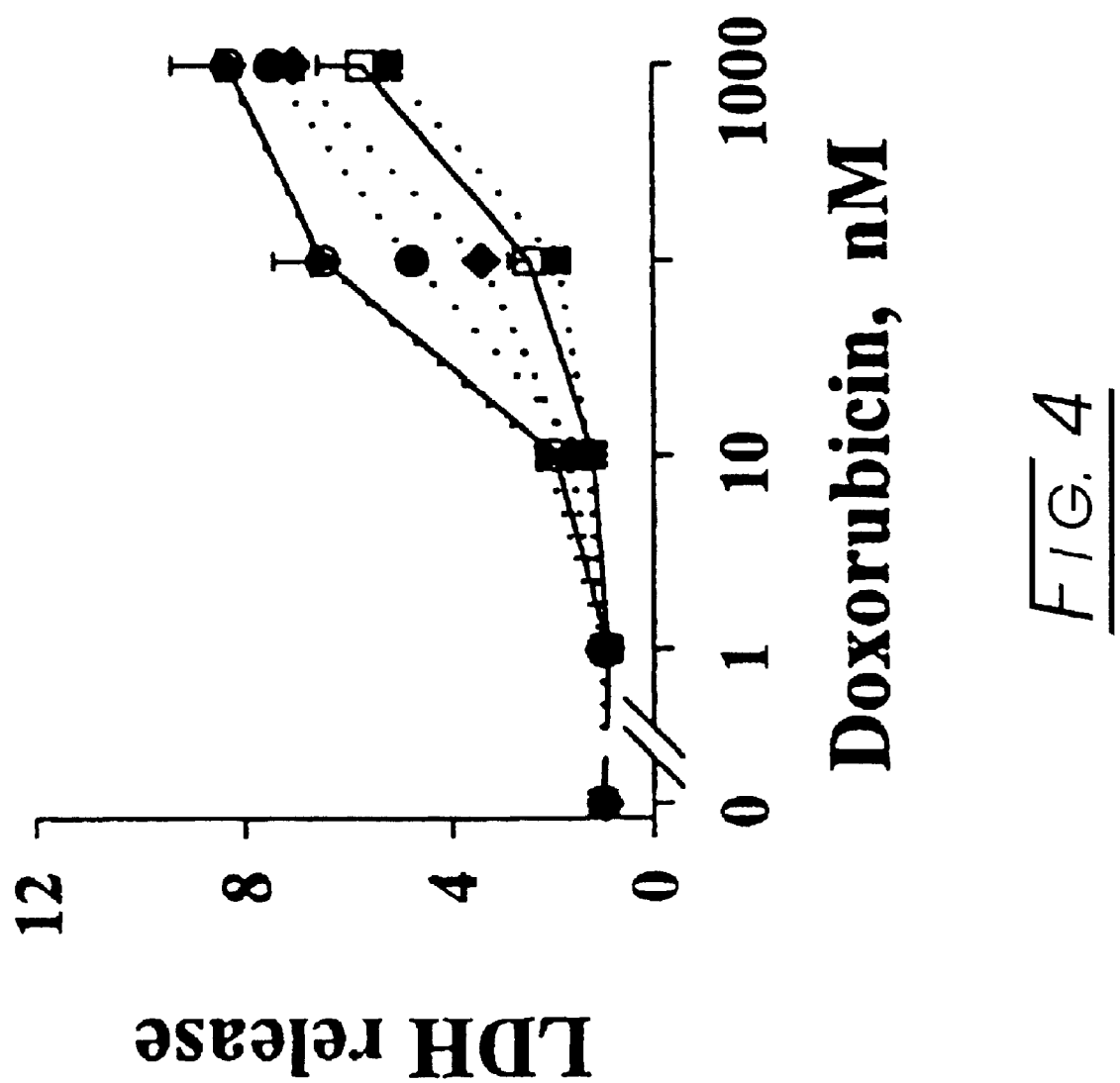
FIG. 4 is a graph depicting the FGF-induced resistance to cell kill caused by doxorubicin treatment. Drug-induced cell death in PC3 cells was monitored by the release of lactate dehydrogenase (LDH) to the culture medium. Results are expressed as a ratio of treated samples to untreated controls. Values for control samples varied by less than 10%. Curves from top to bottom: Without CM or FGF (open circle); addition of 0.9 ng/ml aFGF (filled inverted triangle, overlaps with top control curve); addition of 0.9 ng/ml bFGF (filled circle); addition of 0.16 ng/ml aFGF plus 0.9 ng/ml bFGF (filled diamond); CM of lung tumor histocultures (open square); 0.9 ng/ml aFGF plus 0.9 ng/ml bFGF (filled square). Similar results were found for paclitaxel, and 5-fluorouracil.

The chemoresistance observed above was measured primarily as antiproliferative drug effect. The sixth study measured the cell kill effect of drugs. Similar findings were observed, i.e., the active metastatic tumor CM and r-bFGF induced resistance to cell kill by drugs, whereas r-aFGF did not induce resistance but enhanced the effect of r-bFGF (FIG. 4). Therefore, the FGF-induced resistance applies to both antiproliferative and cell kill effects.

Example V

In Vitro Data on the Enhancement of Sensitivity of Tumor Cells to Anticancer Agents Using Inhibitors of aFGF and bFGF This example shows that inhibitors of aFGF and/or bFGF enhanced the tumor sensitivity to anticancer agents.

FIG. 2A shows that inhibition of aFGF and/or bFGF using their respective monoclonal antibodies enhanced the cytotoxicity of paclitaxel, doxorubicin and 5-fluorouracil against human and rodent tumor cells. Likewise, FIG. 2B shows the same findings when anti-aFGF monoclonal antibody and/or anti-bFGF monoclonal antibody were used to remove aFGF and/or bFGF from the cell culture medium. The applicants further show that another inhibitor of aFGF and bFGF, i.e., suramin, also reverses the FGF-induced resistance and enhances the activity of at least 58 anticancer agents under in vitro and/or in vivo conditions (see also Example VIII).

Figure 5:
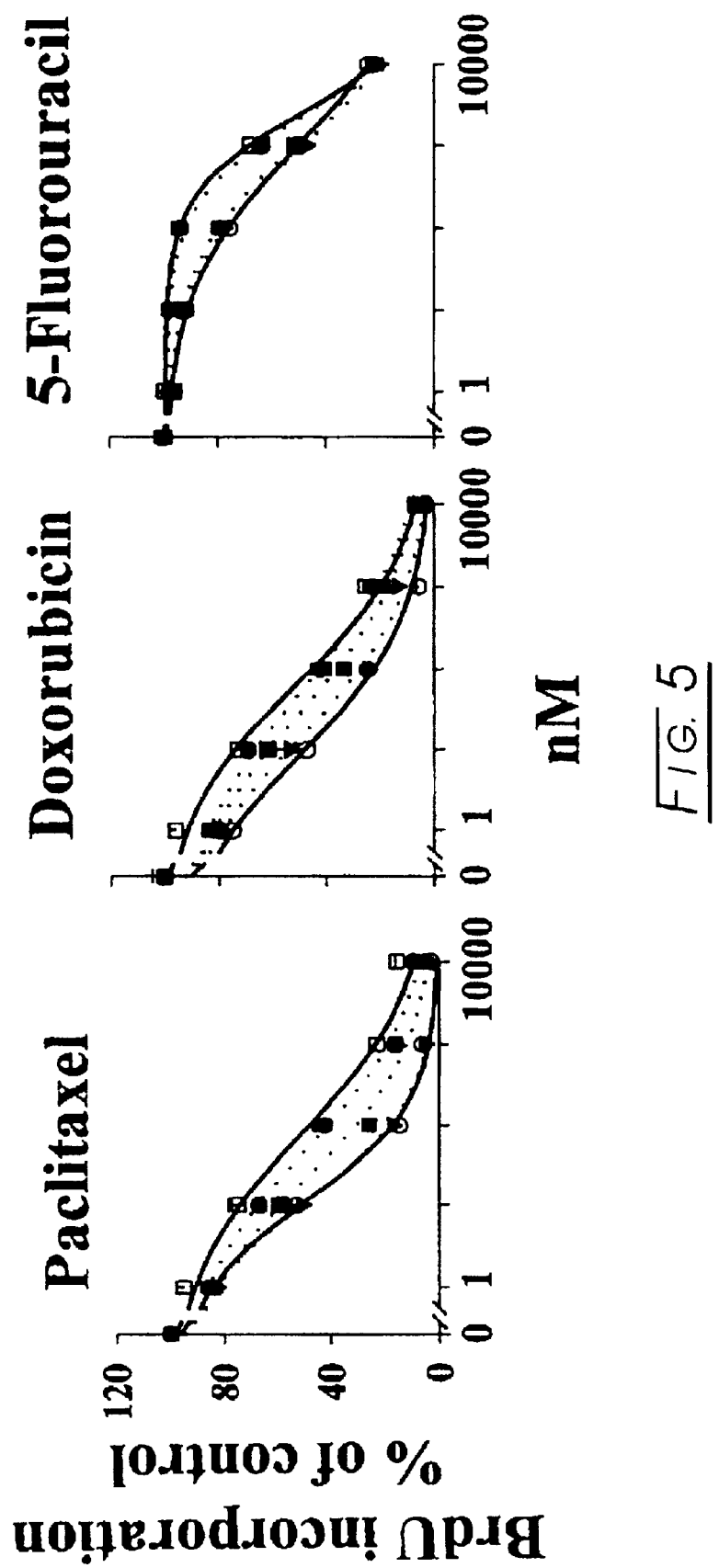
FIG. 5 shows three graphs depicting the cytotoxicity of increasing concentrations of suramin in rat MAT-LyLu tumor cells, human prostate. PC3 and PC3-LN tumor cells. These results show that suramin did not produce measurable cytotoxicity (i.e., <10% reduction in BrdU incorporation) at the 1-15 micromolar concentration. The corresponding $IC_{50}$ values (i.e., suramin concentration required to result in 50% reduction in BrdU incorporation) are 235 micromolar in rat tumor cells, 93 micromolar in PC3 cells and 98 micromolar in PC3-LN cells.

Suramin is a negatively charged molecule that inhibits the action of multiple growth factors including aFGF and bFGF (Middaugh, C. R. et al. (1992) *Biochem*. 31:9016-9024). FIG. 5 shows the results of in vitro experiments demonstrating that addition of suramin produced a concentration-dependent reversal of the CM-induced resistance to paclitaxel, doxorubicin and 5-fluorouracil in rat MAT-LyLu tumor cells, human prostate PC3 tumor cells, and a metastatic subline of PC3, i.e., PC3-LN cells. Complete reversal was attained at between 10 to 15 μM suramin, which, as shown in Example VI, had no antitumor effect when used alone.

Example VI

In Vitro Data on the Enhancement of the Activity of Anticancer Agents Using Low Concentrations of Suramin that Do Not Produce Significant Cytotoxicity This example shows that the enhancement of the activity of anticancer agents by suramin occurs at low suramin concentrations that were sufficient to fully inhibit the FGF-induced chemoresistance but were not sufficient to produce significant cytotoxicity.

Figure 6:
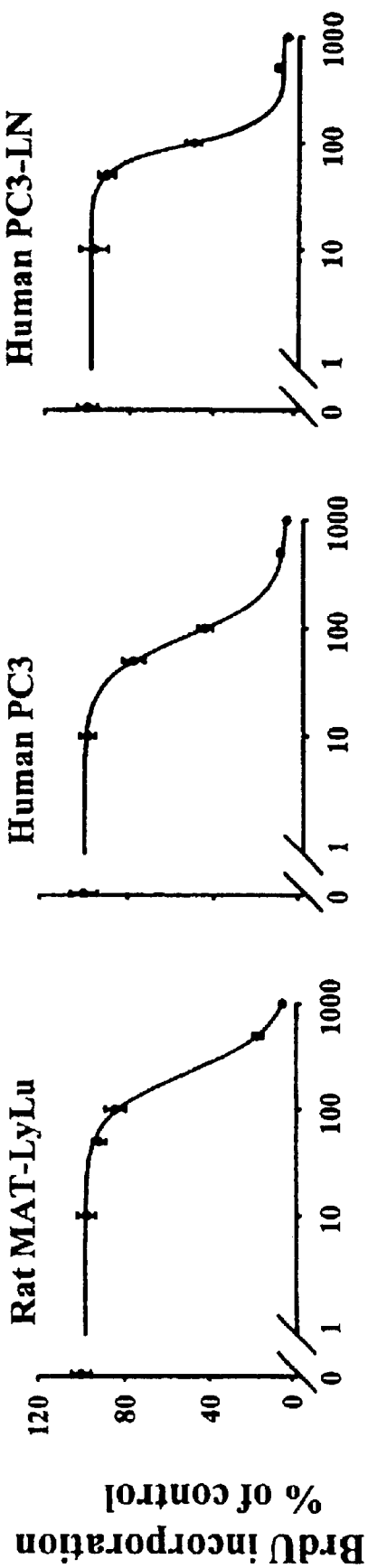
FIG. 6 shows three graphs depicting the enhancement of the cytotoxicity of doxorubicin, paclitaxel and 5-fluorouracil using suramin, under in vitro conditions. The study was performed using rat MAT-LyLu tumor cells (shown here) and human prostate PC3 and PC3-LN tumor cells. The cytotoxic effect was detected by measuring the changes in BrdU incorporation in treated samples relative to control samples. The study used two controls: no CM and no suramin (left solid curves, open circle); with CM of lung histocultures but no suramin (right solid curves, open square). Dotted curves from right to left, addition of suramin 5 μM (filled circle); 10 μM (filled square); and 15 μM (filled inverted triangle). Similar results were obtained for PC3 and PC3-LN cells.

FIG. 6 shows the concentration-response curves of suramin in the tumor cell lines used in the studies described in Examples V and VII. The concentration of suramin, when used alone, required to result in 50% reduction of bromodeoxyuridine incorporation (i.e., $IC_{50}$) were 235 micromolar in rat MAT-LyLu tumor cells, 93 micromolar in human prostate PC3 tumor cells, and 98 micromolar in human prostate PC3-LN tumor cells. These $IC_{50}$ values are between 6- to 200-fold higher than its concentration needed to fully reverse the FGF-induced resistance (between 1 to 15 micromolar, see Examples V and VII and Table 2). At 1-15 micromolar concentration, suramin did not produce measurable cytotoxicity (i.e., <10% reduction in cell number and/or proliferation index). Hence, the enhancement of the antitumor effect of anticancer drugs by suramin occurs at nontoxic concentrations of suramin.

A second study was performed to determine whether suramin, at concentrations sufficient to inhibit the FGF-induced resistance to anticancer agents, fully inhibited the bFGF binding to its receptor. This study was performed using the rat MAT-LyLu tumor cells as the model tumor cells and using doxorubicin and paclitaxel as the model anticancer agents. The CM used to induce resistance was collected from histocultures of lung metastases (see Table 1). Five microgram/ml anti-bFGF antibody was added. The results show that the $IC_{50}$ of doxorubicin and paclitaxel, in the presence of 1.6 micromolar suramin, remained unchanged at 13 and 14 nM, respectively, in the absence or presence of the antibody. This indicates that suramin and the bFGF antibody shared the same action mechanism and that suramin alone at 1-2 micromolar concentrations completely inhibited the bFGF-induced resistance.

Example VII

Broad Spectrum of Anticancer Agents Exhibit aFGF/bFGF-Induced Resistance that is Reversed by Suramin This example summarizes in Table 2 (set forth below) the data showing that aFGF and bFGF induce resistance to at least 58 anticancer agents with a broad spectrum of mechanisms of actions, including antitubulin/antimicrotubule, topoisomerase I inhibitors, topoisomerase II inhibitors, antimetabolites, alkylating agents, and agents that interfere with signal transduction pathways.

The experimental conditions are described briefly below. Human prostate PC3 tumor cells were pretreated with aFGF plus bFGF for 96 hours, followed by drug treatment for 96 hours, with or without 15 micromolar suramin. Cell number was measured using the sulforhodamine B assay which measures the total protein concentration. All drugs listed in Table 2 showed (a) resistance induced by aFGF plus bFGF (i.e. higher $IC_{50}$), and (b) reversal of the resistance by suramin treatment (i.e. suramin treatment reduced the $IC_{50}$ to the original values as without FGF treatment). The FGF-induced resistance was dependent on the FGF concentrations, with a higher resistance at higher FGF concentrations.

TABLE 2

List of anticancer agents which show resistance induced by aFGF/bFGF and reversal of FGF-induced resistance by suramin

| | Drug concentration required to produce 50% inhibition, $IC_{50}$ | | | | | | | |
|---|---|---|---|---|---|---|---|---|
| | Control (drug) treatment only, without FGF treatment) | | aFGF 0.3 ng/ml + bFGF 1 ng/ml | | | aFGF 1 ng/ml + bFGF 3 ng/ml | | |
| Drug class/name | No suramin | Suramin, 15 μM | No suramin | Resistance, Folds | With suramin | No suramin | Resistance, Folds | With suramin |
| Antitubulin/antimicrotubule agents | | | | | | | | |
| Paclitaxel, nM (NSC 125973) | 2.16 | 2.13 | 6.53 | 3.02 | 1.88 | 12.08 | 5.59 | 2.01 |
| Vincristine, nM (NSC 67574) | 6.58 | 6.82 | 26.30 | 4.00 | 6.68 | 44.55 | 6.77 | 7.14 |
| Vinblastine, nM (NSC 49842) | 0.33 | 0.40 | 0.45 | 1.36 | 0.42 | 0.78 | 2.36 | 0.35 |
| Vindesine, nM | 0.39 | 0.35 | 0.53 | 1.36 | 0.37 | 0.82 | 2.10 | 0.43 |
| Vinorelbin, nM | 3.99 | 3.29 | 5.25 | 1.32 | 3.60 | 9.01 | 2.26 | 3.84 |
| Taxotere, nM (NSC 628505) | 2.29 | 2.02 | 2.53 | 1.11 | 2.24 | 3.46 | 1.51 | 2.16 |
| Topoisomerase I inhibitors | | | | | | | | |
| Topotecan, nM (NSC 609699) | 22.16 | 21.67 | 31.09 | 1.40 | 20.78 | 53.88 | 2.43 | 21.01 |
| Camptothecin, nM (NSC94600) | 5.03 | 4.80 | 11.38 | 2.26 | 5.40 | 17.20 | 3.42 | 5.78 |
| Topoisomerase II inhibitors | | | | | | | | |
| Doxorubicin, nM (NSC 123127) | 27.79 | 35.86 | 145.21 | 5.23 | 29.84 | 281.06 | 10.11 | 27.93 |
| Etoposide, micromolar (NSC 141540) | 1.84 | 1.75 | 2.34 | 1.27 | 1.60 | 3.40 | 1.85 | 1.61 |
| Mitoxantrone, micromolar (NSC 301739) | 0.18 | 0.16 | 0.33 | 1.83 | 0.18 | 0.53 | 2.94 | 0.18 |
| Daunorubicin, nM (NSC 82151) | 29.45 | 29.10 | 97.44 | 3.31 | 26.54 | 156.85 | 5.33 | 30.24 |
| Idarubicin, nM (NSC 256439) | 4.45 | 5.05 | 11.88 | 2.67 | 4.45 | 31.21 | 7.01 | 4.30 |
| Teniposide, micromolar (NSC 122819) | 0.40 | 0.42 | 1.14 | 2.85 | 0.39 | 1.98 | 4.95 | 0.36 |
| Amsacrine, micromolar (NSC 249 992) | 0.71 | 0.68 | 1.32 | 1.85 | 0.74 | 1.90 | 2.66 | 0.67 |
| Epirubicin, nM (NSC 256942) | 102.45 | 119.54 | 166.64 | 1.63 | 122.06 | 281.63 | 2.75 | 136.66 |
| Merbarone, micromolar (NSC 336628) | 22.99 | 28.63 | 46.66 | 1.67 | 24.87 | 80.77 | 2.89 | 29.45 |
| Piroxantrone Hydrochloride, micromolar | 0.34 | 0.32 | 0.81 | 2.38 | 0.33 | 1.28 | 3.77 | 0.28 |
| Antimetabolites | | | | | | | | |
| 5-Fluorouracil, micromolar (NSC 19893) | 2.21 | 2.39 | 5.05 | 2.29 | 2.16 | 12.61 | 5.71 | 2.14 |
| Methotrexate, micromolar (NSC 740) | 32.11 | 28.84 | 60.55 | 1.89 | 30.60 | 80.55 | 2.51 | 33.69 |
| 6-Mercaptopurine, micromolar (NSC 755) | 1.57 | 1.67 | 2.99 | 1.90 | 1.70 | 5.50 | 3.50 | 1.55 |
| 6-Thioguanine, micromolar (NSC 752) | 0.28 | 0.32 | 0.96 | 3.43 | 0.32 | 1.44 | 5.14 | 0.30 |
| Fludarabine, micromolar (NSC 321887) | 5.15 | 5.20 | 13.45 | 2.61 | 4.69 | 21.91 | 4.25 | 5.85 |
| Cytarabine/Ara-C, micromolar (NSC 63878) | 0.39 | 0.46 | 1.27 | 3.26 | 0.42 | 3.26 | 8.41 | 0.45 |
| Trimetrexate, nM (NSC 352122) | 33.60 | 33.12 | 54.01 | 1.61 | 30.59 | 95.90 | 2.85 | 28.89 |
| Gemcitabine, nM (NSC 613327) | 6.84 | 6.95 | 9.61 | 1.41 | 6.12 | 13.09 | 1.91 | 5.99 |
| Acivicin, micromolar (NSC 163501) | 1.58 | 1.28 | 3.34 | 2.11 | 1.65 | 5.52 | 3.49 | 1.63 |
| Alanosine, micromolar (NSC 153353) | 2.06 | 2.15 | 4.18 | 2.03 | 2.40 | 7.08 | 3.44 | 2.12 |
| Pyrazofurin, micromolar (NSC 143 095) | 3.38 | 3.83 | 4.07 | 1.20 | 3.65 | 11.06 | 3.27 | 3.80 |
| PALA, micromolar (NSC 224131) | 240.84 | 249.28 | 254.54 | 1.06 | 236.32 | 291.74 | 1.21 | 201.38 |
| Pentostatin micromolar (NSC 218321) | 336.31 | 310.39 | 365.68 | 1.09 | 305.84 | 458.71 | 1.36 | 417.26 |
| 5-Azacitidine, micromolar (NSC 102816) | 6.09 | 6.94 | 13.80 | 2.27 | 6.45 | 26.37 | 4.33 | 7.32 |
| 5-Aza 2'-deoxycytidine, micromolar (NSC 102816) | 6.63 | 6.14 | 14.03 | 2.12 | 6.54 | 26.28 | 3.96 | 6.39 |
| Adenosine arabinoside (Ara-A), micromolar | 21.51 | 22.66 | 33.60 | 1.56 | 18.97 | 45.73 | 2.13 | 20.97 |

TABLE 2-continued

List of anticancer agents which show resistance induced by aFGF/bFGF and reversal of FGF-induced resistance by suramin

| | Drug concentration required to produce 50% inhibition, $IC_{50}$ | | | | | | | |
|---|---|---|---|---|---|---|---|---|
| | Control (drug) treatment only, without FGF treatment) | | aFGF 0.3 ng/ml + bFGF 1 ng/ml | | | aFGF 1 ng/ml + bFGF 3 ng/ml | | |
| Drug class/name | No suramin | Suramin, 15 μM | No suramin | Resistance, Folds | With suramin | No suramin | Resistance, Folds | With suramin |
| Cladribine, micromolar (NSC 105014) | 0.35 | 0.36 | 0.46 | 1.31 | 0.35 | 0.65 | 1.86 | 0.34 |
| 5-Fluorouridine, micromolar (NSC 519273) | 0.28 | 0.28 | 0.44 | 1.57 | 0.33 | 0.70 | 2.50 | 0.29 |
| 5-fluorodoeoxyuridine, nM (NSC 27640) | 5.88 | 7.11 | 9.03 | 1.54 | 6.60 | 12.30 | 2.09 | 5.75 |
| Tiazofurin, micromolar (NSC 286193) | 7.50 | 7.90 | 14.57 | 1.94 | 7.25 | 19.24 | 2.57 | 6.15 |
| Alkylating agents/Intercalating agents | | | | | | | | |
| Cisplatin, micromolar (NSC 119875) | 2.76 | 2.69 | 4.85 | 1.76 | 3.09 | 10.19 | 3.69 | 3.01 |
| Carboplatin, micromolar (NSC 241240) | 2.25 | 2.11 | 3.79 | 1.68 | 2.29 | 9.10 | 4.04 | 2.31 |
| Mitomycin C, micromolar (NSC 26980) | 1.61 | 1.53 | 3.06 | 1.90 | 1.69 | 4.70 | 2.92 | 1.60 |
| BCNU, micromolar (NSC 409962) | 33.51 | 34.23 | 52.24 | 1.56 | 36.52 | 75.64 | 2.26 | 33.33 |
| Melphalan, micromolar (NSC 8806) | 4.19 | 4.02 | 12.85 | 3.07 | 4.48 | 24.61 | 5.87 | 3.97 |
| Thiotepa, micromolar (NSC 6396) | 3.85 | 4.07 | 19.08 | 4.96 | 4.09 | 33.16 | 8.61 | 4.17 |
| Busulfan, micromolar (NSC 750) | 86.21 | 89.20 | 97.85 | 1.14 | 101.83 | 127.45 | 1.48 | 82.77 |
| Chlorambucil, micromolar (NSC 3088) | 31.92 | 33.11 | 53.45 | 1.67 | 44.44 | 88.33 | 2.77 | 37.55 |
| Plicamycin, nM (NSC 24559) | 204.00 | 184.42 | 344.62 | 1.69 | 182.37 | 459.78 | 2.25 | 216.64 |
| Dacarbazine, micromolar (NSC 45388) | 36.63 | 37.61 | 53.69 | 1.47 | 32.41 | 107.94 | 2.95 | 39.68 |
| Ifosfamide, micromolar (NSC 10924) | 2.66 | 2.23 | 5.01 | 1.88 | 2.22 | 8.12 | 3.05 | 2.55 |
| Cyclophosphamide, micromolar (NSC 26271) | 0.51 | 0.48 | 1.11 | 2.18 | 0.57 | 1.53 | 3.00 | 0.50 |
| Nitrogen Mustard, micromolar (NSC 762) | 0.49 | 0.47 | 1.13 | 2.31 | 0.42 | 2.17 | 4.43 | 0.54 |
| Uracil Mustard, micromolar (NSC 34462) | 30.02 | 38.21 | 42.40 | 1.41 | 37.59 | 67.14 | 2.24 | 34.60 |
| Pipobroman, micromolar (NSC 25154) | 136.14 | 93.99 | 193.88 | 1.42 | 125.26 | 183.54 | 1.35 | 108.89 |
| 4-Ipomeanol, micromolar (NSC 349438) | 4105.59 | 4507.00 | 3775.76 | 0.92 | 5040.69 | 5133.55 | 1.25 | 3929.73 |
| Other mechanisms of action | | | | | | | | |
| Dihydrolenperone, micromolar (NSC 343513) | 24.59 | 28.11 | 44.53 | 1.81 | 26.06 | 82.92 | 3.37 | 23.90 |
| Spiromustine, micromolar (NSC 172112) | 25.32 | 24.45 | 54.52 | 2.15 | 25.41 | 87.62 | 3.46 | 26.65 |
| Depsipeptide, nM (NSC 630276) | 1.12 | 1.03 | 1.55 | 1.38 | 1.16 | 2.16 | 1.93 | 1.16 |

Example VIII aFGF/bFGF-Induced Resistance to Anticancer Agents is Detected in Multiple Cancer Cell Lines This example summarizes in Table 3 (set forth below) the data showing that aFGF and bFGF induce resistance to paclitaxel, doxorubicin, 5-fluorouracil, and/or fludarabine in multiple cancer cell lines derived from different human and animal organs, including prostate, lung, pharynx, colon, breast and blood, and a human breast cancer cell line that is stably transfected with the mdr1 gene encoding for p-glycoprotein that is responsible for drug efflux.

The experimental conditions are described briefly below. Cells were pretreated with human recombinant r-aFGF and/or r-bFGF for 96 hours and then with drugs for 96 hours. For the studies on cells derived from the human prostate, lung, pharynx, colon and breast cancer cells, the drug effect was determined by the inhibition of BrdU incorporation. For the study on the human leukemic cells, the drug effect was measured by the MTT assay, which measures the number of metabolically active cells (Alley, M. C. et al (1988) *Cancer Res* 48:589-601).

For the cell lines derived from solid tumors, the results indicate that aFGF alone did not induce resistance, whereas bFGF alone induced resistance in five cell lines A549,(prostate PC3, breast MCF7, mdr1-transfected breast BC19, lung A549, prostate MAT-LyLu) but not in the remaining two cell lines (pharynx FaDu, colon HT29). However, combination of r-aFGF and r-bFGF induced resistance in all seven cell lines, indicating different cells have different requirements of aFGF and bFGF. The results further show that r-aFGF amplified the r-bFGF effect by more than 50-fold (e.g. 1 ng/ml r-aFGF plus 1 ng/ml r-bFGF induced greater resistance than 50 ng/ml r-bFGF alone).

For the human leukemic cell line, i.e., CCRF-CEM, combination of r-aFGF (1 ng/ml) and r-bFGF (3 ng/ml) induced resistance to fludarabine; for a 96 hour treatment, the fludarabine concentration required to produce 50% was increased from 4 micromolar in the absence of FGF to 6 micromolar in the presence of FGF.

TABLE 3

FGF-induced resistance occurs in multiple human and rodent tumor cell lines.

| Cancer Cell line | r-bFGF ng/ml | Drug concentration Needed to produce 50% inhibition, nM | | | r-aFGF ng/ml | Drug concentration needed to produce 50% inhibition, nM | | | r-aFGF + r-bFGF ng/ml | Drug concentration needed to produce 50% inhibition, nM | | |
|---|---|---|---|---|---|---|---|---|---|---|---|---|
| | | Pac | Dox | 5-FU | | Pac | Dox | 5-FU | | Pac | Dox | 5-FU |
| Human prostate PC3 | 0 | 1.2 | 8.1 | 741 | 0 | 1.2 | 8.2 | 810 | 0 | 1.2 | 8.2 | 810 |
| | 1 | 1.2 | 8.51 | 846 | 1 | 1.2 | 8.3 | 815 | 0.04 ± 1 | 1.2 | 8.5 | 761 |
| | 10 | 2.1* | 23.8* | 2409* | 10 | 1.1 | 8.1 | 695 | 0.08 ± 1 | 2.1* | 15.2* | 1147* |
| | 50 | 3.3* | 50.8* | 4303* | 50 | 1.2 | 8.4 | 732 | 0.16 ± 1 | 3.1* | 35.3* | 1636* |
| | | | | | | | | | 0.32 ± 1 | 4.7* | 62.2* | 2542* |
| | | | | | | | | | 0.64 ± 1 | 5.8* | 84.8* | 3772* |
| | | | | | | | | | 1 ± 1 | 6.9* | 107* | 5738* |
| Human lung A459 | 0 | 0.87 | 119 | 870 | 0 | Not measured | 122 | Not measured | 0 | Not measured | 122 | 862 |
| | 1 | 0.9 | 118 | 1008 | 1 | | 120 | | 0.04 ± 1 | | 118 | 908 |
| | 10 | 1.07 | 238* | 1375 | 10 | | 123 | | 0.08 ± 1 | | 159* | 995* |
| | 50 | 1.22 | 285* | 1708* | 50 | | 118 | | 0.16 ± 1 | | 238* | 1009 |
| | | | | | | | | | 0.32 ± 1 | | 309* | 1625* |
| | | | | | | | | | 0.64 ± 1 | | 386* | 2090* |
| | | | | | | | | | 1 ± 1 | | 582* | 3633* |
| Human pharynx FaDu | 0 | 0.77 | 14.2 | 4336 | 0 | 0.82 | 13.5 | 5750 | 0 | 0.82 | 13.5 | 5758 |
| | 1 | 0.79 | 13.9 | 4561 | 1 | 0.80 | 13 | 5503 | 0.04 ± 1 | 0.84 | 13.5 | 5444 |
| | 10 | 0.74 | 14.1 | 4794 | 10 | 0.82 | 13.7 | 5448 | 0.08 ± 1 | 0.82 | 14.0 | 5438 |
| | 50 | 0.82 | 13.7 | 4250 | 50 | 0.83 | 14.0 | 5248 | 0.16 ± 1 | 0.81 | 13.7 | 5471 |
| | | | | | | | | | 0.32 ± 1 | 0.84 | 14.1 | 5557 |
| | | | | | | | | | 0.64 ± 1 | 2.01* | 27.5* | 9694* |
| | | | | | | | | | 1 ± 1 | 3.50* | 54.0* | 15193* |
| Human colon HT-29 | 0 | 2.1 | 24.1 | 2093 | 0 | 2.1 | 30.2 | 1643 | 0 | 2.2 | 30.2 | 1643 |
| | 1 | 2.0 | 24.4 | 2362 | 1 | 2.0 | 32.1 | 1625 | 0.04 ± 1 | 2.0 | 29.1 | 1764 |
| | 10 | 1.9 | 24.5 | 2226 | 10 | 1.9 | 30.3 | 1578 | 0.08 ± 1 | 2.0 | 30.0 | 1550 |
| | 50 | 2.0 | 26.1 | 2252 | 50 | 2.0 | 30.0 | 1634 | 0.16 ± 1 | 2.1 | 30.5 | 1608 |
| | | | | | | | | | 0.32 ± 1 | 3.5* | 48.1* | 2766* |
| | | | | | | | | | 0.64 ± 1 | 6.2* | 72.7* | 5211* |
| | | | | | | | | | 1 ± 1 | 10.8* | 131.4* | 7070* |
| Human breast MCF7 | 0 | 0.32 | 16.9 | 991 | Not measured | | | | | | | |
| | 0.01 | 0.45* | 21.3 | 1028 | | | | | | | | |
| | 0.1 | 0.84* | 37.6* | 1369 | | | | | | | | |
| | 1 | 1.3* | 595* | 1507 | | | | | | | | |
| Human breast BC19 | 0 | 59.6 | 128 | 975 | Not measured | | | | | | | |
| | 0.01 | 112* | 150 | 1068 | | | | | | | | |
| | 0.1 | 183* | 270* | 1373 | | | | | | | | |
| | 1 | 236* | 407* | 1514* | | | | | | | | |
| Rat prostate MAT-LyLu | 0 | 12.7 | 10.3 | 746 | Not measured | | | | | | | |
| | 1 | 16.3 | 18.3* | 1050* | | | | | | | | |
| | 10 | 47.8* | 540* | 1990* | | | | | | | | |
| | 50 | 214* | 238* | 3254* | | | | | | | | |

Pac = paclitaxel;
Dox = doxorubicin;
5-FU = 5-fluorouracil.
The BC19 cell line is a subline of MCF7 transfected with mdr1.
* Indicates p < 0.05 compared to control.

Example IX

In Vivo Data on the Enhancement of the Activity of Anticancer Drugs, Against Well-Established Tumors, Using Nontoxic Doses of Suramin This example describes four studies that provide additional data on the enhancement of the antitumor effect of paclitaxel and doxorubicin by suramin in immunodeficient mice bearing several human xenograft tumors.

The activity of paclitaxel and doxorubicin, with or without suramin, was evaluated in immunodeficient mice (male Balb/c nu/nu mice, 6-8 weeks old). Animal care was in accordance with the guidelines at the Ohio State University. Several human tumor models were used, including (a) lung metastases derived from intravenous injection of human PC3-LN tumor cells, (b) lung tumors derived from direct injection of human PC3 cells in lungs, and (c) subcutaneously implanted PC3 tumors. Four studies were performed. In all studies, drug treatment was administered intravenously via a tail vein, after the tumor was established. The first and second studies used the intravenous PC3-LN lung metastasis model. Briefly, human PC3-LN cells (106 cells in 0.1 ml physiologic saline) were injected intravenously, via a tail vein, into immunodeficient mice. This procedure results in metastasis to lungs in 100% of the animals (Ware, J. L. et al. (1985) *Exp. Cell Biol.* 53:163-169). After 4 weeks, tumor establishment was determined by visual examination of the lungs of two randomly selected animals, and drug treatment in the remaining animals was initiated when these two animals showed at least 5 tumor nodules of 1 mm diameter. Mice received intravenous injection (over 1 min) of 200:1 of either physiologic saline or a saline solution delivering a chemotherapeutic, 10 mg/kg suramin, or a combination of chemotherapeutic and suramin. The chemotherapeutic was doxorubicin (5 mg/kg) for the first study and paclitaxel (Taxol, 15 mg/kg) for the second study. Treatment was given twice weekly for three weeks. Preliminary pharmacokinetic data in rodents indicate that these doses would result in plasma concentrations of approximately 10 nM for doxorubicin, 5-7 nM for paclitaxel and 10 micromolar for suramin at 72 hours. As shown in Example VI, the suramin concentration was sufficient to reverse the FGF-induced chemoresistance. The doxorubicin and paclitaxel concentrations are near or above their $IC_{50}$ in the monolayer cultures of PC3-LN cells (i.e., 17 nM for doxorubicin and 8 nM for paclitaxel). The selected suramin dose has no in vivo antitumor activity against other mouse tumors (Chahinian, A. P. et al. (1998) *J. Surg. Oncol.* 67:104-111; Shin, R., et al. (1997) *Scand. J. Gastroenterol.* 32:824-828). Three days after completion of drug treatments, animals were euthanized and their lungs removed, fixed in Bouin's solution to visualize tumor nodules, and then processed for histologic evaluation. Histologic sections (5 micron thickness) at a depth of between 200-300:m from the ventral surface and containing all 5 lobes of the lungs were obtained. The lung surface area (counted as number of pixel) occupied by the tumor was calculated as a fraction of the total lung area, using Adobe PhotoShop. The number of tumor cells in residual tumors and the fraction of apoptotic cells in each tumor were also determined microscopically. Because apoptotic cells disappear over time, a second measure of the extent of apoptosis was the density of non-apoptotic cells in the residual tumors. This was determined by counting the number of non-apoptotic tumor cells in randomly selected microscopic fields at 400× magnification. On average, ten fields per animal, or >1,500 cells in the control and suramin groups and >600 cells in the doxorubicin group were counted. In the case of combination therapy where fewer than 5 tumor nodules remained per animal, all residual cells (between 20 to 600 cells per animal) were counted.

Both studies show that suramin enhanced the in vivo antitumor effect of drugs in mice bearing well-established human lung metastases.

Table 4 shows the results for doxorubicin. Suramin alone had no significant antitumor effect, nor toxicity. Doxorubicin alone did not eradicate tumors, but reduced the tumor size by ~80%, tripled the fraction of apoptotic cells and halved the density of nonapoptotic cells in residual tumors, and caused a ~20% loss in body weight. All animals in the control and single agent groups had visible tumors on the ventral and dorsal surfaces of the lungs, whereas only 40% of animals in the doxorubicin/suramin combination group showed visible tumors on the lung surface. Histologic section of lung tissues in all animals in the control and single agent groups showed microscopic tumor lesions, whereas only 58% of animals in the doxorubicin/suramin group showed microscopic tumor lesions. Hence, the addition of suramin to doxorubicin therapy significantly enhanced the antitumor effect, resulting in (a) tumor eradication in 42% of animals, and (b) in the remaining 58% of animals which showed residual tumors, further reduction of the tumor size (additional 10-fold), reduction of density of non-apoptotic tumor cells (additional 4-fold), and enhancement of the apoptotic cell fraction (additional 3-fold). Addition of suramin to doxorubicin did not enhance the body weight loss, indicating that suramin did not enhance the host toxicity of doxorubicin.

TABLE 4

Suramin enhances the in vivo antitumor effect of doxorubicin in mice bearing human lung metastases established by intravenous injection of tumor cells.

| Treatment (n) | % Tumor-free animals | % Lung surface area occupied by tumor | % Apoptotic cells per tumor | Density of nonapoptotic cells in residual tumors, cells/field of | End-of-experiment body weight, % pretreatmen value |
|---|---|---|---|---|---|
| Saline control (10) | 0 | 9 ± 4 | 9 ± 6 | 157 ± 37 | 104 ± 5 |
| Suramin, 10 mg/kg (10) | 0 | 7 ± 3 | 10 ± 7 | 139 ± 30 | 101 ± 10 |
| Doxorubicin, 5 mg/kg (10) | 0 | 2 ± 1* | 29 ± 16* | 77 ± 17* | 82 ± 4* |
| Doxorubicin + Suramin (12) | 42\ | 0.2 ± 0.3† | 77 ± 12† | 22 ± 14† | 84 ± 8* |

The average pretreatment weights for the four groups ranged from 21 g to 22 g. Animals that did not show visible tumors on the lung surface nor microscopic lesions in 5 random histologic sections are considered tumor-free. Mean ± SD.
*$p < 0.05$ compared to the control and suramin groups.
†$p < 0.05$ compared to all other groups.

Similar findings were observed for the effect of suramin on paclitaxel. Table 5 shows that suramin alone had no significant antitumor effect, nor toxicity. Paclitaxel alone reduced the density of nonapoptotic cells by ~70%, increased the fraction of apoptotic cells by 13-fold, and caused a ~7% loss in body weight. The addition of suramin to paclitaxel therapy significantly enhanced the antitumor effect, resulting in further reduction of the density of non-apoptotic tumor cells (additional 30-fold), and nearly doubled the apoptotic cell fraction. Addition of suramin to paclitaxel therapy did not enhance the body weight loss, indicating that suramin did not enhance the host toxicity of paclitaxel.

TABLE 5

Suramin enhances the in vivo antitumor effect of paclitaxel in mice bearing human lung metastases established by intravenous injection of tumor cells. The average pretreatment weights for the four groups ranged from 21 g to 22 g.

| Treatment (n) | % Apoptotic cells per tumor | Density of nonapoptotic cells in residual tumors, cells/field | End-of- experiment body weight, % of pretreatment value |
|---|---|---|---|
| Saline control (4) | 4 ± 2 | 171 ± 35 | 96 ± 11 |
| Suramin, 10 mg/kg (4) | 4 ± 3 | 185 ± 104 | 101 ± 5 |
| Paclitaxel, 15 mg/kg (4) | 53 ± 24* | 49 ± 35* | 93 ± 11 |
| Paclitaxel + Suramin (4) | 98 ± 7† | 1.6 ± 6† | 92 ± 8 |

Mean ± SD.
*$p < 0.05$ compared to the control and suramin groups.
†$p < 0.05$ compared to all other groups.

The third study shows enhancement of doxorubicin activity in lung tumors established by intra-organ tumor cell injection. Briefly, PC3 cells were directly injected into the lungs of immunodeficient mice ($2.5 \times 10^6$ cells per lung). Tumor establishment (on day 5) was verified by visual examination of a randomly selected animal. The remaining animals were given intravenous bolus injection of doxorubicin (three doses of 10 mg/kg each given on day 5, 8 and 11) alone, suramin alone (three doses of 20 mg/kg), or a combination of both drugs. Animals were euthanized on day 12. Lungs were removed and examined visually for residual tumors. Histologic sections were obtained and examined microscopically, as described for the first two studies. No animals in the untreated control group (n=4) and the suramin group (n=3) were free of tumors, whereas the doxorubicin group (n=4) showed one tumor-free animal (25%), and all animals in the doxorubicin/suramin combination group (n=5) was tumor-free (100%). The differences between the combination group and the other three groups were significant ($p<0.04$). These data show that suramin enhanced the antitumor activity of doxorubicin.

The fourth study shows that suramin enhanced the antitumor effect of doxorubicin in subcutaneous bulky tumors. Briefly, PC3 cells ($5 \times 10^6$ cells) were injected subcutaneously. Drug treatments (suramin 10 mg/kg, doxorubicin 5 mg/kg, or a combination of both drugs, given twice weekly for 3 weeks) were initiated after tumor establishment. The average tumor size was 150 mg at the time of first treatment.

Figure 7B:
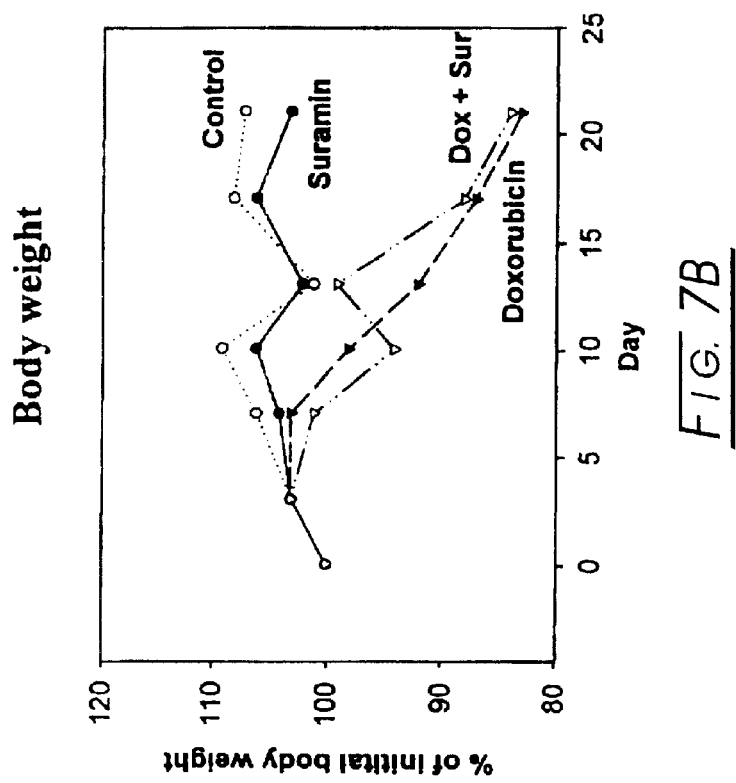
FIGS. 7A-7B are two graphs depicting the suramin-mediated enhancement of doxorubicin activity in immunodeficient mice bearing subcutaneous bulky human prostate PC3 xenograft tumors.
Figure 7A:
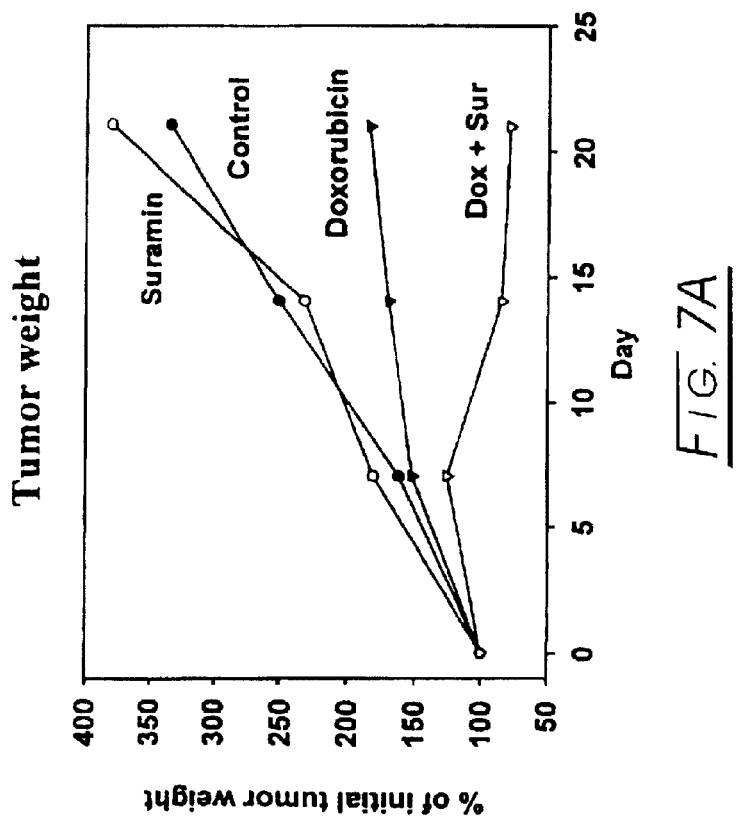

FIG. 7A shows (a) a 3- to 4-fold increase of tumor size in the untreated control group and suramin group, indicating that suramin alone had no antitumor activity, (b) doxorubicin alone reduced the tumor growth but did not cause tumor regression, (c) doxorubicin+suramin combination reduced the tumor growth during the first week, followed by tumor regression until the end of the 3-week treatment. Results on the animal body weight (FIG. 7B) indicate (a) suramin alone did not cause body weight loss, (b) doxorubicin produced a 17% body weight loss, and (c) addition of suramin to doxorubicin did not enhance body weight loss.

Example X

Relationship Between aFGF and bFGF Levels in Tumor, Tumor Size, and Tumor Sensitivity to Anticancer Agents This example demonstrates a correlation between aFGF and bFGF level in tumor and tumor size, and a correlation between bFGF level in tumor and tumor sensitivity to anticancer agents.

The first study examined the effect of the presence of tumor cells on the extracellular bFGF levels in tissues. Briefly, human prostate PC3 tumor cells were implanted intradermally or directly into the lungs of immunodeficient mice. Tumors were removed from animals and ~10 mg were cultured as histocultures. The culture medium was collected at 24 hours and analyzed for bFGF. The bFGF level in PC3 cells was 2 pg/$10^6$ cells (approximately 2 pg/mg), 0.13 pg/mg in normal lung tissue, 0.62 pg/mg in normal skin tissue, 3.2 pg/mg in PC3-containing lung tumor, and 11.3 pg/mg in PC3-containing skin tumor. Hence, the bFGF levels in tumor-bearing tissues exceeded the sum of bFGF levels in tumor cells and normal tissues, indicating that the presence of tumor cells enhanced bFGF level. The enhancement was 25-fold in lungs and 18-fold in skin. For comparison, the mouse brain contained 0.027 pg bFGF per mg tissue and the liver contained 0.636 pg bFGF per mg tissue. The results indicate (a) different bFGF levels in different tissues, and (b) presence of tumor cells significantly enhanced the bFGF levels.

The second study examined the relationship between the extracellular bFGF level and tumor size. Human prostate PC3 tumor cells were implanted subcutaneously in immunodeficient mice. Subcutaneous tumor were removed from host animals after 1 to 7 weeks, and ~200 mg were cultured as histocultures. The culture medium was collected at 24 hours and analyzed for bFGF concentration by ELISA. The bFGF level increased with time, from 27 pg/ml in week 1 tumor, to 56 pg/ml in week 2 tumor, to 77 pg/ml in week 3 tumor, and reached a plateau level of between 80 to 87 pg/ml between week 4 and week 7 tumors. The differences between the bFGF levels in weeks 1, 2 and 3 are statistically significant. This indicates a positive correlation between bFGF level and tumor size.

The third study examined the relationship between the levels of aFGF and bFGF in human tumors and tumor sensitivity to anticancer agents. This study was performed using 96 tumors obtained from human patients, including include bladder, breast, head and neck, ovarian and prostate tumors. Paclitaxel was used as the model drug. Briefly, histocultures of bladder tumors were treated with paclitaxel for 2 hours and the remaining tumors for 96 hours. The drug-induced antiproliferation was measured by inhibition of DNA precursor incorporation, and apoptosis was measured by morphological changes and by labeling of nicked DNA. aFGF, bFGF and other proteins known to contribute to drug resistance (i.e. the mdr1 p-glycoprotein, p53 and bcl-2) were detected by immunohistochemical staining.

Sixty-four % (61/96) of the tumors showed positive bFGF staining. aFGF is highly expressed in bladder tumors. Ovarian and prostate tumors have intermediate aFGF levels with low positive rates in head and neck and breast tumors. aFGF was only found in the cytoplasm. Paclitaxel produced antiproliferation in 84% of the tumors and induced apoptosis in 96% of the tumors. bFGF expression correlated with resistance to paclitaxel-induced antiproliferation (p<0.001) and paclitaxel-induced apoptosis (p=0.13). Statistical analyses using multiple regression and the Akaike Information Criterion show that among the pathobiological parameters including tumor stage, grade, proliferation index, and expression of bFGF, p-glycoprotein, p53 and bcl-2 proteins, bFGF expression was the best indicator of resistance to the antiproliferative effect and the overall cytotoxicity (i.e., antiproliferation plus apoptosis) of paclitaxel in tumors obtained from human patients (see Table 6 set forth below). Addition of aFGF to bFGF improves the correlation (Table 6).

Collectively, these results indicate the levels of aFGF and bFGF in tumors is determined by the location of the tumor and the size of the tumor, and that the aFGF/bFGF level, in turn, determines the tumor sensitivity to anticancer agents. The varying FGF level in tumors indicates the use of FGF level for making therapeutic decision for individual patients.

TABLE 6

Correlation between pathobiological parameters and chemosensitivity.

| Antiproliferation, maximum effect (%) | $r^2$ | AIC | p Value |
|---|---|---|---|
| bFGF | 0.16 | 595 | <0.001 |
| Tumor stage | 0.14 | 596 | <0.001 |
| P-glycoprotein (Pgp) | 0.11 | 600 | 0.001 |
| Proliferation index (PI) | 0.08 | 603 | 0.006 |
| Tumor grade | 0.07 | 604 | 0.01 |
| P53 | 0.06 | 605 | 0.02 |
| Bcl-2 | 0.05 | 606 | 0.03 |
| aFGF | 0.03 | 608 | 0.1 |
| bFGF + Stage | 0.26 | 584 | <0.001 |
| bFGF + aFGF | 0.23 | 588 | <0.001 |
| bFGF + Stage + bcl-2 | 0.30 | 581 | <0.001 |
| bFGF + Stage + bcl-2 + p53 | 0.33 | 579 | <0.001 |
| bFGF + Stage + bcl-2 + p53 + PI | 0.34 | 579 | <0.001 |

TABLE 6-continued

Correlation between pathobiological parameters and chemosensitivity.

| | $r^2$ | AIC | p Value |
|---|---|---|---|
| bFGF + Stage + bcl-2 + p53 + PI + Pgp | 0.34 | 581 | <0.001 |
| bFGF + Stage + bcl-2 + p53 + PI + Pgp + Grade | 0.35 | 582 | <0.001 |

| Overall effect (antiproliferation plus apoptosis) | $R^2$ | AIC | p Value |
|---|---|---|---|
| bFGF | 0.12 | 587 | <0.001 |
| Proliferation index (PI) | 0.11 | 588 | 0.001 |
| Tumor Stage | 0.10 | 589 | 0.001 |
| P53 | 0.08 | 591 | 0.004 |
| Bcl-2 | 0.03 | 596 | 0.10 |
| P-glycoprotein (Pgp) | 0.03 | 596 | 0.10 |
| aFGF | 0.03 | 600 | 0.1 |
| Tumor Grade | 0.03 | 597 | 0.11 |
| bFGF + PI | 0.20 | 580 | <0.001 |
| bFGF + aFGF | 0.18 | 582 | <0.001 |
| bFGF + aFGF + PI | 0.24 | 577 | <0.001 |
| bFGF + aFGF + PI + p53 | 0.28 | 574 | <0.001 |
| bFGF + aFGF + PI + p53 + bcl-2 | 0.30 | 573 | <0.001 |
| bFGF + aFGF + PI + p53 + Bcl-2 + Stage | 0.30 | 574 | <0.001 |
| bFGF + aFGF + PI + p53 + Bcl-2 + Stage + Pgp | 0.31 | 575 | <0.001 |

A higher $r^2$ value (from multiple regression analysis) and a lower AIC value (from Akaike Information Criterion analysis) indicate a better predictive value. For multiple-parameter combinations, the best prognostic indicators are those that give the highest $r^2$ values as well as the lowest AIC values. Statistical analysis was performed using linear regression analysis using REG sorfware. A p value of less than 0.05 is statically significant.

Example XI

Treatment of Cancer Cells with Anticancer Agents Enhanced Extracellular bFGF Levels This example summarizes in Table 7 (set forth below) the data showing that treatment of human prostate PC3 tumor cells with at least 7 anticancer agents with diverse action mechanisms and chemical structures (e.g., antimicrotubules, topoisomerase I inhibitor, topoisomerase II inhibitor, DNA alkylating agents) significantly enhanced the levels of extracellular bFGF.

The experimental conditions are described briefly below. Human prostate PC3 tumor cells were treated with drugs for 72 hours. The remaining cell number at the end of treatment was counted using a Coulter counter. The extracellular bFGF concentration was measured using ELISA. The release of lactate dehydrogenase (LDH) into the extracellular culture medium is indicative of cell death and gives a measure of the release of cellular content into the culture medium. If the increase in extracellular bFGF level is due to the release of bFGF upon cell death and lysis, the increase in bFGF will be accompanied by an increase in LDH in the same extent. This would result in an higher bFGF level and a constant bFGF-to-LDH ratio. On the other hand, an increase in extracellular bFGF due to an increase in bFGF production and release of bFGF from cells by processes other than cell lysis will result in an higher bFGF level and an higher bFGF-to-LDH ratio.

The results, listed in Table 7, show that treatments with all of the tested drugs resulted in 3- to 30-fold higher extracellular bFGF levels (p<0.05). These higher bFGF levels were attained in spite of the up to 80% reduction in cell number, indicating an even greater bFGF production in the drug-treated cells on a per cell basis, relative to untreated controls. The increases in bFGF level were accompanied by higher bFGF-to-LDH ratios, indicating that the increase in extracellular bFGF level was at least in part due to increased production and release of bFGF from live cells.

The enhancement of extracellular bFGF level in tumor cells due to drug treatment indicates that patients that have been treated with chemotherapy are likely to exhibit chemoresistance. This in turn indicates the need of using inhibitors of FGF to treat patients who have failed cancer therapy and have recurrent tumors.

TABLE 7

Drug treatment enhances bFGF production and release into extracellular space

| Drug concentration NM | Remaining cell number at 72 hours × $10^6$ (% of control) | bFGF, pg/ml | Extracellular concentration bFGF, % of control | LDH, % of control | bFGF:LDH ratio |
|---|---|---|---|---|---|
| Paclitaxel | | | | | |
| 0 | 2.3 (100%) | 5.62 | 100 | 100 | 1.00 |
| 2.5 | 2.0 (87%) | 19.5 | 347 | 225 | 1.54 |
| 5 | 1.0 (43%) | 76.3 | 1358 | 437 | 3.11 |
| 10 | 0.5 (22%) | 164 | 2917 | 705 | 4.14 |
| Doxorubicin | | | | | |
| 0 | 2.5 (100%) | 4.72 | 100 | 100 | 1.00 |
| 20 | 2.1 (84%) | 5.87 | 124 | 119 | 1.05 |
| 60 | 1.2 (48%) | 11.3 | 239 | 173 | 1.38 |
| 200 | 0.4 (16%) | 21.8 | 461 | 316 | 1.46 |
| Vinblastine | | | | | |
| 0 | 2.3 (100%) | 8.76 | 100 | 100 | 1.00 |
| 0.5 | 1.7 (74%) | 59.1 | 675 | 263 | 2.57 |
| 1 | 1.0 (43%) | 94.0 | 1073 | 326 | 3.29 |
| 2 | 0.4 (17%) | 179 | 2046 | 513 | 3.99 |
| 5-Fluorouracil | | | | | |
| 0 | 2.5 (100%) | 6.00 | 100 | 100 | 1.00 |
| 2000 | 2.2 (88%) | 8.37 | 139 | 121 | 1.15 |
| 6000 | 1.4 (56%) | 11.35 | 189 | 158 | 1.20 |
| 20000 | 0.6 (24%) | 17.8 | 296 | 202 | 1.46 |
| Cisplatin | | | | | |
| 0 | 2.2 (100%) | 6.14 | 100 | 100 | 1.00 |
| 2000 | 1.9 (86%) | 5.87 | 267 | 169 | 1.58 |
| 6000 | 1.0 (45%) | 95.9 | 1561 | 534 | 2.92 |
| 20000 | 0.4 (18%) | 101 | 1641 | 563 | 2.88 |
| Camptothecin | | | | | |
| 0 | 2.4 (100%) | 6.27 | 100 | 100 | 1.00 |
| 2 | 2.0 (83%) | 9.08 | 145 | 137 | 1.06 |
| 6 | 1.2 (50%) | 13.9 | 221 | 182 | 1.22 |
| 20 | 0.5 (21%) | 17.5 | 279 | 219 | 1.28 |

Example XII

FGF-Induced Resistance to Anticancer Agents is Not Due to Altered Drug Accumulation nor Altered Cell Proliferation This example demonstrates that FGF-induced resistance to anticancer agents is a novel mechanism that is different from the previously reported mechanisms of chemoresistance that involve an enhancement of drug efflux and altered cell proliferation.

The experimental conditions are briefly described below. Human prostate PC3 tumor cells and rat MAT-LyLu tumor cells were treated with $^3$H-paclitaxel (1 nM for human PC3 cells and 10 nM for rat tumor cells), $^{14}$C-doxorubicin (50 and 100 nM, respectively), and $^3$H-5-fluorouracil (500 nM for both cells) (Au, J. L.-S. et al. (1998) supra), with or without with the active CM collected from histocultures of lung metastases or with r-bFGF. The extracellular drug concentrations were selected based on their $IC_{50}$ (50% inhibitory concentration) in human and rat cells. The plateau intracellular drug concentrations which were attained at 4 hours for all three drugs in PC3 cells, and 1 (doxorubicin and 5-fluorouracil) and 4 hours (paclitaxel) in rat cells, were measured.

The results show that these treatments did not alter the drug accumulation in tumor cells; the respective intracellular concentrations of paclitaxel, doxorubicin and 5-fluorouracil remained unchanged at ~0.5, 40, and ~0.1 pmol/$10^6$ cells in human PC3 tumor cells; and 1, 80, and 24 pmol/$10^6$ cells in rat tumor cells (n=6 each). Therefore, the FGF-induced chemoresistance is not due to reduced drug accumulation, as previously reported for overexpression of drug efflux proteins (Lum, B. L. et al. (1993) *Cancer* 72, 3502-3514; Barrand, M. A. et al. (1997) *Gen. Pharmacol.* 28, 639-645; Fidler, I. J. (1999) *Cancer Chemother. Pharmacol.* 43:S3-S10).

Treatment with the CM or r-bFGF also did not alter the doubling time of exponentially growing cells, which remained unchanged at 17 and 24 hours for rat and PC3 tumor cells, respectively. Hence, the FGF-induced chemoresistance is not due to altered cell proliferation.

Example XIII

FGFs Induce a Novel Epigenetic Mechanism of Broad Spectrum Resistance to Anticancer Drugs The findings described herein demonstrate (a) a novel epigenetic mechanism by which cancer cells utilize the unique microenvironment of solid tumors and metastases to elude cytotoxic insult, (b) establish an important role of extracellular growth factors in tumor sensitivity to chemotherapy, and (c) indicate a new treatment paradigm using combinations of chemotherapy with aFGF/bFGF inhibitors.

These results establish a new mechanism of broad spectrum anticancer drug resistance that is mediated primarily by extracellular aFGF/bFGF and does not involve significant changes in intracellular drug accumulation, nor cell proliferation. The reversal of the resistance by inhibition of extracellular aFGF/bFGF suggests a mechanism that involves binding of these proteins to their receptors.

The correlation between the concentrations of extracellular aFGF/bFGF and tumor location and the progressive loss of these proteins upon disaggregation of metastatic tumors and passaging the disaggregated cells in monolayers indicate a relationship between the aFGF/bFGF concentrations and the tumor growth environment. The findings disclosed herein of higher bFGF concentrations in metastases, compared to primary tumors, is consistent with the higher urinary bFGF concentration observed in patients with metastatic cancer compared to localized cancer (Huang, A. et al. (1994) Exp. Cell Res. 213, 335-339). The significant resistance induced by aFGF/bFGF at concentrations found in the active metastatic tumor CM and in patients (Huang, A. et al. (1994, supra) indicates the importance and clinical relevance of this resistance mechanism, and suggests elevated aFGF/bFGF concentrations in metastases as an important mechanism that limits the efficacy of chemotherapy in metastatic disease. The extent of in vivo chemoresistance may be higher than the 3- to 10-fold resistance induced by the CM, because the aFGF/bFGF concentrations in the local environment within solid tumors are likely to exceed their concentrations in the CM which was diluted 500- to 1,000-fold during collection.

Example XIV: Protection of Gastrointestinal Cells from Cytotoxicity of Anticancer Agents by FGF This example shows that treatment of non-cancerous intestinal epithelium with aFGF and bFGF protects these cells from the toxicity of anticancer agents, such as paclitaxel and doxorubicin.

Briefly, normal rat intestinal epithelial cells (IEC6) were used. These cells were derived from normal, noncancerous intestinal epithelium. Cells were pretreated with 1 ng/ml aFGF and 3 ng/ml bFGF for 96 hours and then with doxorubicin or paclitaxel for 24 hours. Drug effect was measured as the reduction of bromodeoxyuridine incorporation in treated cells relative to untreated controls. The results show that the $IC_{50}$ for doxorubicin was increased from 292 nM in the absence of aFGF and bFGF to 544 nM in the presence of aFGF and bFGF, and the $IC_{50}$ for paclitaxel was increased from 491 nM to 1446 nM. This indicates that aFGF/bFGF treatment protects normal intestinal cells from the toxicity of anticancer agents.

Example XV

Cell Culture Systems

Cell culture assay experiments can be performed in the rat prostate MAT-LyLu tumor cells, and the human prostate PC3 tumor cells or its metastatic subline PC3-LN cells. If the requirements of the invention are met in any of the three cell cells, the choice and the dosage of the FGF antagonist is suitable for use in the invention. Preferably the PC3 cells are used.

Human prostate PC3 tumor cells can be obtained from the American Type Culture Collection. The rat MAT-LyLu tumor cells and PC3-LN cells were obtained from Dr. John Isaacs (Johns Hopkins University) and Dr. Joy Ware (University of Virginia), respectively. The doubling time of PC3 and PC3-LN cells is approximately 24-hour, the doubling time of MAT-MAT-LyLu cells is approximately 15-17 hr. All three cell lines should be cultured as monolayers in a humidified environment containing 5% $CO_2$ and 95% air, at 37° C. PC 3 cells and PC3-LN cells should be maintained in RPMI 1640 medium supplemented with 9% heat-inactivated fetal bovine serum, 2 mM 1-glutamine, 100:g/ml gentamicin, and 95:g/ml cefotaxime. MAT-LyLu cells should be maintained in RPMI 1640 medium containing 100:g/ml gentamicin, 95:g/ml cefotaxime and 9% heat-inactivated fetal bovine serum.

Cells are harvested from subconfluent cultures using trypsin and resuspended in fresh medium before plating. Cells with >90% viability, as determined by trypan blue exclusion, are used to evaluate the cytotoxicity of an FGF antagonist, e.g., suramin. Cells are plated in 96 well microtiter plates at a density such that confluence would not be achieved at the end of the drug treatment period. Cells are allowed to attach to the plate surface by growing in drug-free medium for 20 to 24 hr. Afterward, cells are incubated with the FGF antagonist (one example used 0.2 ml of suramin)-containing culture medium, at concentrations spanning at least 4 log scales. The drug effect should be measured as inhibition of BrdU incorporation, e.g., according to the Cell Proliferation ELISA BrdU (Boehringer Mannheim).

Example XVI

Inhibition of FGF Binding to FGF Receptors

This example describes the inhibition of the binding of FGF to FGF receptors by FGF antagonists.

The effects of several FGF antagonists (i.e., suramin, heparin, low molecular weight heparin, heparan sulfate) on the binding of $^{125}I$-bFGF on FGF receptors in human prostate cancer PC3 cells and human breast cancer MCF7 cells were studied. Briefly, cells were plated at $1 \times 10^5$ cells per 16 mm well on 24-well plates and were allowed to settle for 48 hours before binding experiment. On the day of the experiment, cells were incubated for 2 hours at 37° C. in serum-free DMEM supplemented with 0.15% gelatin. Cells were then washed twice with ice-cold phosphate buffered saline. Aliquots of bFGF antagonist in cold DMEM binding buffer (100:1, containing 25 mM HEPES, 0.15% gelatin, pH 7.5) at various concentration and $^{125}I$-bFGF (100:1) at various concentrations in the same buffer were added in each well. At the end of the incubation, the cells were either washed three times with 1 ml ice-cold phosphate-buffered saline or washed twice with ice-cold phosphate-buffered saline followed by one wash of 1 ml 2 M NaCl in 25 mM HEPES, pH 7.5. The cells were then extracted with 0.25 ml 0.5% Triton X-100 and the radioactivity in the extract was determined in a gamma scintillation counter.

The results, summarized in Table 8, show that the FGF antagonists inhibited the high affinity and total binding of $^{125}I$-bFGF in PC3 and MCF7 cells.

TABLE 8

Inhibition of binding of $^{125}$I-bFGF to FGF receptors by FGF antagonists.

| FGF antagonist | IC$_{50}$ for high affinity binding | | IC$_{50}$ for total binding | |
|---|---|---|---|---|
| | PC3 | MCF7 | PC3 | MCF7 |
| Suramin | 87:g/ml | 21:g/ml | 87:g/ml | 17:g/ml |
| Heparin | <0.001:g/ml | — | 0.001:g/ml | — |
| Low mol wt heparin | — | 10:g/ml | — | 0.5:g/ml |
| Heparan sulfate | — | 1:g/ml | — | 5:g/ml |

Example XVII

Genetic Changes Induced by Extracellular bFGF

Differential display was used to identify the down-stream genes that are involved in the bFGF-induced multidrug resistance. These genes were identified by comparing the effect of bFGF on the expression of these genes in a cell line that demonstrates bFGF-induced chemoresistance (i.e. human prostate cancer PC3 cells) with that in a cell line which does not show bFGF-induced chemoresistance (i.e. human head and neck cancer FaDu cells). By this method, the genes that were altered by bFGF treatment in PC3 cells but not in FaDu cells were identified. The identified genes are likely to be associated with the bFGF-induced multidrug resistance.

For differential display, total RNA was isolated from the cells and reverse-transcripted in single strand cDNA. PCR was performed using a pair of T and P primers. One pair of primers displayed about 50-100 bands. 90 T and P primer combinations which displayed about 6000 cDNA bands were used. Fourteen bands showed either increase or decrease in density in PC3 cells after bFGF treatment. Five of these bands were reproducibly altered in PC3 cells, but not in FaDu cells. These bands were cut from the gels, reamplified and cloned into pGEM-T vector. Nine different clones were identified and sequenced. The gene sequence was compared to the data in the NCBI GenBank. The comparison showed that 5 clones corresponded to previously reported genes, and 4 clones were not-yet-reported and therefore potentially new genes. Primers were synthesized for drug resistant cancer cells. Among the nine clones, five were altered reproducibly by bFGF treatment while bFGF had no effect on the remaining four clones. The expression of two of the known genes, TSC22 and VEGF, were increased by 20 to 40%, whereas the expression of the three new genes (temporarily named FSC-1, FSC-2, and FSC-3) were induced by 65%, 300%, and 40%. TSC22 and VEGF are not known to be regulated by bFGF.

Expression of the transcription factor TFII-I was also identified to be upregulated by extracellular bFGF. Using differential display, cloning and sequencing techniques, another cDNA (256 bp) was identified which showed only partial (i.e. ~60%) matches with several segments in the human PAC and BAC clones, indicating this as a not-yet reported gene.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A method of protecting a hair follicle cell of a subject from damage caused by a cytotoxic agent administered to said subject, comprising administering to the hair follicle cell of said subject an effective amount of at least one FGF agonist consisting of bFGF or a combination of aFGF and bFGF, thereby protecting or reducing the damage to the hair follicle cell from said cytotoxic agent, wherein administration of the FGF agonist does not result in significant systemic administration of the FGF agonist, said cytotoxic agent being paclitaxel.

2. A method of protecting a hair follicle cell of a subject from damage caused by a cytotoxic agent administered to said subject, comprising administering to the hair follicle cell of said subject an effective amount of at least one FGF agonist consisting of bFGF or a combination of aFGF and bFGF, thereby protecting or reducing the damage to the hair follicle cell from said cytotoxic agent, wherein administration of the FGF agonist does not result in significant systemic administration of the FGF agonist, said cytotoxic agent being doxorubicin.

3. A method of protecting a hair follicle cell of a subject from damage caused by a cytotoxic agent administered to said subject, comprising administering to the hair follicle cell of said subject an effective amount of at least one FGF agonist consisting of bFGF or a combination of aFGF and bFGF, thereby protecting or reducing the damage to the hair follicle cell from said cytotoxic agent, wherein administration of the FGF agonist does not result in significant systemic administration of the FGF agonist, said cytotoxic agent being cyclophosphamide.

4. The method of claim 1, wherein the FGF agonist is administered topically.

5. The method of claim 1, wherein the FGF agonist is a combination of aFGF and bFGF.

6. The method of claim 4, wherein the FGF agonists is a combination of aFGF and bFGF.

7. The method of claim 1, wherein hair loss of said subject is inhibited.

8. The method of claim 1, wherein said administering is repeated.

9. The method of claim 1, wherein said administering of said bFGF or combination of aFGF and bFGF is one or more of sequentially or simultaneously with said cytotoxic agent.

10. The method of claim 2, wherein the FGF agonist is administered topically.

11. The method of claim 2, wherein the FGF agonist is a combination of aFGF and bFGF.

12. The method of claim 10, wherein the FGF agonists is a combination of aFGF and bFGF.

13. The method of claim 2, wherein hair loss of said subject is inhibited.

14. The method of claim 2, wherein said administering is repeated.

15. The method of claim 2, wherein said administering of said bFGF or combination of aFGF and bFGF is one or more of sequentially or simultaneously with said cytotoxic agent.

16. The method of claim 3, wherein the FGF agonist is administered topically.

17. The method of claim 3, wherein the FGF agonist is a combination of aFGF and bFGF.

18. The method of claim 16, wherein the FGF agonists is a combination of aFGF and bFGF.

19. The method of claim 3, wherein hair loss of said subject is inhibited.

20. The method of claim 3, wherein said administering is repeated.

21. The method of claim 3, wherein said administering of said bFGF or combination of aFGF and bFGF is one or more of sequentially or simultaneously with said cytotoxic agent.

* * * * *